United States Patent
Rajesh et al.

(10) Patent No.: US 10,961,505 B2
(45) Date of Patent: Mar. 30, 2021

(54) GENERATING MATURE LINEAGES FROM INDUCED PLURIPOTENT STEM CELLS WITH MECP2 DISRUPTION

(71) Applicant: FUJIFILM Cellular Dynamics, Inc., Madison, WI (US)

(72) Inventors: Deepika Rajesh, Madison, WI (US); Anne Strouse, Madison, WI (US); Sarah Burton, Madison, WI (US); Christie Munn, Madison, WI (US); Bradley Swanson, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 387 days.

(21) Appl. No.: 15/725,931

(22) Filed: Oct. 5, 2017

(65) Prior Publication Data

US 2018/0179496 A1 Jun. 28, 2018

Related U.S. Application Data

(60) Provisional application No. 62/404,430, filed on Oct. 5, 2016.

(51) Int. Cl.
| | |
|---|---|
| *C12N 5/078* | (2010.01) |
| *C12N 5/0783* | (2010.01) |
| *C12N 5/071* | (2010.01) |
| *C12N 5/079* | (2010.01) |

(52) U.S. Cl.
CPC .......... *C12N 5/0641* (2013.01); *C12N 5/067* (2013.01); *C12N 5/0622* (2013.01); *C12N 5/0636* (2013.01); *C12N 5/0646* (2013.01); *C12N 5/0676* (2013.01); *C12N 2500/90* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/2303* (2013.01); *C12N 2501/2306* (2013.01); *C12N 2501/26* (2013.01); *C12N 2501/60* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/727* (2013.01); *C12N 2506/025* (2013.01); *C12N 2506/11* (2013.01); *C12N 2506/45* (2013.01); *C12N 2510/00* (2013.01)

(58) Field of Classification Search
CPC .......... C12N 2500/90; C12N 2501/115; C12N 2501/125; C12N 2501/145; C12N 2501/155; C12N 2501/165; C12N 2501/2303; C12N 2501/2306; C12N 2501/26; C12N 2501/60; C12N 2501/602; C12N 2501/603; C12N 2501/604; C12N 2501/605; C12N 2501/606; C12N 2501/608; C12N 2501/727; C12N 2506/025; C12N 2506/11; C12N 2506/45

See application file for complete search history.

(56) References Cited

U.S. PATENT DOCUMENTS

| | | |
|---|---|---|
| 5,843,780 A | 12/1998 | Thomson |
| 6,200,806 B1 | 3/2001 | Thomson |
| 7,029,913 B2 | 4/2006 | Thomson |
| 7,442,548 B2 | 10/2008 | Thomson et al. |
| 8,058,065 B2 | 11/2011 | Yamanaka et al. |
| 8,071,369 B2 | 12/2011 | Jaenisch et al. |
| 8,129,187 B2 | 3/2012 | Yamanaka et al. |
| 8,183,038 B2 | 5/2012 | Thomson et al. |
| 8,268,620 B2 | 9/2012 | Thomson et al. |
| 8,546,140 B2 | 10/2013 | Mack et al. |
| 8,691,574 B2 | 4/2014 | Mack |
| 8,741,648 B2 | 6/2014 | Rajesh et al. |
| 8,900,871 B2 | 12/2014 | Okita et al. |
| 9,127,256 B2 | 9/2015 | Fusaki et al. |
| 9,175,268 B2 | 11/2015 | Mack |
| 9,206,389 B2 | 12/2015 | Lazzari et al. |
| 9,206,394 B2 | 12/2015 | Nakauchi et al. |
| 2003/0211603 A1 | 11/2003 | Earp et al. |
| 2007/0077654 A1 | 4/2007 | Thomson et al. |
| 2009/0246875 A1 | 10/2009 | Yamanaka et al. |
| 2010/0210014 A1 | 8/2010 | Yamanaka |
| 2010/0279403 A1 | 11/2010 | Rajesh et al. |
| 2011/0104125 A1 | 5/2011 | Yu |
| 2011/0287538 A1 | 11/2011 | Fusaki et al. |
| 2012/0276636 A1 | 11/2012 | Yamanaka et al. |

(Continued)

FOREIGN PATENT DOCUMENTS

| | | |
|---|---|---|
| WO | WO 2006/050330 | 5/2006 |
| WO | WO 2007/069666 | 6/2007 |

(Continued)

OTHER PUBLICATIONS

Amit et al., "Clonally Derived Human Embryonic Stem Cell Lines Maintain Pluripotency and Proliferative Potential for Prolonged Periods of Culture," *Develop. Biol.*, 227:271-278, 2000.

(Continued)

*Primary Examiner* — Blaine Lankford
(74) *Attorney, Agent, or Firm* — Parker Highlander PLLC

(57) ABSTRACT

Provided herein are methods for the efficient in vitro maintenance, expansion, culture, and/or differentiation of pluripotent cells with disruption of the MeCP2 gene into various erythroid, myeloid, lymphoid, or endoderm lineages, particularly mature erythrocytes. The pluripotent cells may be maintained and differentiated under defined conditions; thus, the use of mouse feeder cells or serum is not required in certain embodiments for the differentiation of the precursor cells.

22 Claims, 67 Drawing Sheets
Specification includes a Sequence Listing.

(56) References Cited

U.S. PATENT DOCUMENTS

| | | |
|---|---|---|
| 2013/0210150 A1 | 8/2013 | Ban et al. |
| 2014/0273211 A1 | 9/2014 | Sluvkin et al. |
| 2014/0322808 A1 | 10/2014 | Keller et al. |
| 2015/0191697 A1 | 7/2015 | Stankewicz et al. |

FOREIGN PATENT DOCUMENTS

| | | |
|---|---|---|
| WO | WO 2010/008054 | 1/2010 |
| WO | WO 2010/099539 | 9/2010 |
| WO | WO 2012/029770 | 3/2012 |
| WO | WO 2012/109208 | 8/2012 |
| WO | WO 2016/115407 | 7/2016 |
| WO | WO 2017/070337 | 4/2017 |

OTHER PUBLICATIONS

Aoki et al., "Regualtion of DNA Demethylation during Maturation of CD4+ Native T Cells by the Conserved Noncoding Sequence 1," *J. Immunol.,* 182:7698-7707, 2009.

Ayllon et al., "The Notch ligand DLL4 specifically marks human hematoendothelial progenitors and regulates their hematopoietic fate," *Leukemia,* 29(8): 1741-1753, 2015.

Bauer et al., "Reawakening fetal hemoglobin: prospects for new therapies for the β-globin disorders," *Blood* 120(15): 2945-2953, 2012.

Bhatnagar, et al. "Genetic and pharmacological reactivation of the mammalian inactive X chromosome," *Proc. Natl. Acad. Sci. USA,* 2014.

Bird, A. "The methyl-CpG-binding protein MeCP2 and neurological disease," *Biochem. Soc. Trans.,* 36:575-583, 2008.

Carrio et al., "DNA methylation dynamics in muscle development and disease," *Front Aging Neurosci.,* 7(19):1-12, 2015.

Cheng et al., "Self-Renewing Endodermal Progenitor Lines Generated from Human Pluripotent Stem Cells," *Cell Stem Cell* 10(4): 371-384, 2012.

Chung et al., "Undifferentiated hematopoietic cells are characterized by a genome-wide undermethylation dip around the transcription start site and a hierarchical epigenetic plasticity," *Blood,* 114(24):4968-4978, 2009.

de Paz et al., "Circadian Cycle-Dependent MeCPZ and Brain Chromatin Changes," *PLoS,* 10(4)260123693, 2015.

Ditadi et al., "Human definitive haemogenic endothelium and arterial vascular endothelium represent distinct lineages," *Nature Cell Biol,* 7(5):580-591 and supporting information, 2015.

Doulatov et al., "Hematopoiesis: A Human Perspective," *Cell Stem Cell.* 10: 120-36, 2012.

Doulatov et al., "Revised map of the human progenitor hierarchy shows the origin of macrophages and dendritic cells in early lymphoid development," *Nature Immunol.,* 11:585-593, 2010.

Du Pré et al., "Circadian Rhythms in Cell Maturation," *Physiology,* 29:72-83, 2014.

Fuks et al., "The Methyl-CpG-binding Protein MeCPZ Links DNA Methylation to Histone Methylation," *J. Biol. Chem.,* 278(6):4035-4040, 2003.

Gama-Norton et al., "Notch signal strength controls cell fate in the haemogenic endothelium," *Nature Comm.,* 6(8510):1-12, 2015.

Gilsbach et al., "Dynamic DNA methylation orchestrates cardiomyocyte development, maturation and disease," *Nature Comm.,* 5(5288): 1-13, 2014.

Gouon-Evans et al., "BMP-4 is required for hepatic specification of mouse embryonic stem cell-derived definitive endoderm," *Nat. Biotechnol.,* 24(11):1402-1411, 2006.

Haddad et al., "Molecular characterization of early human T/NK and B-lymphoid progenitor cells in umbilical cord blood," *Blood* 104(13): 3918-3926, 2004.

Huijskens et al., "Technical Advance: Ascorbic acid induces development of double-positive T cells from human hematopoietic stem cells in the absence of stromal cells," *J. Leukocyte Biol.,* 96:1165-1175, 2014.

International Search Report and Written Opinion issued in corresponding PCT Application No. PCT/US2017/055353, dated Jan. 22, 2018.

Kennedy et al., "T Lymphocyte Potential Marks the Emergence of Definitive Hematopoietic Progenitors in Human Pluripotent Stem Cell Differentiation Cultures," *Cell Reports,* 2:1722-1735, 2012.

Kieusseian et al., "Immature hematopoietic stem cells undergo maturation in the fetal liver," *Development,* 139(19): 3521-3530, 2012.

Lappalainen et al. "A protocol for generating high numbers of mature and functional human mast cells from peripheral blood," *Clin. Experim. Allergy,* 37: 1404-1414, 2007.

Laranjeiro et al., "The Notch Ligand Delta-Like 4 Regulates Multiple Stages of Early Hemato-Vascular Development," *PLoS One,* 7(4):e34553, 1-13, 2012.

Lessard et al., "Comparison of DNA methylation profiles in human fetal and adult red blood cell progenitors," *Genome Med.,* 7(1):1-12, 2015.

Li et al., "Epigenetic Control of Circadian Clock Operation during Development," *Genetics Res. Int.,* 845429:1-8, 2012.

Ludwig et al. "Derivation of human embryonic stem cells in defined conditions," *Nature Biotech.,* (2):185-187, 2006.

Ludwig et al. "Feeder-independent culture of human embryonic stem cells," *Nature Methods,* 3(8):637-646, 2006.

Nguyen et al., "Global methylation profiling of lymphoblastoid cell lines reveals epigenetic contributions to autism spectrum disorders and a novel autism candidate gene, RORA, whose protein product is reduced in autistic brain," *FASEB J.,* 24:3037-3051, 2010.

Nostro et al., "Stage-specific signaling through TGFβ family members and WNT regulates patterning and pancreatic specification of human pluripotent stem cells," *Development* 138:861-871, 2011.

Notta et al., "Isolation of single human hematopoietic stem cells capable of long-term multilineage engraftment," *Science,* 333(6039):218-221, 2011.

Oberlin et al., "VE-cadherin expression allows identification of a new class of hematopoietic stem cells within human embryonic liver," *Blood* 116(22): 4444-4455, 2010.

Pandey et al., "A novel MeCP2 acetylation site regulates interaction with ATRX and HDAC1," *Genes Cancer,* 6(9-10):408-421, 2015.

Reubinoff et al., "Embryonic stem cell lines from human blastocysts: somatic differentiation in vitro," 2000.

Salvagiotto et al., "A Defined, Feeder-Free, Serum-Free System to Generate In Vitro Hematopoietic Progenitors and Differentiated Blood Cells from hESCs and hiPSCs," *PLoS One,* 6(3):e17829, 2011.

Schernthaner et al., "Expression, epitope analysis, and functional role of the LFA-2 antigen detectable on neoplastic mast cells," *Blood,* 98:3784-3792, 2001.

Scicchitano et al., "In vitro expansion of human cord blood CD36+ erythroid progenitors: Temporal changes in gene and protein expression," *Exp Hematol.* 31(9):760-769, 2003.

Sharghi-Namini et al., "Dll4-containing exosomes induce capillary sprout retraction in a 3D microenvironment," *Scientific Reports,* 4(4031):1-8, 2014.

Slukvin et al. In: *Directed Production of Specific Blood Lineages from Human Embryonic Stem Cells,* #33, ASCI/AAP Joint Meet. Posters, 2007.

Takahashi et al., "Induction of Pluripotent Stem Cells from Mouse Embryonic and Adult Fibroblast Cultures by Defined Factors," *Cell,* 131(5):861-872, 2007.

Tanaka et al., "Transcriptional regulation in pluripotent stem cells by methyl CpG-binding protein 2 (MeCPG2)," *Human Mol. Genetics,* 23(4):1045-1055, 2013.

Theisen et al., "Biochemical Analysis of Histone Deacetylase-independent Transcriptional Repression by MeCP2," *J. Biol. Chem.,* 288(10):7096-7104, 2013.

Vecsler et al., "MeCP2 deficiency down-regulates specific nuclear proteins that could be partially recovered by valproic acid in vitro," *Epigenetics,* 5(1):61-67, 2010.

Xi et al. "In Vitro Large Scale Production of Human Mature Red Blood Cells from Hematopoietic Stem Cells by Coculturing with Human Fetal Liver Stromal Cells," *Biomed Res. Int.,* 2013(807863):1-12, 2013.

(56) References Cited

OTHER PUBLICATIONS

Ying et al., "Conversion of embryonic stem cells into neuroectodermal precursors in adherent monoculture," 2003.
Yu et al. "Induced Pluripotent Stem Cell Lines Derived from Human Somatic Cells," *Science*, 318(5858):1917-1920, 2007.
Zhang et al., "DNA methylation dynamics during ex vivo differentiation and maturation of human dendritic cells," *Epigenetics Chromatin*, 7(21): 1-16, 2014.

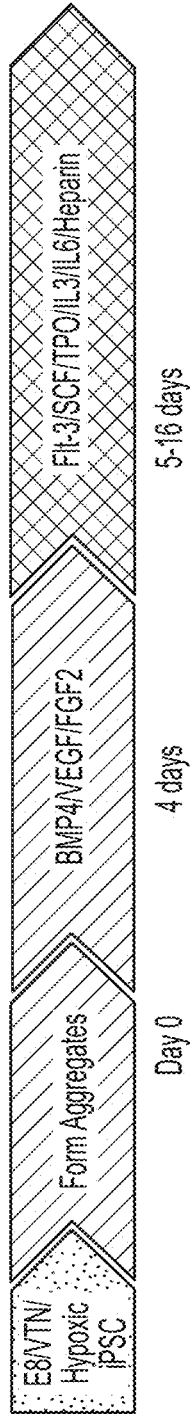
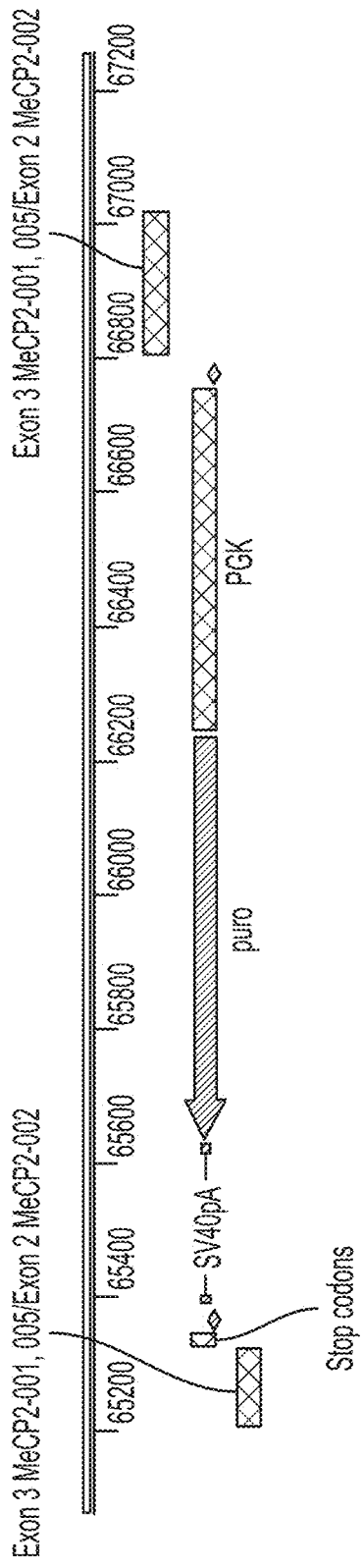
FIG. 1A
FIG. 1B

Methyl CpG Binding Domain
Engineering Site

```
MECP2_002   MAAAAAAAPSGGGGGGEEERLEEKSEDQDLQGLKDKPLKFKKVKKDKKEEKEGKHEPVQP
MECP2_005   ---------------MVAGMLGLREEKSEDQDLQGLKDKPLKFKKVKKDKKEEKEGKHEPVQP
MECP2_001   ---------------MVAGMLGLREEKSEDQDLQGLKDKPLKFKKVKKDKKEEKEGKHEPVQP
MECP2_008   ---------------MVAGMLGLREEKSEDQDLQGLKDKPLKFKKVKKDKKEEKEGKHEPVQP

MECP2_002   S XXX AHHSAEPAEAGKAETSEGSGSAPAVPEASASPKQRRSIIRDRGP MYDDPTLPEGWTRKL
MECP2_005   S XXX AHHSAEPAEAGKAETSEGSGSAPAVPEASASPKQRRSIIRDRGP MYDDPTLPEGWTRKL
MECP2_001   S XXX AHHSAEPAEAGKAETSEGSGSAPAVPEASASPKQRRSIIRDRGP MYDDPTLPEGWTRKL
MECP2_008   S XXX A-----------------------------------------------

MECP2_002   KQRKSGRSAGKYDVYLINPQGKAFRSKVELIAYFEKVGDTSLDPNDFD FTVTGRGSPSRR
MECP2_005   KQRKSGRSAGKYDVYLINPQGKAFRSKVELIAYFEKLQELAEAGDAP--------KGAA----
MECP2_001   KQRKSGRSAGKYDVYLINPQGKAFRSKVELIAYFEKVGDTSLDPNDFD FTVTGRGSPSRR
MECP2_008   ------------------------------------------------

MECP2_002   EQKPPKKPKSPKAPGTGRGRGRPKGSGTTRPKAATSEGVQVKRVLEKSPGKLLVKMPFQT
MECP2_005   ----PRDPRRPRQ----RVCR---------------------------
MECP2_001   EQKPPKKPKSPKAPGTGRGRGRPKGSGTTRPKAATSEGVQVKRVLEKSPGKLLVKMPFQT
MECP2_008   ------------------------------------------------

MECP2_002   SPGGKAEGGGATTSTQVMVIKRPGRKRKAEADPQAIPKKRGRKPGSVVAAAAAEAKKKAV
MECP2_005   ------------------------------------------------
MECP2_001   SPGGKAEGGGATTSTQVMVIKRPGRKRKAEADPQAIPKKRGRKPGSVVAAAAAEAKKKAV
MECP2_008   ------------------------------------------------

MECP2_002   KESSIRSVQETVLPIKKRKTRETVSIEVKEVVKPLLVSTLGEKSGKGLKTCKSPGRKSKE
MECP2_005   ------------------------------------------------
MECP2_001   KESSIRSVQETVLPIKKRKTRETVSIEVKEVVKPLLVSTLGEKSGKGLKTCKSPGRKSKE
MECP2_008   ------------------------------------------------

MECP2_002   SSPKGRSSSASSPPKKEHHHHHHHSESPKAPVPLLPPLPPPPPEPESSEDPTSPPEPQDL
MECP2_005   ------------------------------------------------
MECP2_001   SSPKGRSSSASSPPKKEHHHHHHHSESPKAPVPLLPPLPPPPPEPESSEDPTSPPEPQDL
MECP2_008   ------------------------------------------------

MECP2_002   SSSVCKEEKMPRGGSLESDGCPKEPAKTQPAVATAATAAEKYKHRGEGERKDIVSSSMPR
MECP2_005   ------------------------------------------------
MECP2_001   SSSVCKEEKMPRGGSLESDGCPKEPAKTQPAVATAATAAEKYKHRGEGERKDIVSSSMPR
MECP2_008   ------------------------------------------------

MECP2_002   PNREEPVDSRTPVTERVS
MECP2_005   ------------------
MECP2_001   PNREEPVDSRTPVTERVS
MECP2_008   ------------------
```

FIG. 1C

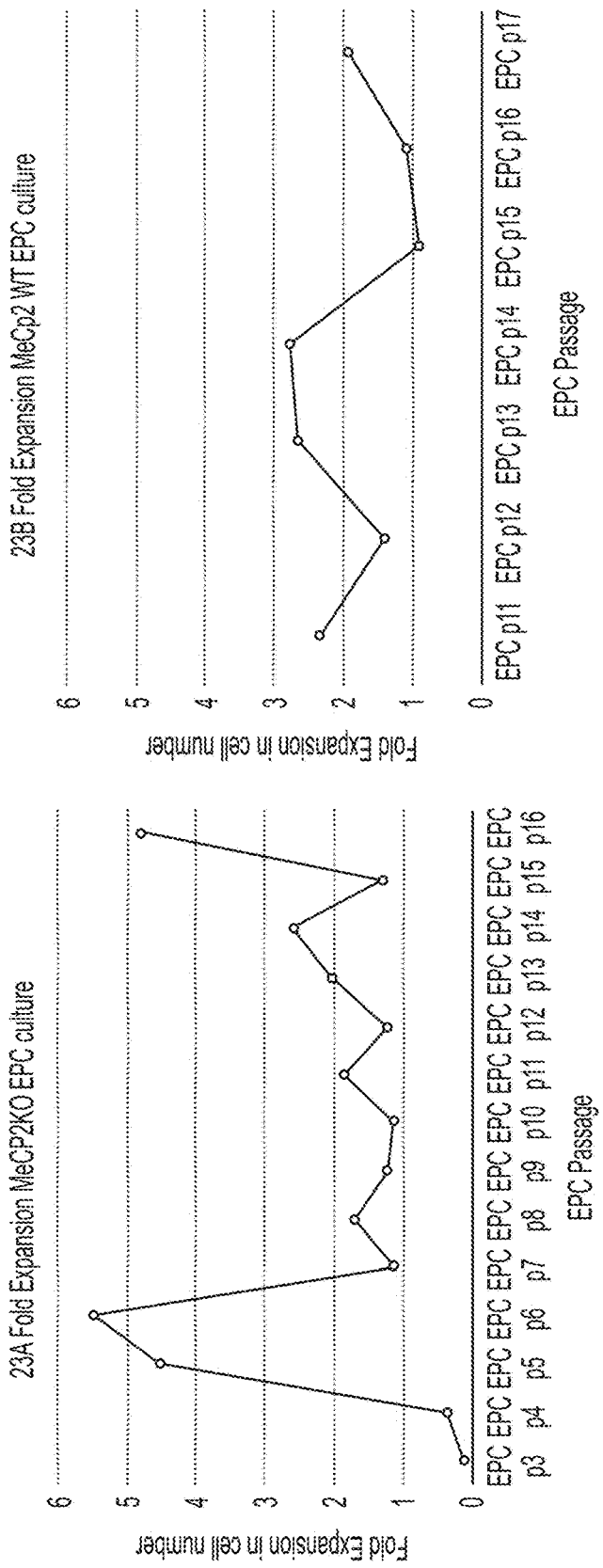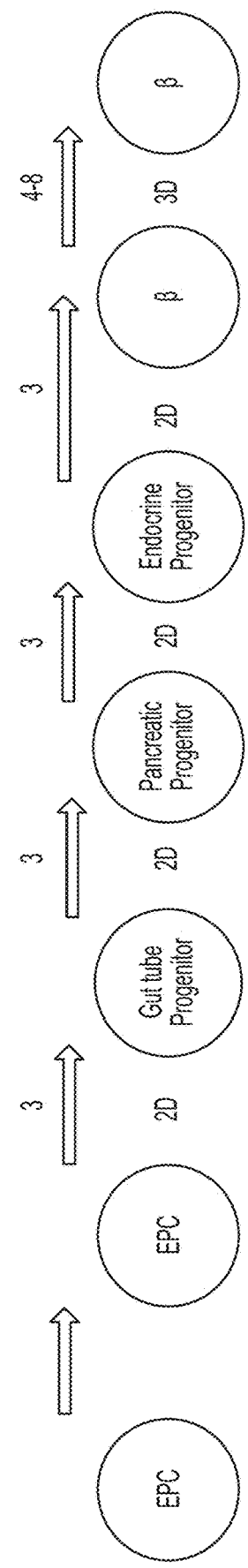
FIGS. 23A-23B
FIG. 23C

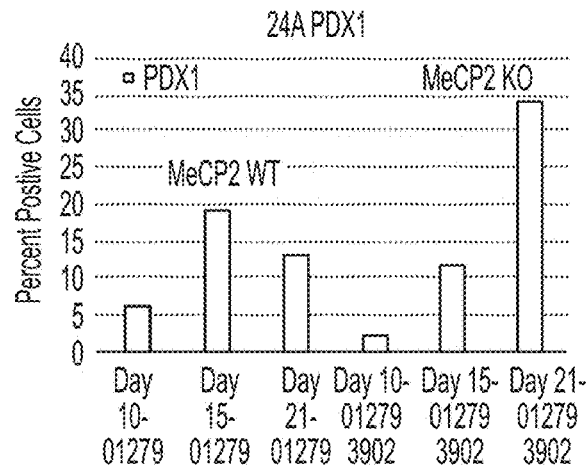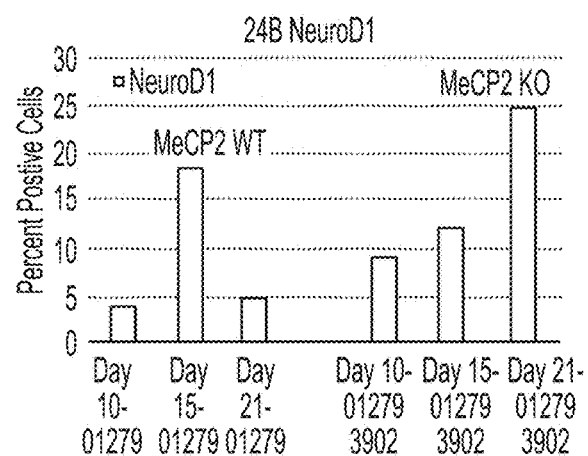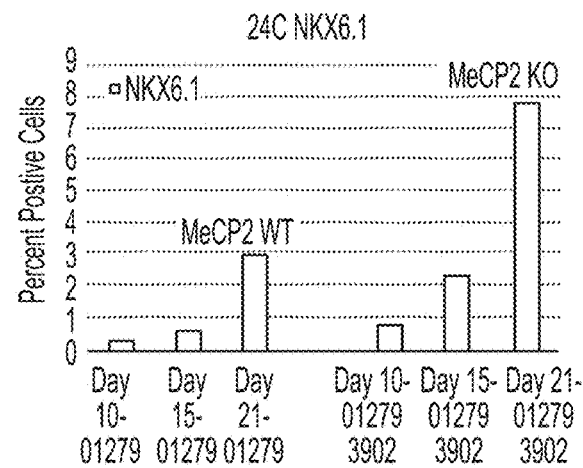
FIGS. 24A-C

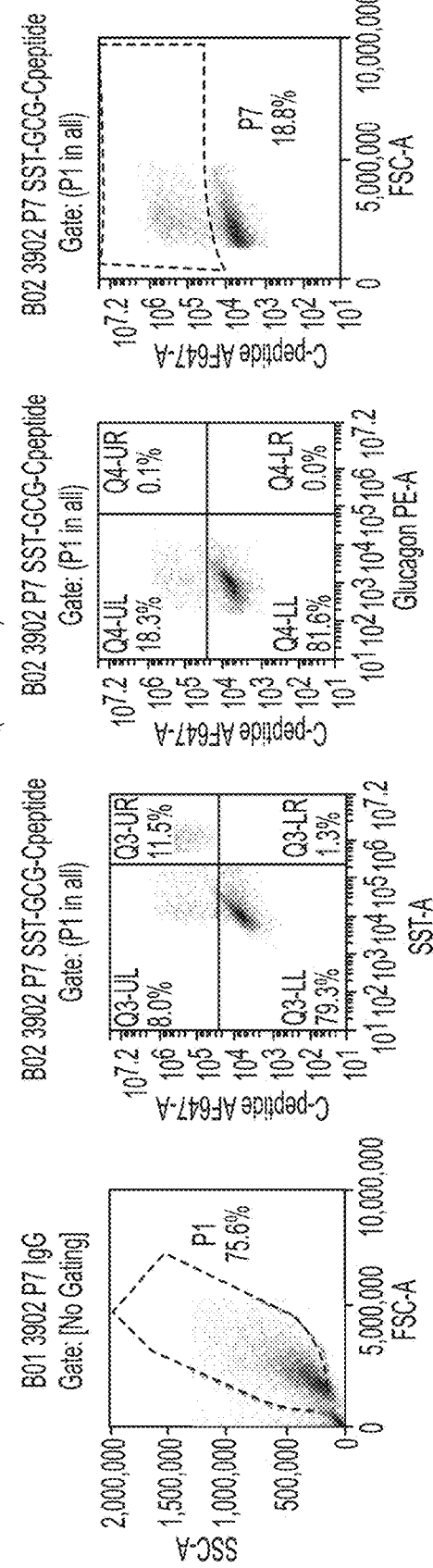
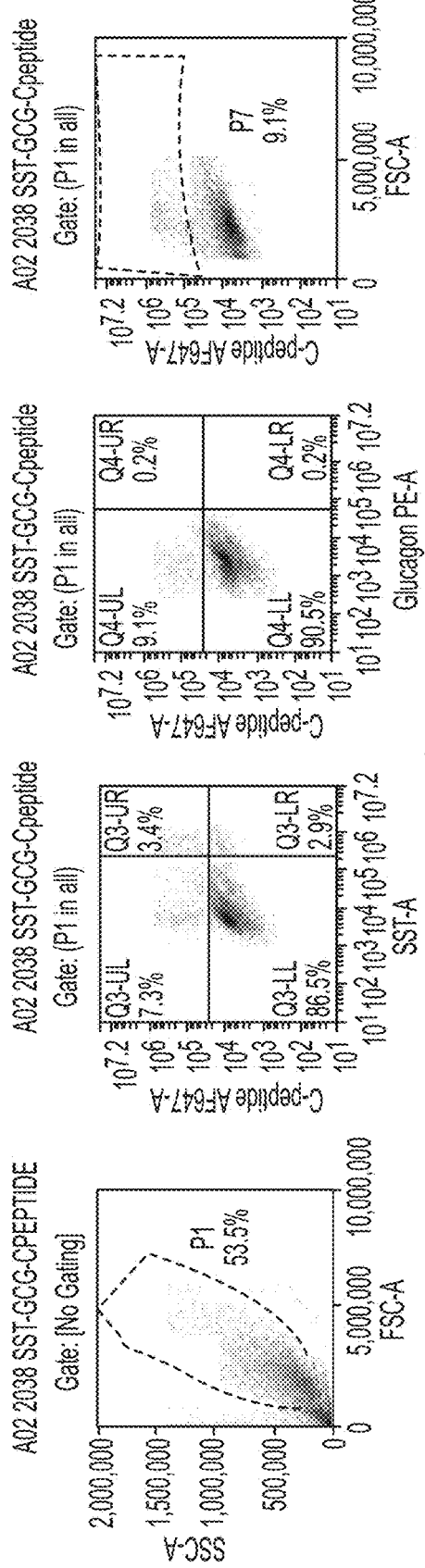
FIG. 26

GENERATING MATURE LINEAGES FROM INDUCED PLURIPOTENT STEM CELLS WITH MECP2 DISRUPTION

This application claims the benefit of U.S. Provisional Patent Application No. 62/404,430, filed Oct. 5, 2016, the entirety of which is incorporated herein by reference.

BACKGROUND OF THE INVENTION

1. Field of the Invention

The present invention relates generally to the field of molecular biology. More particularly, it concerns methods and compositions for the production of mesoderm, such as erythroid, myeloid, lymphoid cells, and endodermal lineages from precursor cells with MeCP2 disruption.

2. Description of Related Art

Due to the significant medical potential of hematopoietic precursor cells (HPCs), substantial work has been done to try to improve methods for the differentiation of HPCs to erythroid, myeloid and lymphoid lineages. In particular, in vitro models of human erythropoiesis are useful in studying the mechanisms of erythroid differentiation in normal and pathological conditions. Erythropoiesis defines the process of differentiation and proliferation from hematopoietic stem cells (HSCs) to mature red blood cells (RBCs). In adult humans, erythroid differentiation produces about $2 \times 10^{11}$ red cells per day. Erythroid lineage development requires a delicate balance between the opposing effects of proliferation-promoting factors and differentiation-inducing factors. Most of the commonly available in vitro assays of erythropoiesis are based on cell lines, such as murine MEL or human K562, HEL, and UT-7 cell lines. However, cell lines usually do not recapitulate the entire process of erythropoiesis, as many regulatory pathways have been altered during the transformation process that led to their immortalization. In addition, these models show only moderate proliferation or an absence of terminal differentiation and enucleation (Scicchitano et al., 2003).

Current methods to produce mature RBCs involve co-culturing erythroid progenitors with stromal cells such as human fetal liver stromal cells (hFLSCs) (Xi et al., 2013). However, the culture of HPCs with feeder cell lines presents the risk of unexpected transformations that have previously been associated with interspecies exposure during co-culture. Since one of the objectives of human HPC cultures is to create tissues which can ultimately be transplanted into a human body, it is highly desirable that the HPCs are not exposed to cells of another species or to a medium which has been used to culture cells of another species. Accordingly, a method that will permit the differentiation of human HPC cells into cells of the erythroid, myeloid or lymphoid lineage without a co-culture step of any kind, is of great interest in the continued development of techniques for the differentiation of human HPCs. Thus, there currently exists a clear need for methods of efficiently differentiating HPCs into erythroid, myeloid, lymphoid, and endoderm cells, such as mature erythrocytes, T cells, NK cells, T/NK cells, and microglia, without the use of feeder cells.

SUMMARY OF THE INVENTION

In one embodiment, there is provided a method of producing PSCs, such as induced pluripotent stem cells (iPSCs), with disrupted expression of Methyl-CpG Binding Protein 2 (MeCP2). In some aspects, the PSCs are engineered to disrupt the expression, activity, and/or function of MeCP2. In some aspects, engineering comprises genetic disruption of the MeCP2 gene. In particular aspects, genetic disruption comprises insertion of a stop codon prior to the methyl CpG binding domain of MeCP2. In certain aspects, the insertion of the stop codon comprises introduction of a DNA-binding domain. For example, the DNA-binding domain is a zinc finger, TALE or CRISPR DNA-binding domain. In some aspects, the PSCs, such as iPSCs, are mammalian, such as human iPSCs. In some aspects, disruption of MeCP2 results in alteration of methylation status of the iPSCs, such as to produce iPSCs with an enhanced ability to differentiate to mature lineages. In further aspects, the iPSCs with disruption of MeCP2, such as MeCP2 knockout (MeCP2KO), are differentiated to precursor cells, such as hematopoietic precursor cells (HPCs), definitive endoderm (DE) cells, or endodermal precursor cells (EPCs). These precursor cells may be further differentiated to mature lineage cells, such as erythrocytes, megakaryocytes, macrophages, microglia, T cells, NK cells, NK/T cells, B cells, β cells, dendritic cells, such as plasmacytoid dendritic cells, and hepatocytes.

In another embodiment, the present disclosure provide methods of generating cells of mature lineages, such as erythroid, myeloid and lymphoid lineage cells, from HPCs. In a further embodiment, there is provided a method of differentiating HPCs derived from PSCs into erythroid, lymphoid or myeloid cells comprising obtaining HPCs that exhibit disrupted MeCP2 and culturing the HPCs under conditions to promote erythroid differentiation, myeloid differentiation or lymphoid differentiation, thereby producing erythroid, myeloid or lymphoid cells.

In some aspects, the HPCs express a non-functional MeCP2 that has essentially no binding to methylated DNA. In certain aspects, the HPCs do not express MeCP2 at levels that are sufficient to effect MeCP2 DNA binding activity. In particular aspects, the MeCP2 is non-functional by virtue of a truncation or mutation in the MeCP2 gene.

In some aspects, obtaining HPCs that exhibit disrupted MeCP2 comprises contacting the HPCs with siRNA, shRNA or a small molecule inhibitor of MeCP2. In some aspects, a protein inhibitor is used to disrupt MeCP2. In certain aspects, the siRNA or shRNA disrupts both wild-type MeCP2 and mutant MeCP2. In other aspects, obtaining HPCs that exhibit disrupted MeCP2 comprises contacting PSCs with siRNA, shRNA or a small molecule inhibitor of MeCP2 and differentiating the PSCs to produce HPCs.

In certain aspects, obtaining HPCs that exhibit disrupted MeCP2 comprises engineering PSCs, such as iPSCs, to disrupt the expression, activity, and/or function of MeCP2 and differentiating the PSCs to produce HPCs. In some aspects, engineering comprises genetic disruption of the MeCP2 gene. In particular aspects, genetic disruption comprises insertion of a stop codon prior to the methyl CpG binding domain of MeCP2. In certain aspects, the insertion of the stop codon comprises introduction of a DNA-binding domain. For example, the DNA-binding domain is a zinc finger, TALE or CRISPR DNA-binding domain. In some aspects, the PSCs are mammalian pluripotent cells, such as human PSCs. In particular aspects, the PSCs are human iPSCs, such as virally reprogrammed or episomally reprogrammed iPSCs. For example, the iPSCs may be 9025, SONL, TiPS1E, Line A, Line H, or Line G iPSCs.

In certain aspects, differentiating the PSCs to produce HPCs comprises the sequential steps of: (a) culturing the PSCs in a first defined media comprising at least one growth factor; (b) culturing the cells in a second defined media comprising an amount of BMP4, VEGF, and bFGF sufficient to promote differentiation in a plurality of the cells; and (c) culturing the cells in a third defined media comprising an amount of IL-3, Flt3 ligand, and IL-6 sufficient to promote differentiation in a plurality of the cells, wherein a plurality of the PSCs are differentiated into HPCs. In some aspects, the HPCs express at least two markers from the group consisting of CD43, CD34, CD31, CD41, CD235 and CD45, such as positive for both CD43 and CD34. In some aspects, prior to step (a) the PSCs are adapted to hypoxia, such as for 5-10 passages.

In some aspects, HPCs that express CD34 and CD43 are cultured under conditions to promote lymphoid differentiation. In some aspects, the lymphoid cell is a T cell, B cell, NK cell, or T/NK cell.

In certain aspects, the method comprises culturing the cells at an atmospheric pressure of less than 20% oxygen. In particular aspects, the method comprises culturing the cells at an atmospheric pressure of less than 5% oxygen. In some aspects, a plurality of the pluripotent cells form embryoid bodies (EBs).

In certain aspects, the myeloid linage cell is a macrophage, mast cell, erythrocyte, megakaryocyte, platelet, dendritic cell, monocyte, basophil, eosinophil, neutrophil or polymorph nuclear granulocyte. In particular aspects, the erythroid lineage cell is an erythrocyte or erythroblast. In some aspects, the erythrocyte is enucleated. In certain aspects, the erythrocyte has expression of beta globin. In some aspects, the erythrocyte has a higher expression of beta globin as compared to the expression of epsilon globin and/or gamma globin. In particular aspects, disruption of MeCP2 results in production of erythrocytes which are more mature than erythrocytes derived from iPSCs with wild-type MeCP2, such as a lower expression of beta globin.

In some aspects, culturing the cells to promote erythroid differentiation comprises: (i) culturing the HPCs in a defined media comprising excyte and holo-transferrin to generate erythroblasts; and (ii) culturing the erythroblasts under expansion conditions to produce an enriched population of erythroid cells. In certain aspects, the defined media further comprises one or more cytokines. In some aspects, the one or more cytokines are selected from the group consisting of stem cell factor (SCF), Flt-3 ligand (Flt3L), thrombopoietin (TPO), Interleukin 3 (IL-3), and Interleukin 6 (IL-6). In certain aspects, the expansion conditions comprise culturing in a defined media essentially free of IL-3, IL-6 and TPO. In some aspects, step (i) and/or step (ii) comprises culturing for 1-2 weeks. In certain aspects, the enriched population of erythroid cells comprises greater than 70% erythroid cells, such as 71%, 72%, 73%, 74%, 75%, 76%, 77%, 78%, 79% erythroid cells. In some aspects, the enriched population of erythroid cells comprises greater than 80% erythroid cells, such as 85%, 90%, 91%, 92%, 93%, 94%, 95%, 96%, 97%, 98%, 99% or 100% erythroid cells. In some aspects, the erythroid cells express CD71, CD235a and/or CD36.

In some aspects, culturing the cells to promote myeloid differentiation comprises (a) culturing the HPCs in a defined microglia media comprising MCSF, TGFβ, and IL-34 for a sufficient period of time to generate microglia; and (b) maturing the microglia in defined microglia media further comprising CD200 and CXCL1, thereby producing a population of microglia. In some aspects, the population of microglia comprises at least 25%, such as 30%, 35%, 40%, 45%, 50%, 55%, 60%, 65%, or 70%, cells positive for IBA, P2RY, and/or TREM-2.

In some aspects, culturing the cells to promote lymphoid differentiation comprises: (i) culturing HPCs with expression of CD34 and/or CD43 in defined media on matrix-coated plates with Notch ligand; and (ii) maintaining the culture in the presence of one or more cytokines, thereby producing lymphoid cells. In some aspects, the cells are cultured at an atmospheric pressure of less than 5% oxygen. In some aspects, the defined media comprises ascorbic acid and/or nicotinamide. The concentration of ascorbic acid may be about 50 μM to 1 mM, such as 60 μM, 70 μM, 80 μM, 90 μM, 100 μM, 150 μM, or 200 μM. The nicotinamide may be present at a concentration of about 0.1 mM to 5 mM, such as 0.2 mM, 0.4 mM, 0.5 mM, 0.7 mM, 1 mM, 2 mM, 2.5 mM, 3 mM, 3.5 mM, 4 mM, or 4.5 mM. In certain aspects, the matrix is retronectin, collagen, laminin or fibronectin. In particular aspects, the Notch ligand is DLL4. For example, the DLL4 is DLL4:Fc chimera protein. In some aspects, the lymphoid cells have essentially no expression of CD4. In certain aspects, the lymphoid cells express one or more of the markers selected from the group consisting of CD8, CD7, CD45, CD5, and CD3. In some aspects, more than 5% of the lymphoid cells are positive for at least two of the markers. In certain aspects, more than 10% of the lymphoid cells are positive for at least two of the markers, such as 15%, 20%, 25%, 30% or greater.

Further embodiments provide methods of differentiating definitive endoderm (DE) cells derived from PSCs into endodermal cells comprising obtaining DE cells that exhibit disrupted Methyl-CpG Binding Protein 2 (MeCP2) and culturing the DEs under conditions to promote endodermal differentiation, thereby producing endodermal cells. In some aspects, culturing the DE cells under conditions to promote endodermal differentiation comprises differentiating the DE cells to EPCs. In particular aspects, the endoderm cells are beta cells, alpha cells, delta cells, or hepatocytes.

In certain aspects, the DE cells and/or EPCs express a non-functional MeCP2 that has essentially no binding to methylated DNA. In some aspects, the DE cells and/or EPCs do not express MeCP2 at levels that are sufficient to effect MeCP2 DNA binding activity. In some aspects, the MeCP2 is non-functional by virtue of a truncation, exon skipping, or mutation in the MeCP2 gene. In some aspects, obtaining DE cells or EPCs that exhibit disrupted MeCP2 comprises contacting the HPCs with siRNA, shRNA or a small molecule inhibitor of MeCP2. In certain aspects, the siRNA or shRNA disrupts both wild-type MeCP2 and mutant MeCP2.

In other aspects, obtaining DE cells or EPCs that exhibit disrupted MeCP2 comprises contacting PSCs with siRNA, shRNA, protein inhibitor, or a small molecule inhibitor of MeCP2 and differentiating the PSCs to produce DE cells or EPCs. In some aspects, obtaining DE cells or EPCs that exhibit disrupted MeCP2 comprises engineering PSCs to disrupt the expression, activity, and/or function of MeCP2 and differentiating the PSCs to produce DE cells or EPCs. In particular aspects, engineering comprises genetic disruption of the MeCP2 gene. In some aspects, genetic disruption comprises insertion of a stop codon prior to the methyl CpG binding domain of MeCP2. In specific aspects, the insertion of the stop codon comprises introduction of a DNA-binding domain. In some aspects, the DNA-binding domain is a zinc finger, TALE or CRISPR DNA-binding domain.

In particular aspects, the PSCs are iPSCs. In particular aspects, the PSCs are human iPSCs, such as virally reprogrammed or episomally reprogrammed iPSCs. For example, the iPSCs may be 9025, SONL, TiPS1E, Line A, Line H, or Line G iPSCs.

In some aspects, differentiating the PSCs to produce DE cells comprises the sequential steps of (a) culturing the PSCs in a media comprising MTG and Activin A; (b) culturing the cells in a media further comprising ascorbic acid, BMP4, bFGF, and VEGF; and (c) further culturing the cells in a media comprising BMP4, bFGF, Activin A, and VEGF for a period of time sufficient to produce DE cells. In additional aspects, the method further comprises differentiating the DE cells to EPCs, such as EPCs which express CXCR4/CD117 and/or CD34.

In certain aspects, culturing the DE cells under conditions to promote endoderm differentiation comprises culturing the DE cells in media comprising Activin A, BMP4, TGFβ, EGF, VEGF, and HGF for a period of time sufficient to produce a population of β cells. In some aspects, the population of β cells comprise at least 25%, such as 26%, 27%, 28%, 29%, 30%, 31%, 32%, 33%, 34%, 35%, 36%, 37%, 38%, 39%, 40%, or higher, PDX1-positive cells. In certain aspects, the population of β cells comprise at least 20%, such as 21%, 22%, 23%, 24%, 25%, 26%, 27%, 28%, 29%, 30%, 31%, 32%, 33%, 34%, 35%, or higher, NeuroD1-positive cells. In some aspects, the population of β cells comprise at least 5%, such as 6%, 7%, 8%, 9%, 10%, 11%, 12%, 13%, 14%, 15%, 16%, 17%, 18%, 19%, 20%, or higher, NKX6.1-positive cells.

In some aspects, culturing the DE cells under conditions to promote endoderm differentiation comprises (a) culturing the DE cells in media comprising BMP4, bFGF, EGF, VEGF, HGF, Dex, DMSO, and/or FGF-10 under hypoxic conditions; (b) further culturing the cells in media comprising DAPT and Vitamin K; and (c) differentiating the cells in media essentially free of DAPT and Vitamin K for a period of time sufficient to produce a population of hepatocytes. In particular aspects, the population of hepatocytes comprises at least 20%, such as 21%, 22%, 23%, 24%, 25%, 26%, 27%, 28%, 29%, 30%, 31%, 32%, 33%, 34%, 35%, or higher cells positive for albumin.

Further provided herein are compositions comprising an iPSC with MeCP2 disruption, precursor cells derived from the MeCP2KO iPSCs including HPCs, DE cells, and EPCs. Also provided herein are compositions comprising cells of mature lineages derived from the MeCP2KO iPSCs including erythrocytes, megakaryocytes, macrophages, microglia, T cells, NK cells, NK/T cells, B cells, β cells, dendritic cells, such as plasmacytoid dendritic cells, and hepatocytes. Also provided herein are methods of using the MeCP2KO iPSCs, HPCs, DE cells, EPCs, erythrocytes, megakaryocytes, macrophages, microglia, T cells, NK cells, NK/T cells, B cells, β cells, dendritic cells, such as plasmacytoid dendritic cells, and hepatocytes for in vitro assays and therapeutics including stable transplantation in vivo, screening of compounds in vitro, and elucidating the mechanisms of diseases and injuries.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1C: (1A) Schematic representation of 3D HPC differentiation process using iPSCs adapted to feeder free growth on Matrigel or Vitronectin in the presence of E8 media and hypoxic conditions. The first stage of HPC differentiation is driven by BMP4, VEGF and FGF for 4 days and the second stage of differentiation is driven by placing cells in media containing Heparin, SCF, TPO, Flt-3 Ligand, IL-3 and IL-6. (1B) Engineering strategy to generate a MeCP2KO in male iPSC cell line 01279 to create 9006 (01279.107.3902). (1C) Depiction of the amino acid alignment of MeCP2 variants 001 (SEQ ID NO: 1), 002 (SEQ ID NO: 2), 005 (SEQ ID NO: 3) and 008 (SEQ ID NO: 4) derived from 01279 iPSCs transfected with MeCP2 TALENS and Donor plasmid p1553. All variants (001, 002, 005 and 008) do not code for a Methyl CpG binding domain.

(MeCP2KO) were stained with wright stain. The presence of enucleated erythrocytes were visually captured in the cytospins.

Figure 9:
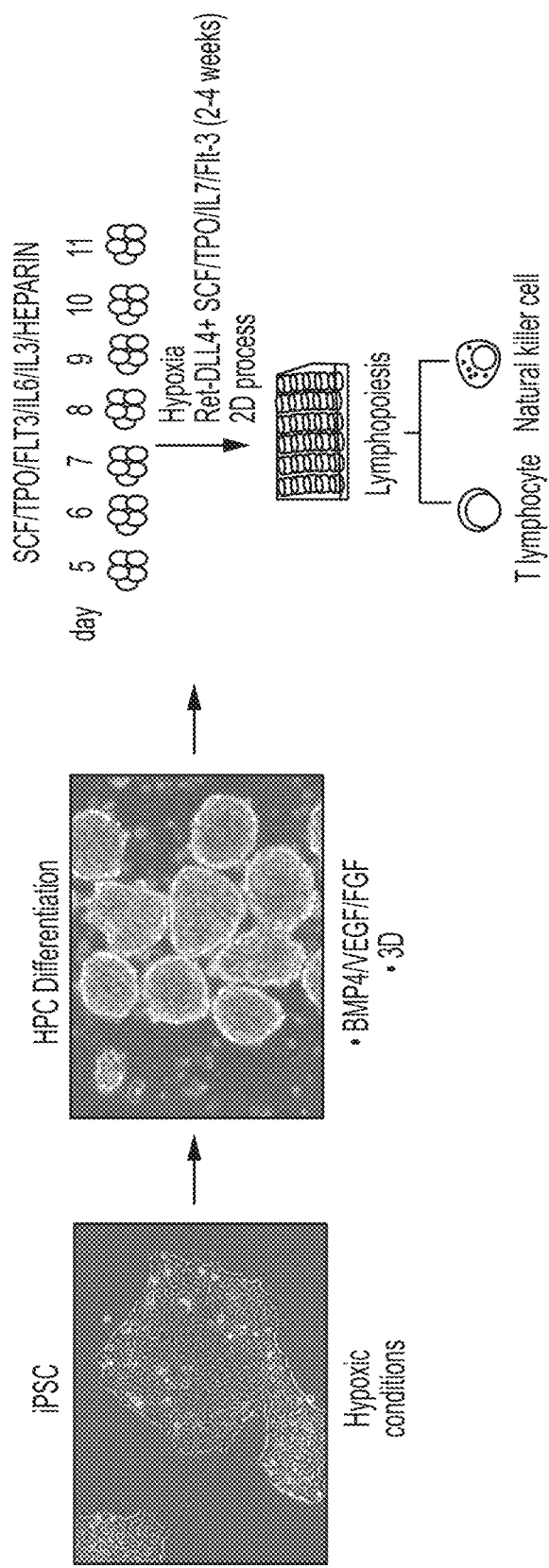

FIG. 9: Schematic representation of lymphoid differentiation. HPCs harvested from day 5-11 were plated on non-tissue culture treated plates at a density of 25 K/cm$^2$ in the presence of SCF, TPO, IL-7, and Flt-3 ligand for 2-4 weeks. The emergence of T cells, NK cells and NK/T cells were quantified by flow cytometry.

Figures 10A, 10B, 10C:
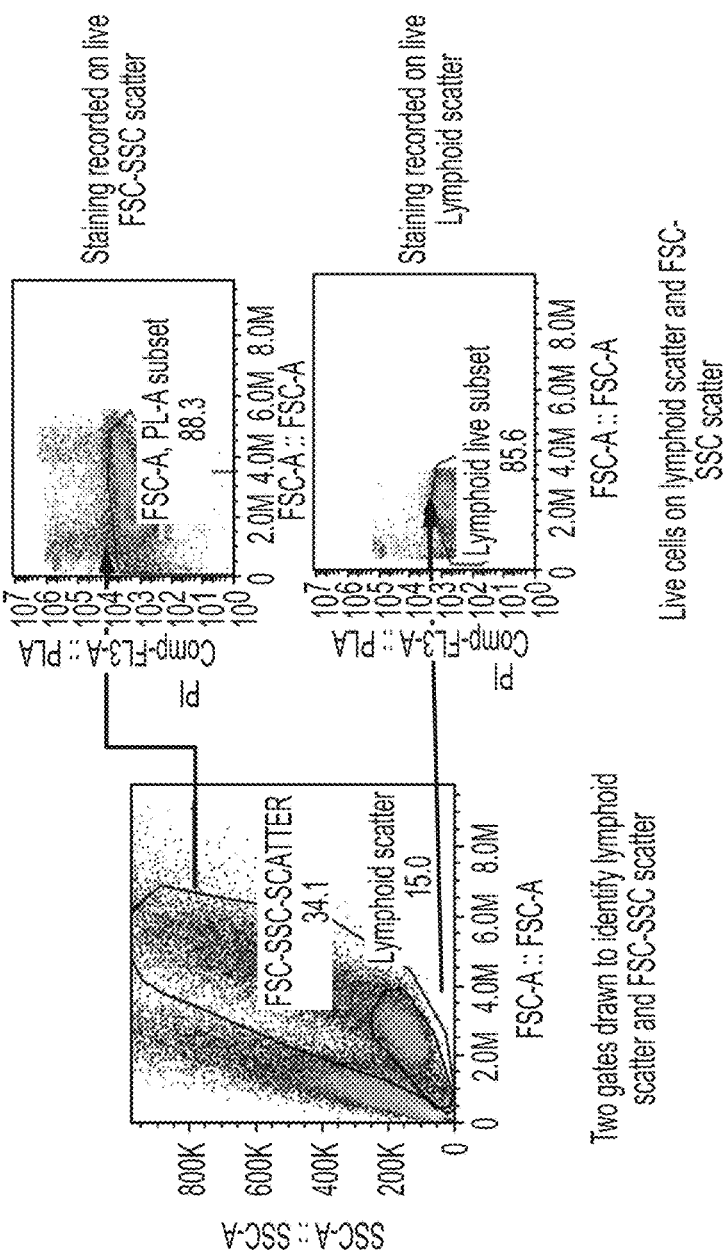

FIGS. 10A-10C: Gating strategy for identifying lymphoid cells generated in vitro. (10A) General scatter profile of lymphocytes from adult human peripheral blood. (10B) Scatter profile of lymphoid cells at day 18 of differentiation. The FSC-SSC gate and the lymphoid gate are illustrated. (10C) Gating live cells within the FSC-SSC scatter and lymphoid scatter using propidium iodide.

Figure 11A:
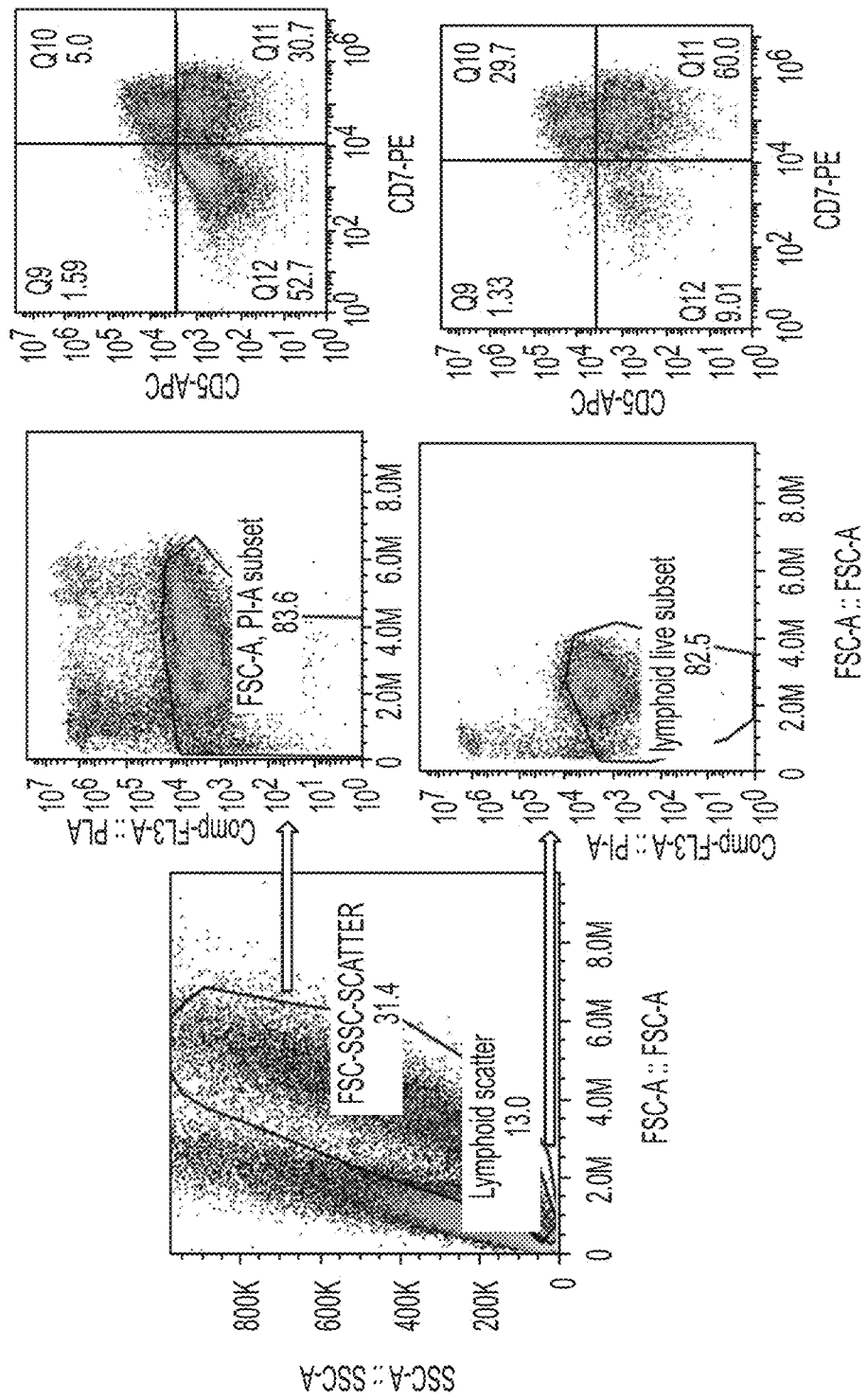
Figure 11B:
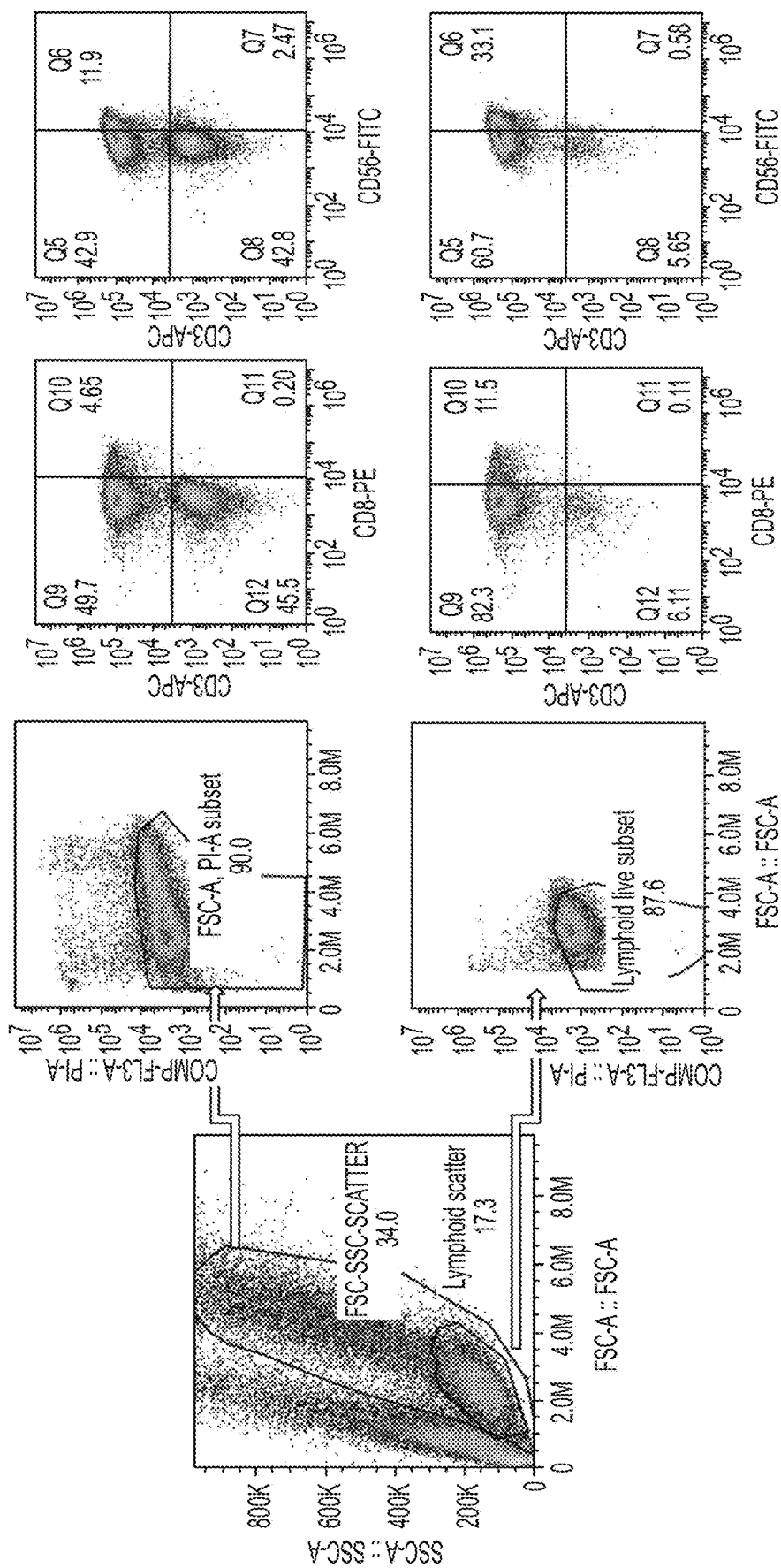

FIGS. 11A-11B: (11A) Gating strategy for identifying lymphoid cells generated in vitro. A scatter profile of lymphoid cells at day 18 of differentiation is shown. The FSC-SSC gate and the lymphoid gate are illustrated. Live cells were gated within the FSC-SSC scatter and lymphoid scatter using propidium iodide followed by staining for CD7 and CD5 positive cells by flow cytometry. (11B) Live cells were gated within the FSC-SSC scatter and lymphoid scatter using propidium iodide followed by staining for CD3, CD8 and CD56 positive cells by flow cytometry.

Figures 12A, 12B:
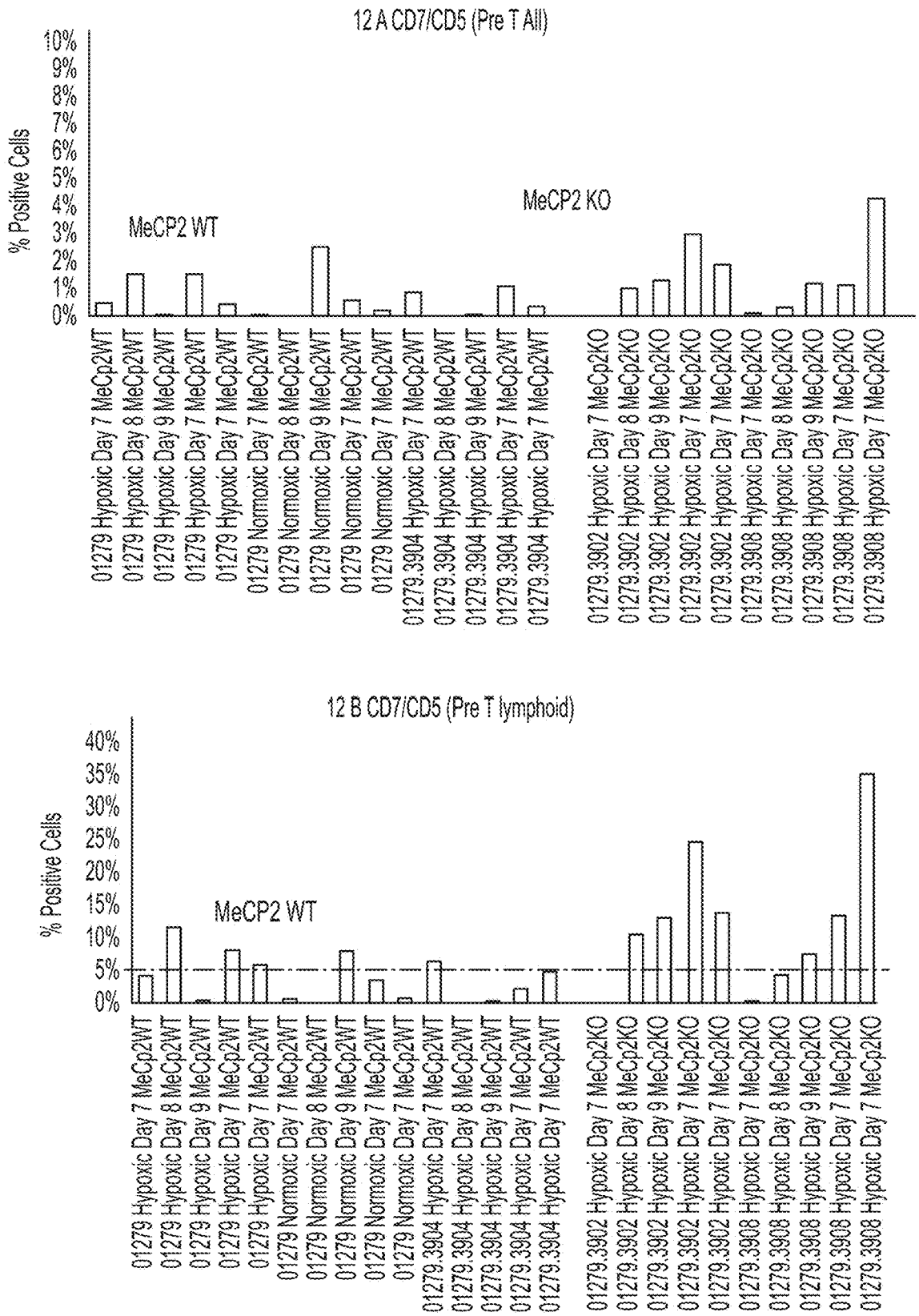

FIGS. 12A-12B: Percentage of double positive CD7$^+$/CD5$^+$ Pre T (12A) and Pre T lymphoid (12B) cells differentiated from day 7-11 HPCs placed on Ret-DLL4 coated plates to initiate lymphoid differentiation at a density of 25 k/cm$^2$ maintained under hypoxic conditions or normoxic conditions.

Figures 13A, 13B, 13C:
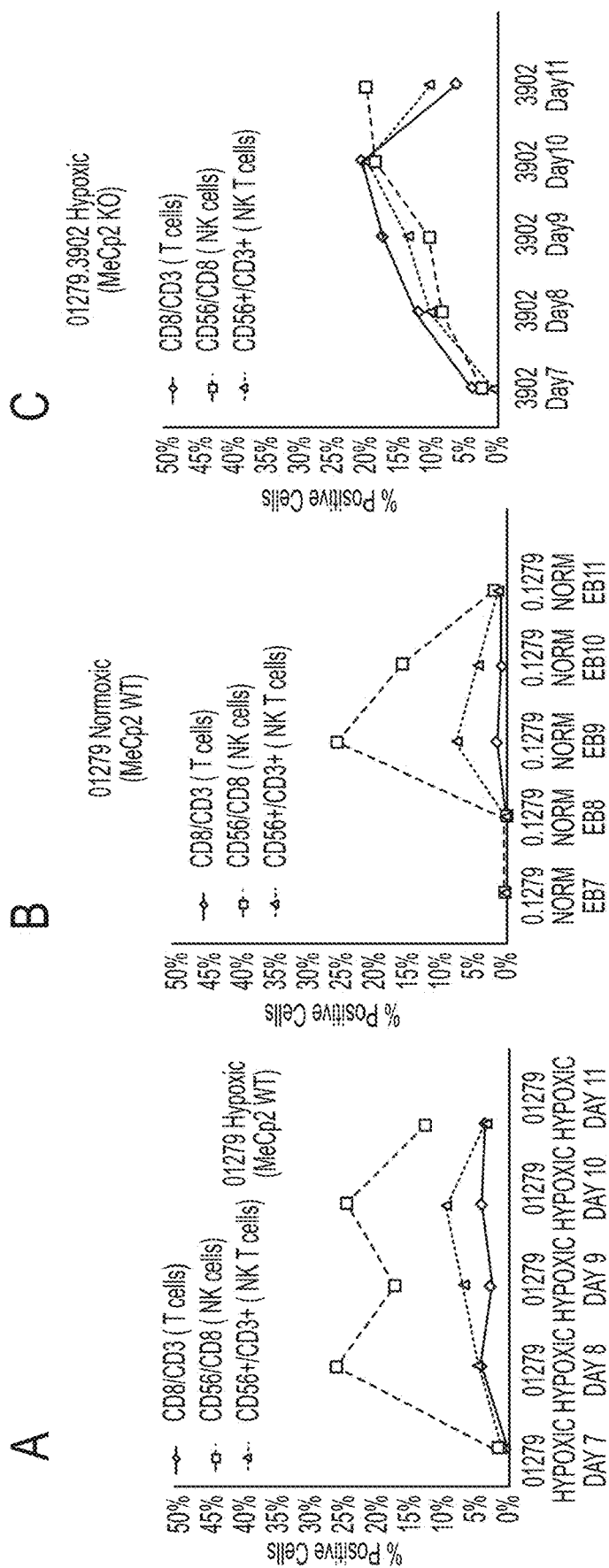

FIGS. 13A-13C: Quantification of Pre T and Pre NK cells harvested on day 7-11 of HPC differentiation and placed on Ret-DLL4 coated plates to initiate lymphoid differentiation at a density of 25 k/cm$^2$. The percentages of CD8$^+$CD3$^+$ (T cells), CD56$^+$/CD8$^+$/CD3$^+$ (NK cells), and CD56$^+$/CD3$^+$ (NK/T cells) in 01279 (MeCP2WT) cells maintained under hypoxic conditions (13A) or normoxic conditions (13B) as well as 01279.107.3902 cells (MeCP2K0) under hypoxic conditions (13C) was determined.

Figures 14A, 14B:
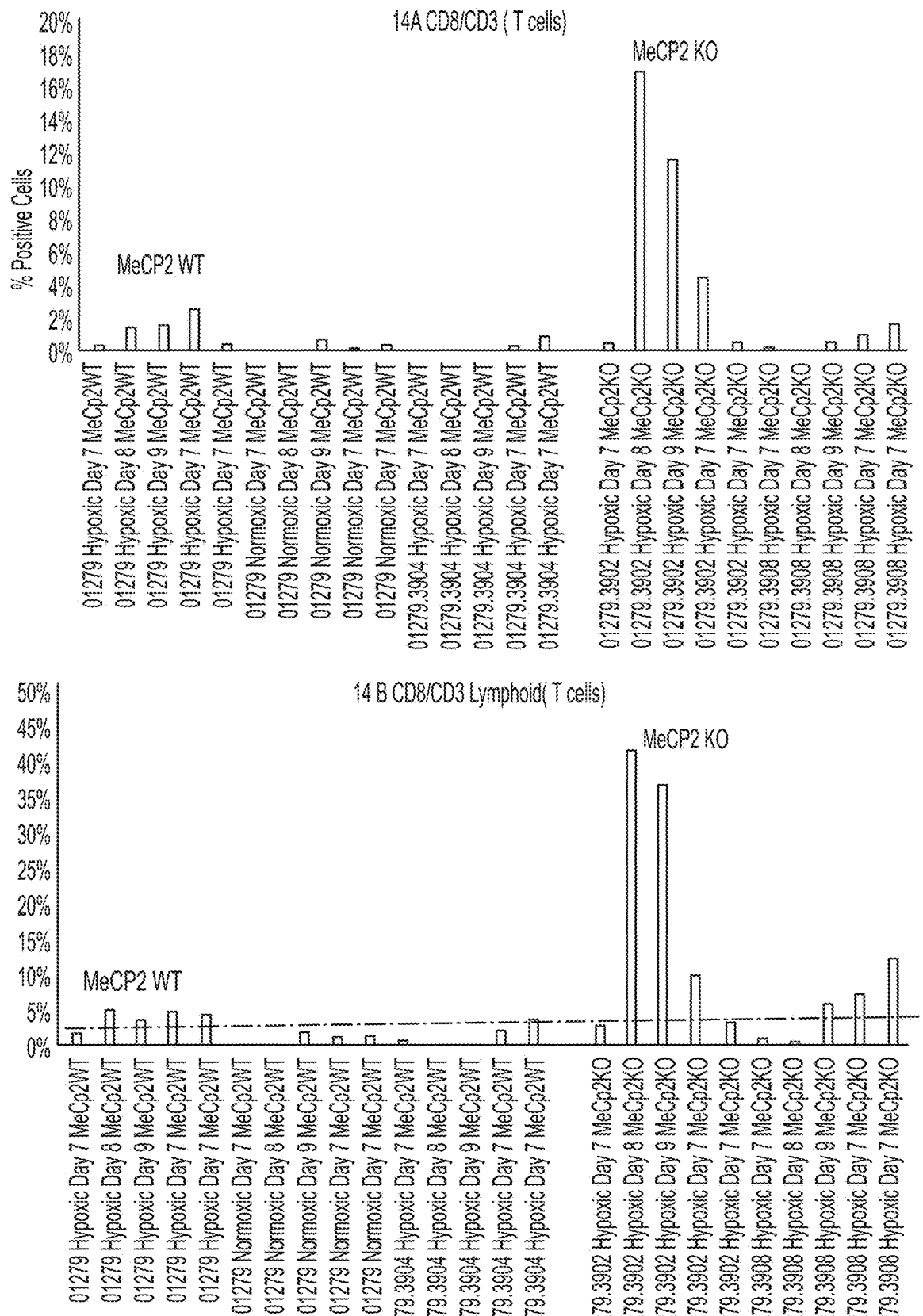

FIGS. 14A-14B: Quantification of T (CD3$^+$/CD8$^+$) cells on day 7-11 of HPC of differentiation and placed on Ret-DLL4 coated plates to initiate lymphoid differentiation at a density of 25 k/cm$^2$. The percentages of double positive CD8$^+$/CD3$^+$ under the all live FSC-SSC gate (14A) and lymphoid gate (14B) was determined for iPSC clones containing MeCP2WT and MeCP2KO status.

Figure 15A:
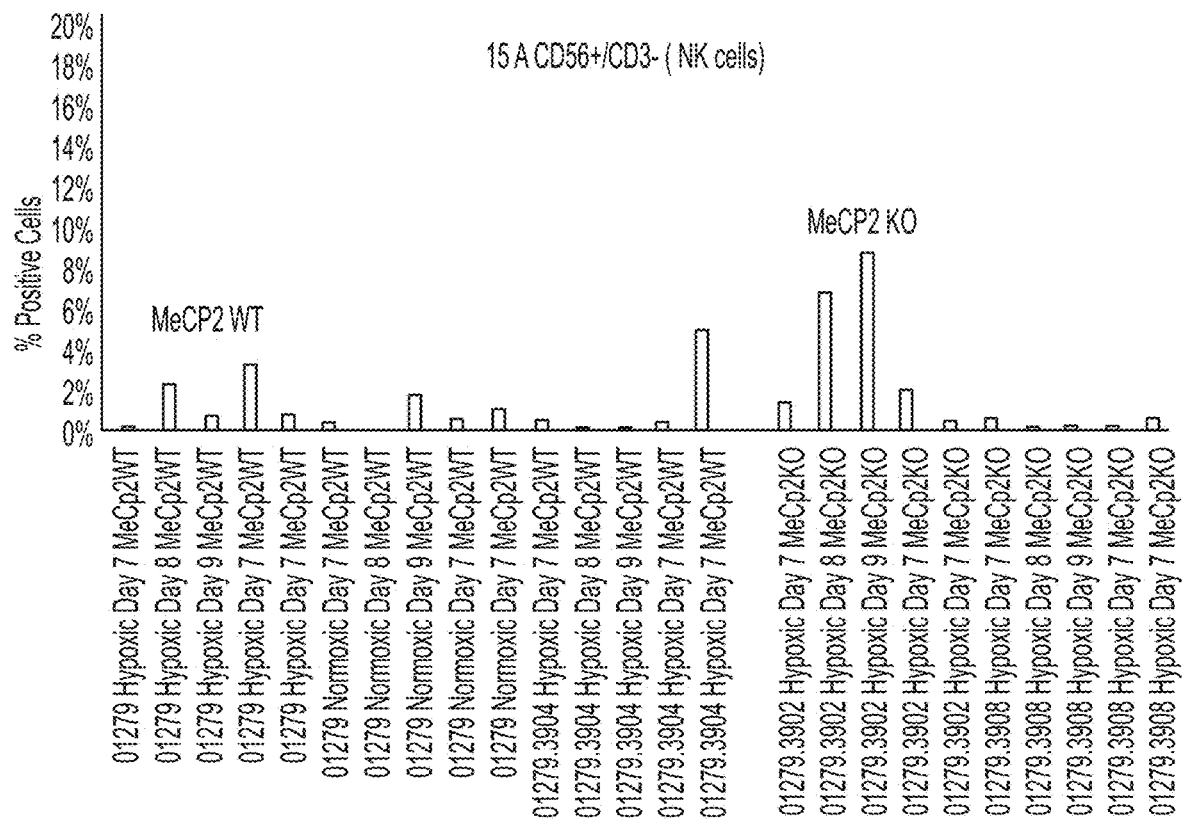
Figure 15B:
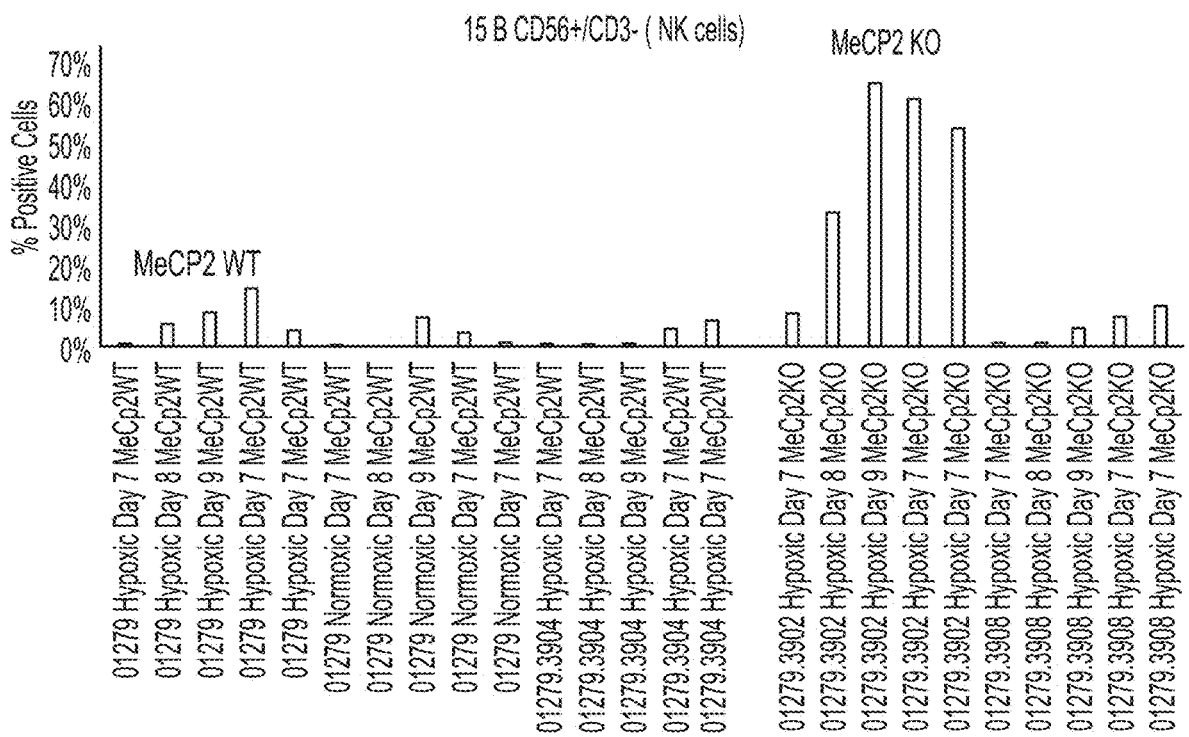

FIGS. 15A-15B: Quantification of NK (CD3$^-$/CD56$^+$) cells on day 7-11 of HPC of differentiation and placed on Ret-DLL4 coated plates to initiate lymphoid differentiation at a density of 25 k/cm$^2$. The percentages of CD56$^+$/CD3$^-$ under the all live FSC-SSC gate (14A) and lymphoid gate (15B) was determined for iPSC clones containing MeCP2WT and MeCP2KO status.

Figures 16A, 16B:
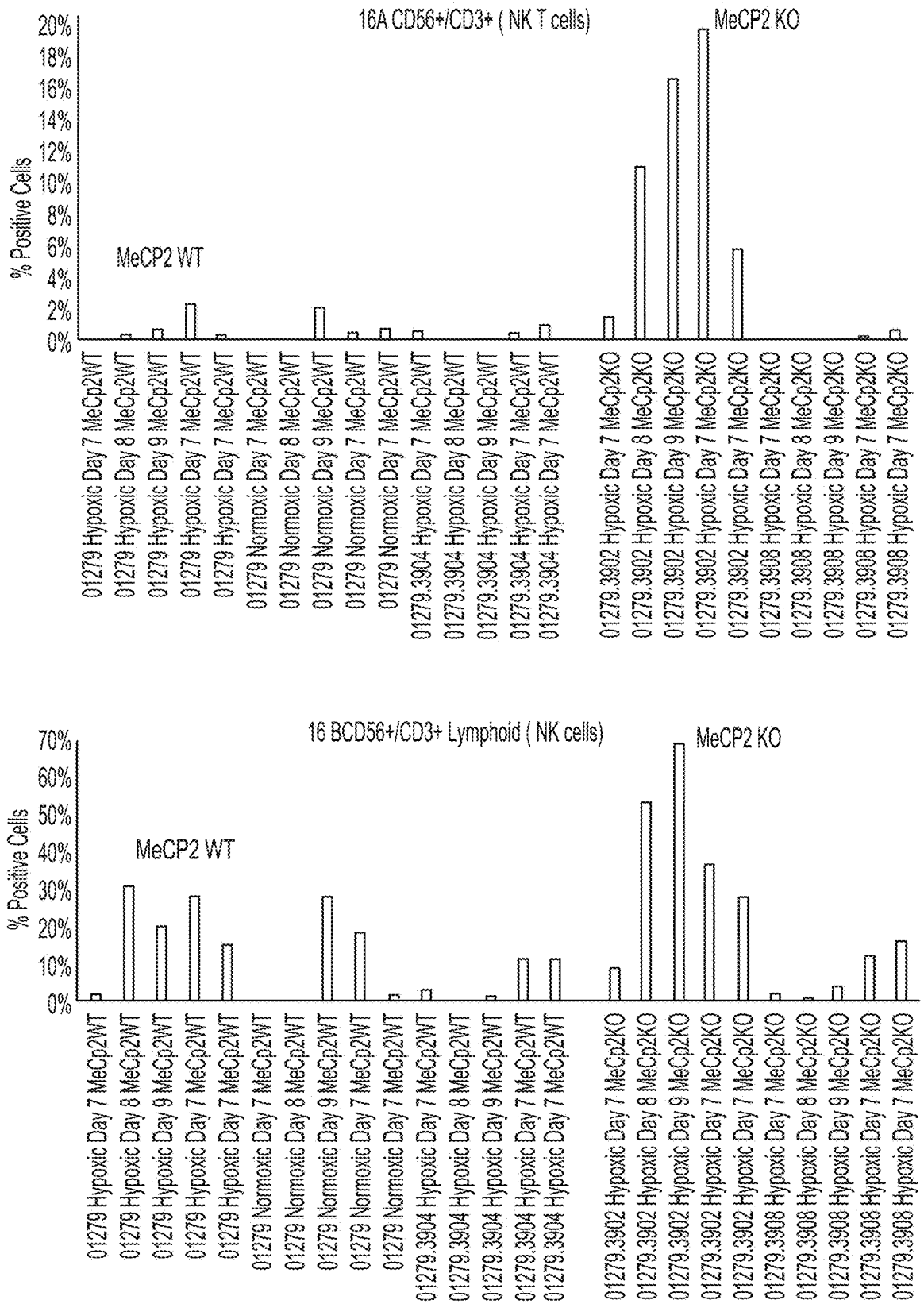

FIGS. 16A-16B: Quantification of NK/T (CD3$^+$/CD56$^+$) cells on day 7-11 of HPC of differentiation and placed on Ret-DLL4 coated plates to initiate lymphoid differentiation at a density of 25 k/cm$^2$. The percentages of double positive CD56$^+$/CD3$^+$ under the all live FSC-SSC gate (16A) and lymphoid gate (16B) was determined for iPSC clones containing MeCP2WT and MeCP2KO status.

Figure 17A:
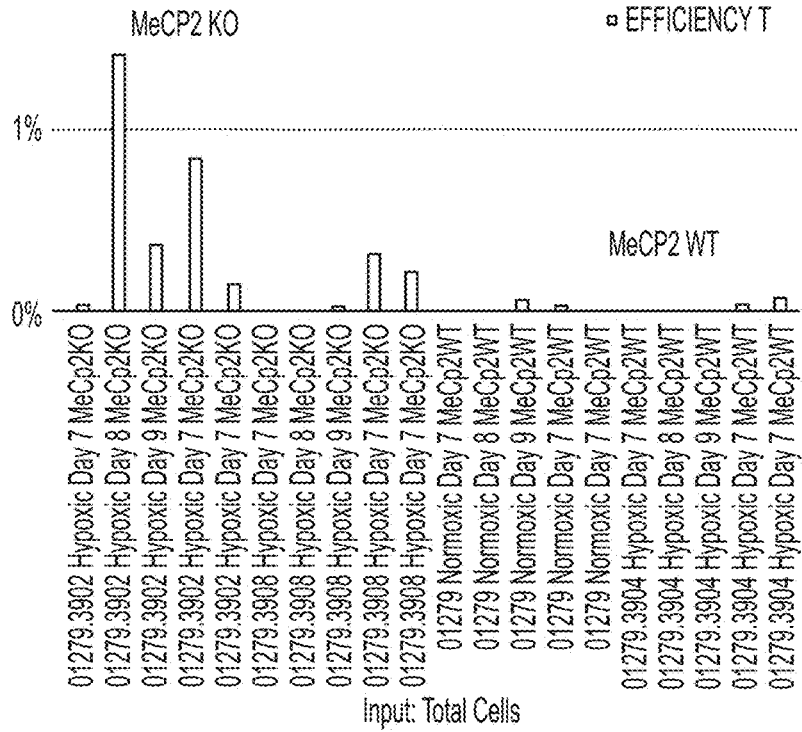
Figure 17B:
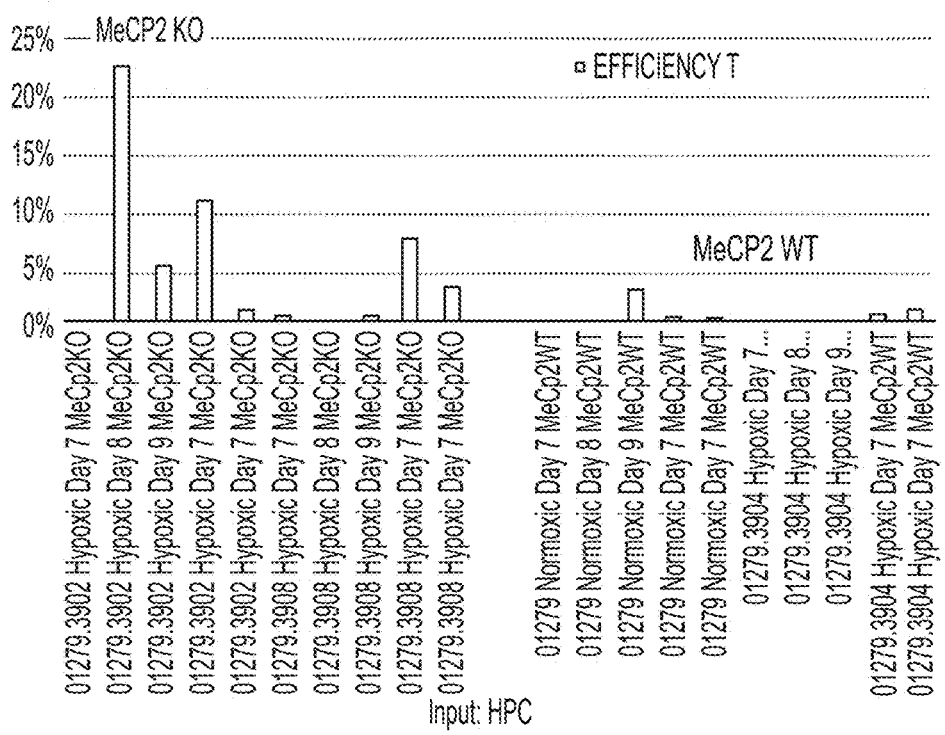

FIGS. 17A-17B: Measuring efficiency of the differentiation process. iPSC containing MeCP2WT and MeCP2KO were harvested on day 7-11 of HPC differentiation and placed on Ret-DLL4 coated plates to initiate lymphoid differentiation at a density of 25 k/cm$^2$. The cells were stained for the surface expression of CD8 and CD3. The percentage of cells were quantified by flow cytometry under FSC-SSC gate and the lymphoid scatter gate. Since the input number of cells and the total number of viable cells at the end of 16 days of differentiation was known the absolute number of T (CD3$^+$/CD8) was determined. The efficiency of the process is calculated by the ratio of absolute number of a cell type/input number of total cells (17A) or by the ratio of absolute number of a cell type/input number of (CD43$^+$/CD34$^+$) HPCs (17B).

Figures 18A, 18B:
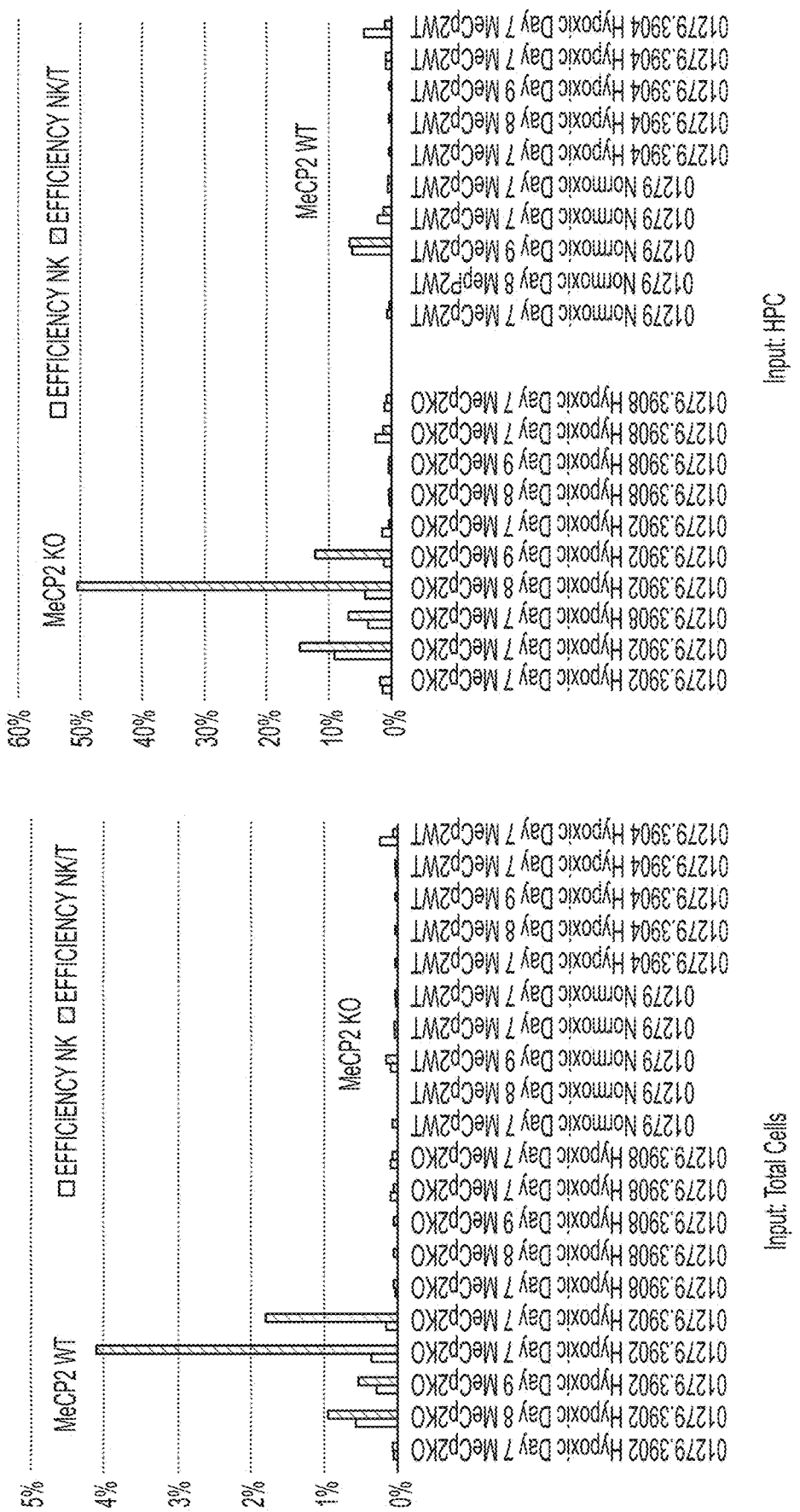
Figures 19A, 19B, 19C, 19D:
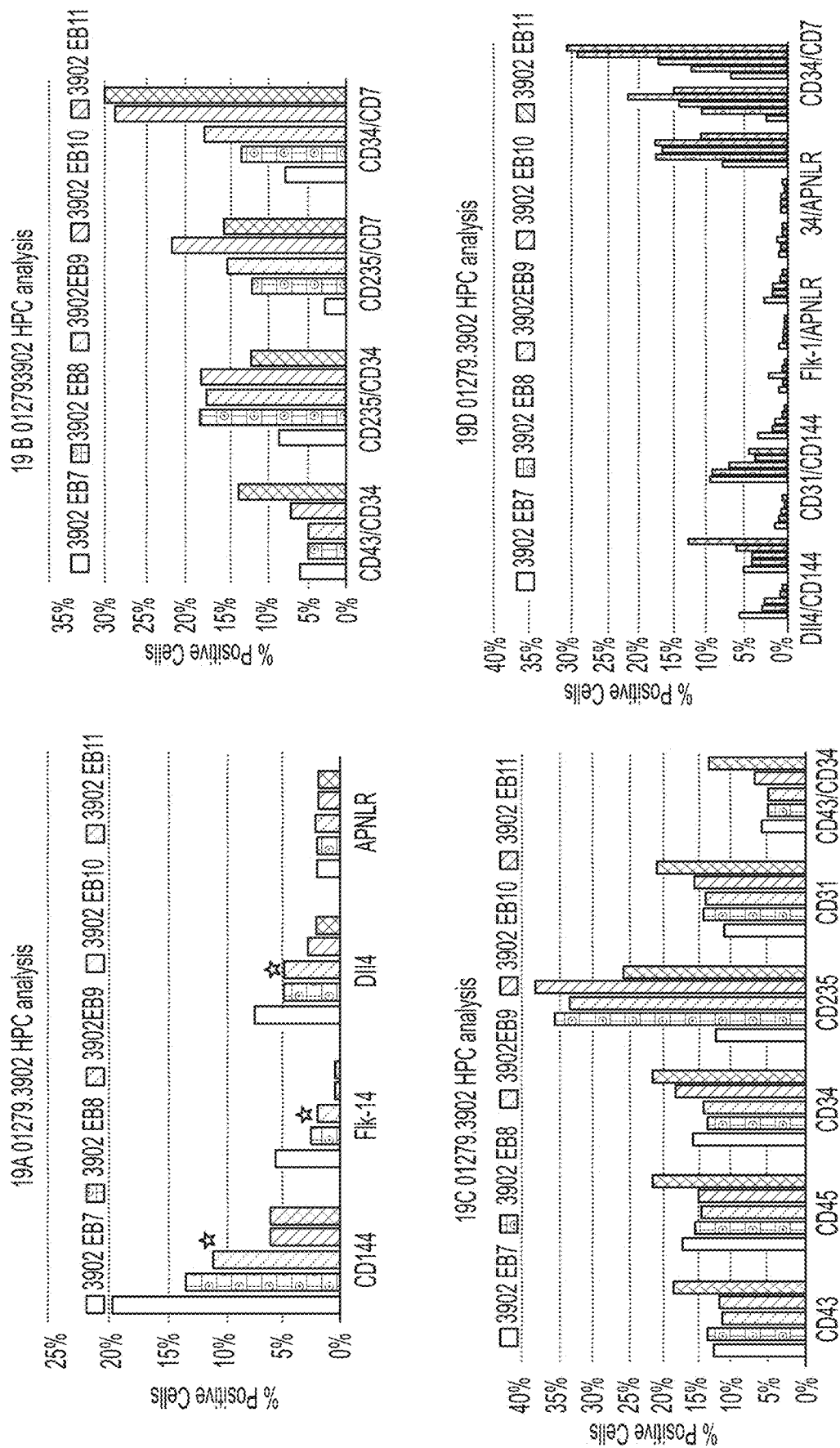

FIGS. 18A-18B: Measuring efficiency of the differentiation process. iPSC containing MeCP2WT and MeCP2KO were harvested on day 7-11 of HPC differentiation and placed on Ret-DLL4 coated plates to initiate lymphoid differentiation at a density of 25 k/cm$^2$. The cells were stained for the surface expression of CD56, CD8, and CD3. The percentage of cells were quantified by flow cytometry under FSC-SSC gate and the lymphoid scatter gate. Since the input number of cells and the total number of viable cells at the end of 16 days of differentiation was known the absolute number of NK/T (CD3$^+$/CD56$^+$) and NK (CD56$^+$/CD3$^-$) was determined. The efficiency of the process is calculated by the ratio of absolute number of a cell type (NK/T, or NK)/input number of total cells (18A) or by the ratio of absolute number of a cell type/input number of (CD43$^+$/CD34$^+$) HPCs (18B).

FIGS. 19A-19D: Determining the phenotypic signature of a lymphoid progenitor. HPCs generated from MeCP2KO and MeCP2WT iPSCs. HPCs were stained at different stages of differentiation for the following markers: CD43FITC/CD45PE/CD34APC, CD235FITC/CD7PE/CD34APC, CD31FITC/DLL4PE/CD144APC, CD34FITC/DLL4 PE/APNLR APC, FLK-1FITC/CD34 PE/APNLR APC, CD56 FITC/CD34PE/CD44 APC. The percentages of expression profile for these various markers in iPSC 01279.107.3902 (MeCP2KO) is outlined in 19A, 19B, 19C, 19D.

Figure 20:
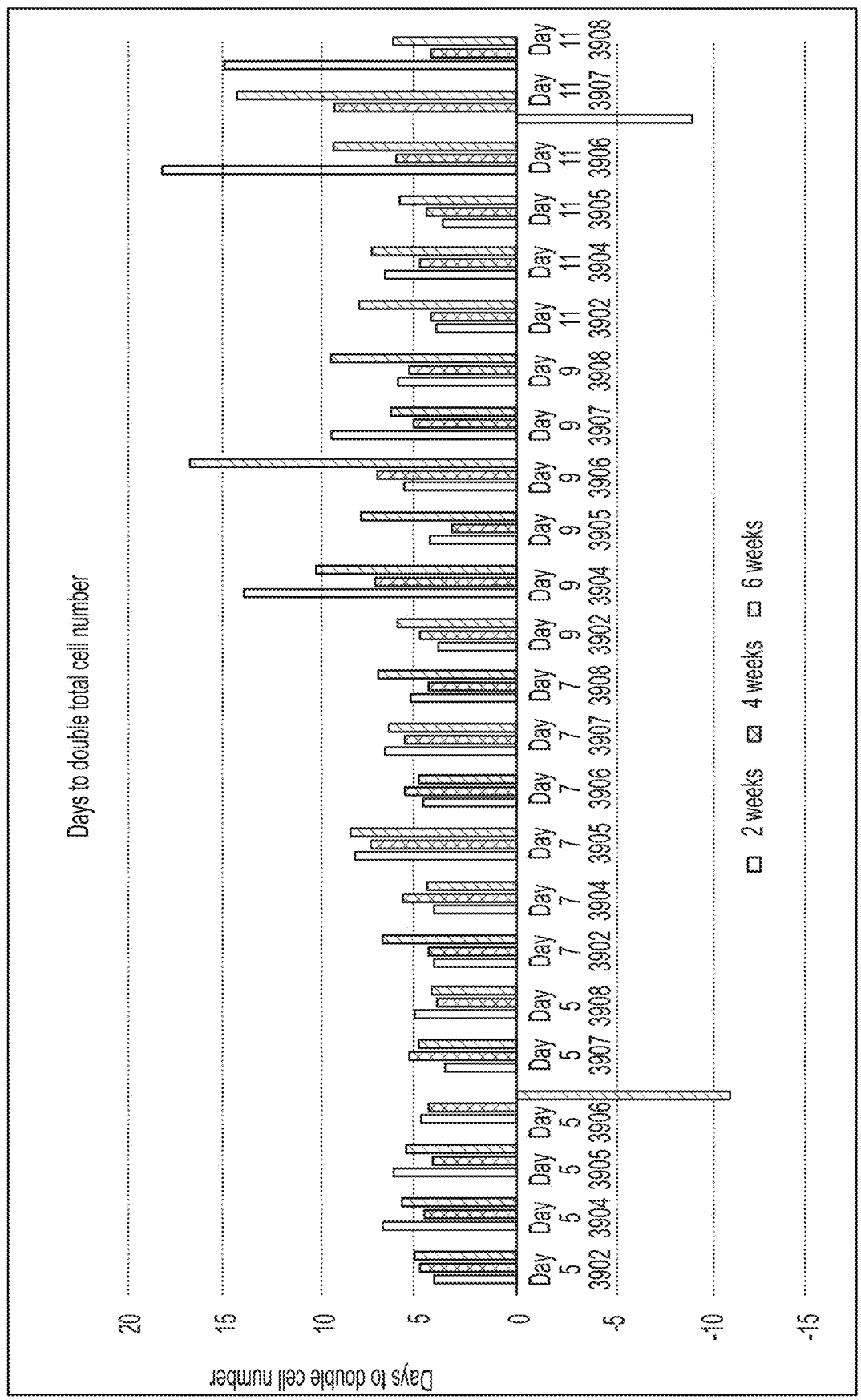

FIG. 20: Quantification of population doubling during lymphoid differentiation of MeCP2WT and MeCP2KO clones. Lymphoid differentiation was initiated by plating cells at 25 K/cm$^2$ on Ret-DLL4 coated plates. The cells were harvested at the end of two, four, and six weeks, population doublings were e=3.32×log (Cell number at harvest/Cell number seeded).

Figure 21:
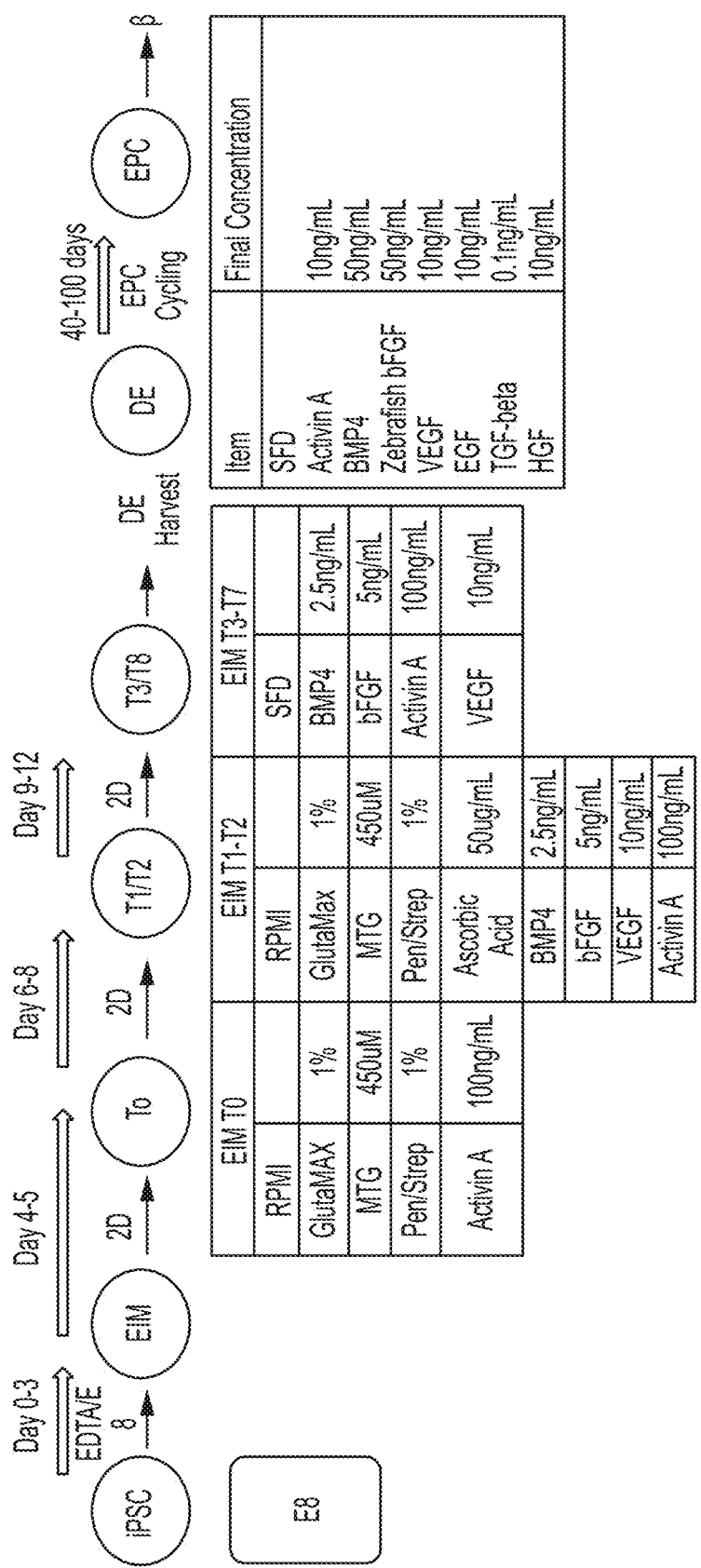

FIG. 21: General overview of the different stages of endoderm differentiation. The conversion of iPSCs to endodermal progenitor stage with the days and factors used in the media to drive the differentiation process is depicted.

Figures 22A, 22B:
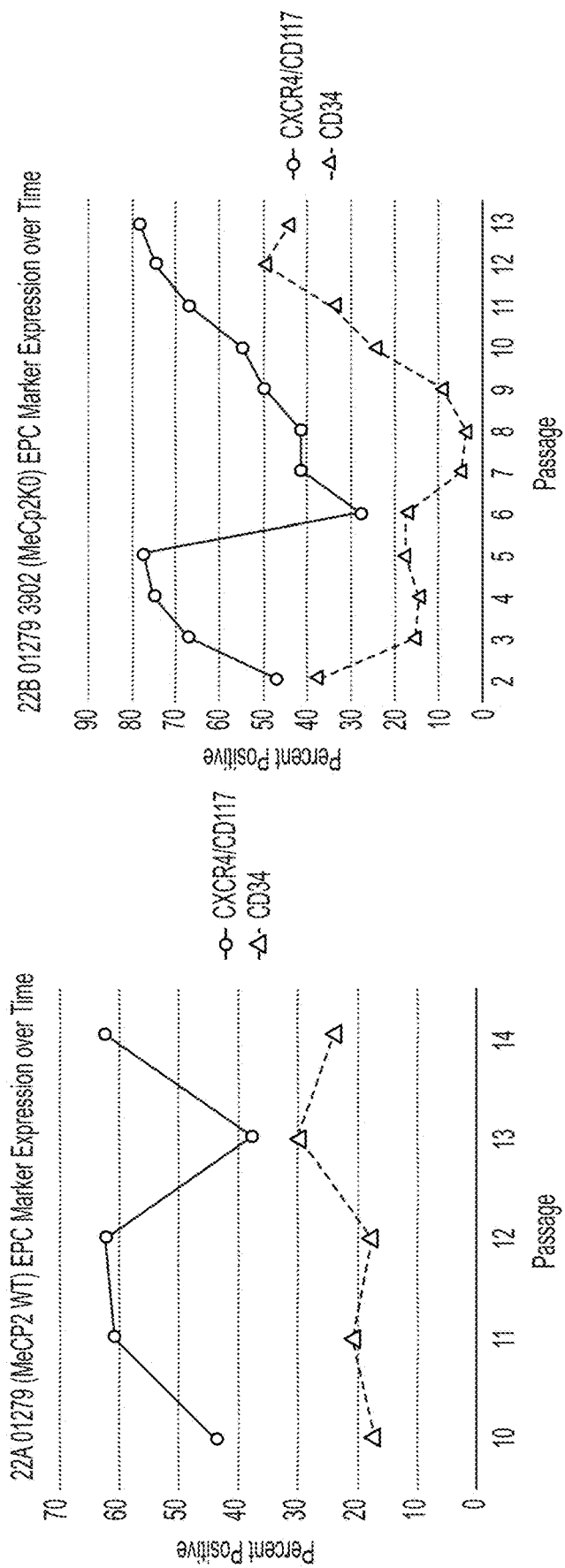

FIGS. 22A-22B: Quantification of EPC purity in 01279 (MeCP2WT) and 01279.107.3902 (MeCP2KO) iPSCs. The graphs represent surface expression of CXCR-4 and CD117 and the maturation marker CD34. (22A) EPCs derived from 01279 (MeCP2WT) were stained between passage 10-14 and (22B) EPCs derived from 01279.107.3902 (MeCP2KO) cells were stained between passage 2-13.

FIGS. 23A-23C: Proliferation and fold expansion in cell number in 01279.107.3902 (MeCP2KO) (23A) EPCs and 01279 (MeCP2WT) (23B) during feeder free cycling. Schematic representation for generating β cells from EPCs propagated in 2D (23C).

FIGS. 24A-24C: Flow cytometric analysis of day 28 end-stage β cells derived from 01279 (MeCP2WT) and 01279.107.3902 (MeCP2KO) EPCs. The cells were harvested, fixed using 4% paraformaldehyde, permeabilized using 0.1% saponin, and stained for the presence of PDX1 (24A), NeuroD1 (24B), and Nkx6.1 (24C) by flow cytometry.

Figure 25A:
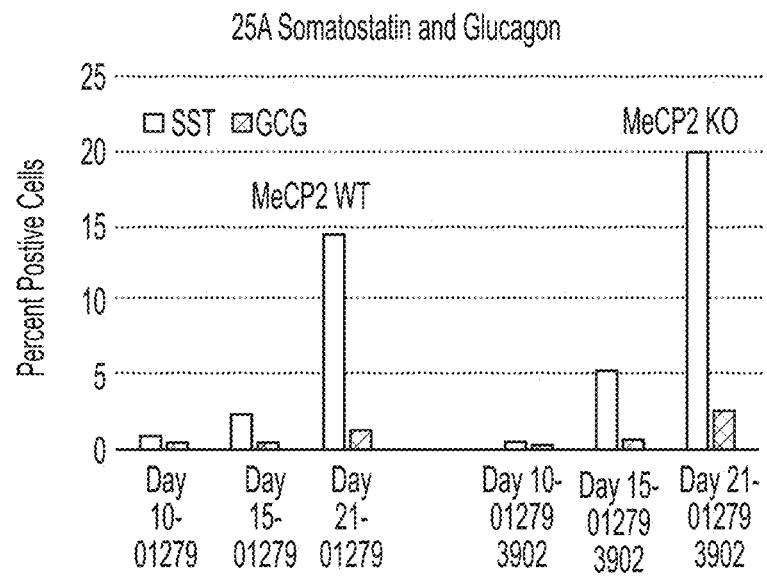
Figure 25B:
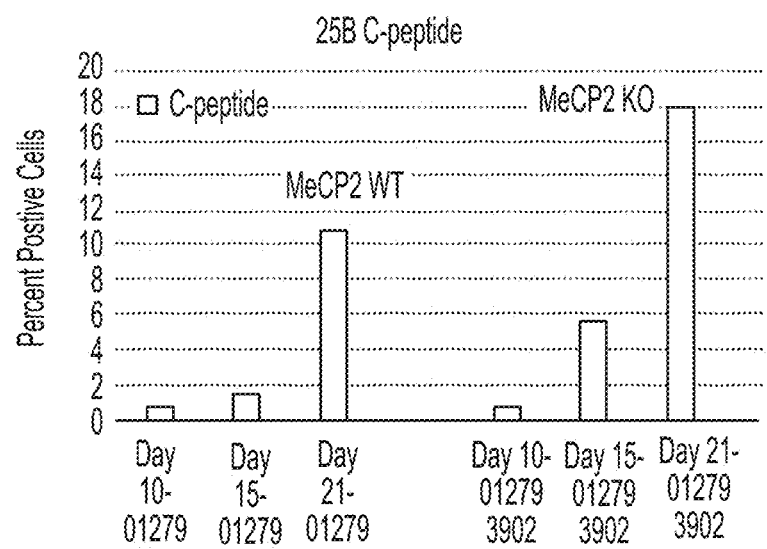

FIGS. 25A-25B: Flow cytometric analysis of day 28 end-stage beta cells derived from 01279 (MeCP2WT) and 01279.107.3902 (MeCP2KO) EPCs. The cells were harvested, fixed using 4% paraformaldehyde, permeabilized using 0.1% saponin, and stained for the presence of Somatostatin and Glucagon (25A), and C-peptide (25B) by flow cytometry.

FIG. 26: FACS profile of intracellular staining of C-peptide, glucagon, and somatostatin expression on day 22 of pancreatic differentiation process following dissociation of the aggregates. The scatter plots represent intracellular staining of glucagon, somatostatin, and C-peptide expression. The plots on the left reveal Forward and Side Scatter of the cells followed by staining post-harvest. The plots reveal dual staining profiles of C-peptide vs. glucagon, C-peptide vs. somatostatin, and C-peptide vs. glucagon staining on iPSC-01279 (MeCP2WT) and 01279.107.3902 (MeCP2KO) cells.

Figure 27:
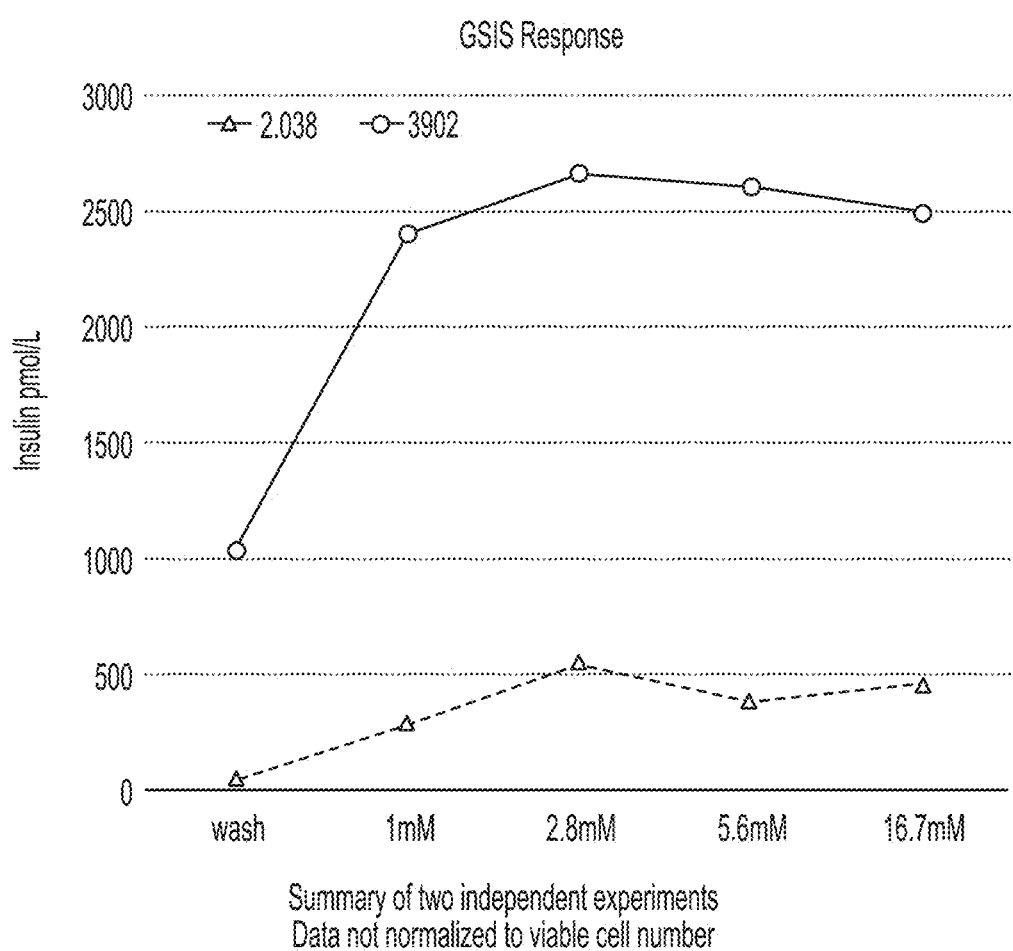

FIG. 27: Glucose responsiveness of end-stage β cells generated from iPSC-01279 (MeCP2WT) and 01279.107.3902 (MeCP2KO) cells. Data represents release of non-normalized C-peptide release to various concentration of glucose. The data is not normalized to cell number assay.

Figure 28:
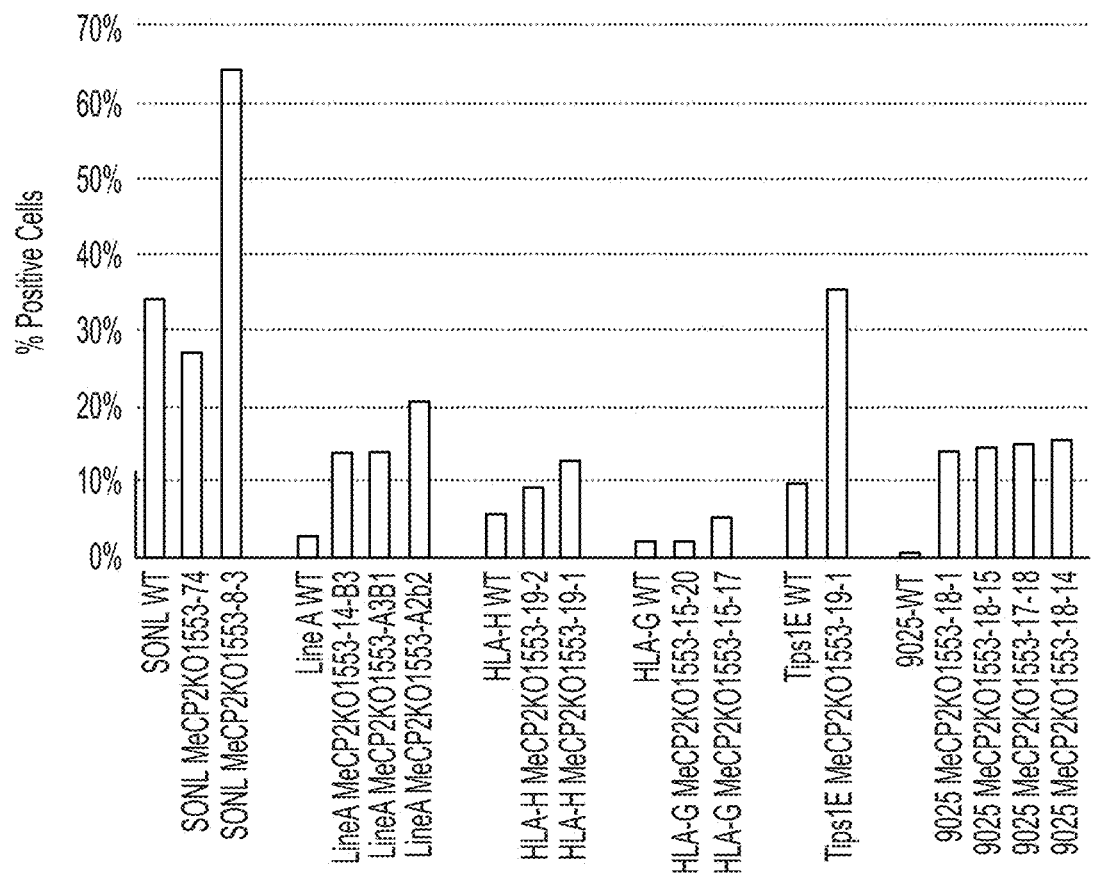

FIG. 28: CD43 expression of Day 9 HPC differentiation derived from indicated MeCP2WT and MeCP2KO iPSC lines.

Figure 29:
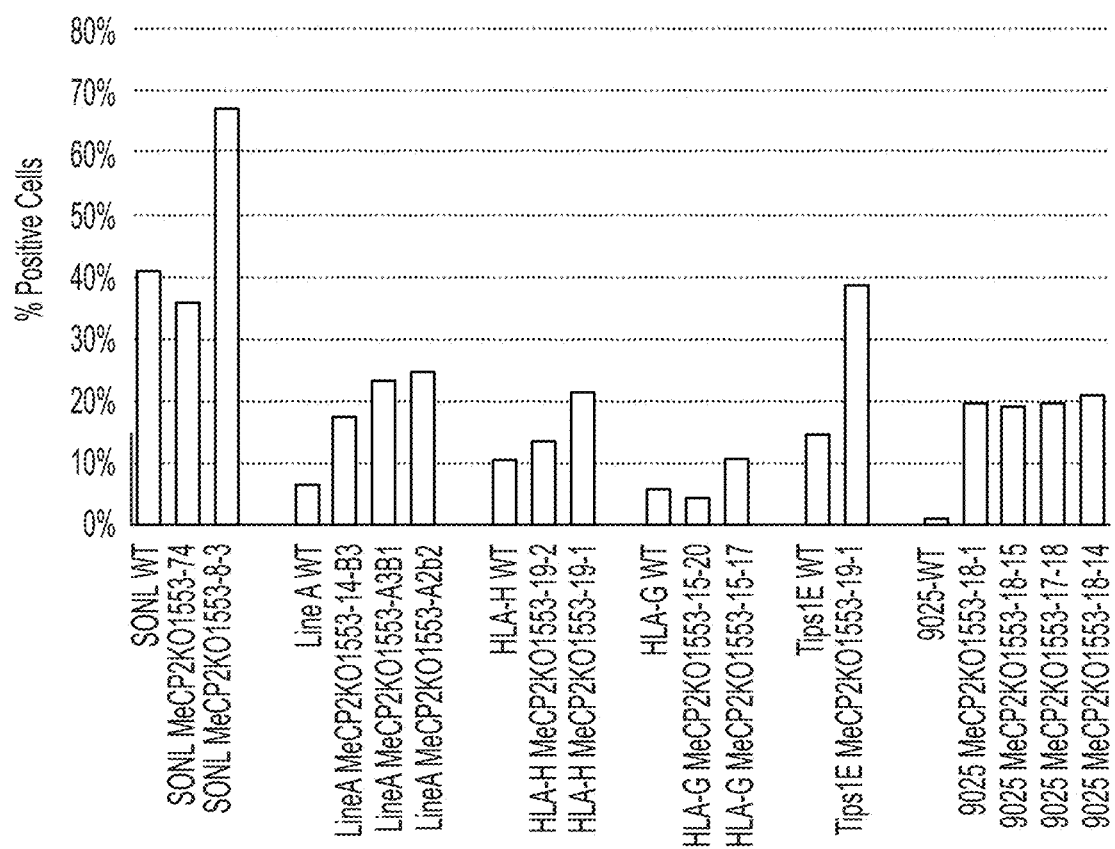

FIG. 29: CD34 expression on Day 9 HPC differentiation derived from indicated MeCP2WT and MeCP2KO iPSC lines.

Figure 30:
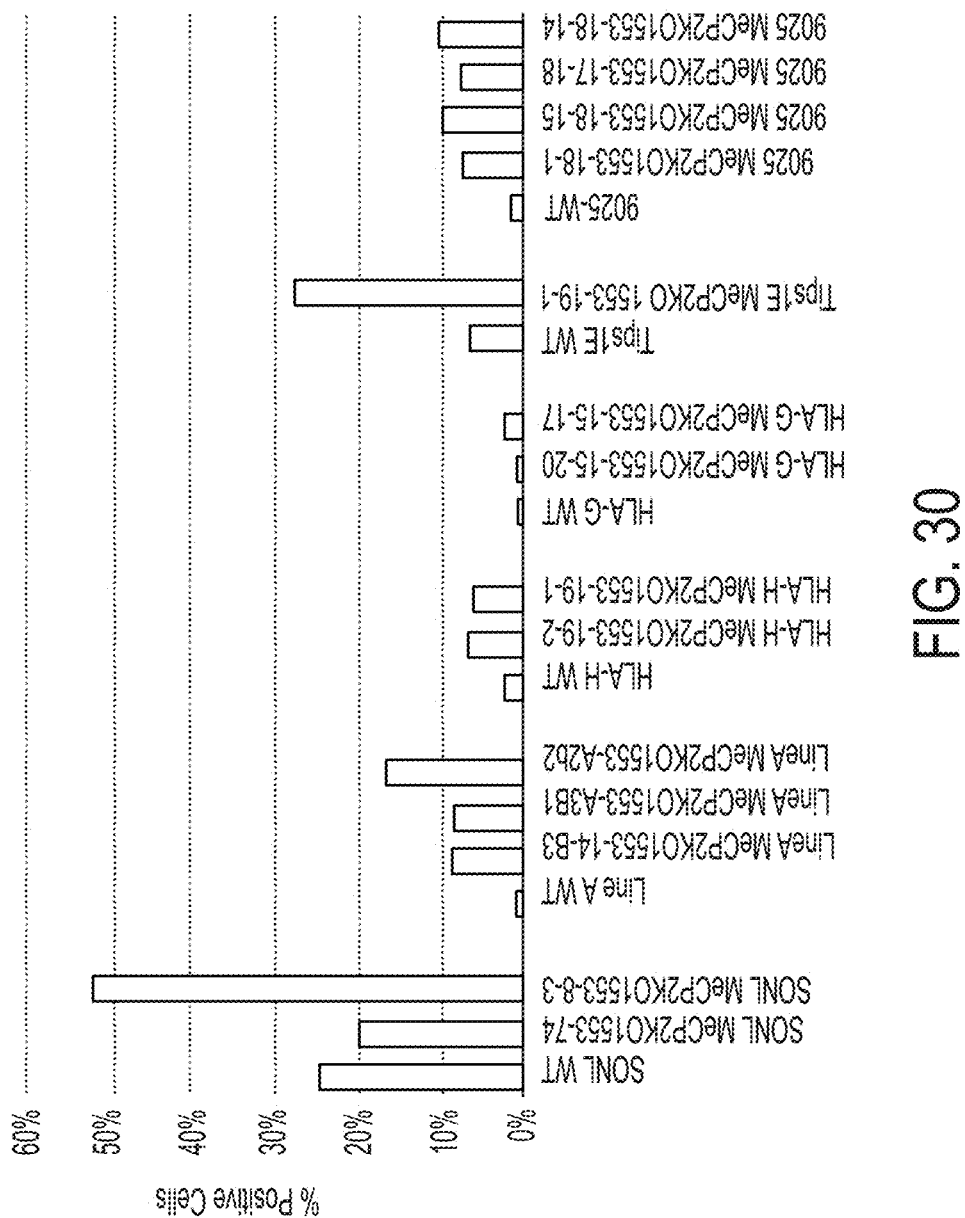

FIG. 30: Percent of CD34- and CD43-positive cells on Day 9 HPC differentiation derived from indicated MeCP2WT and MeCP2KO iPSC lines.

Figure 31:
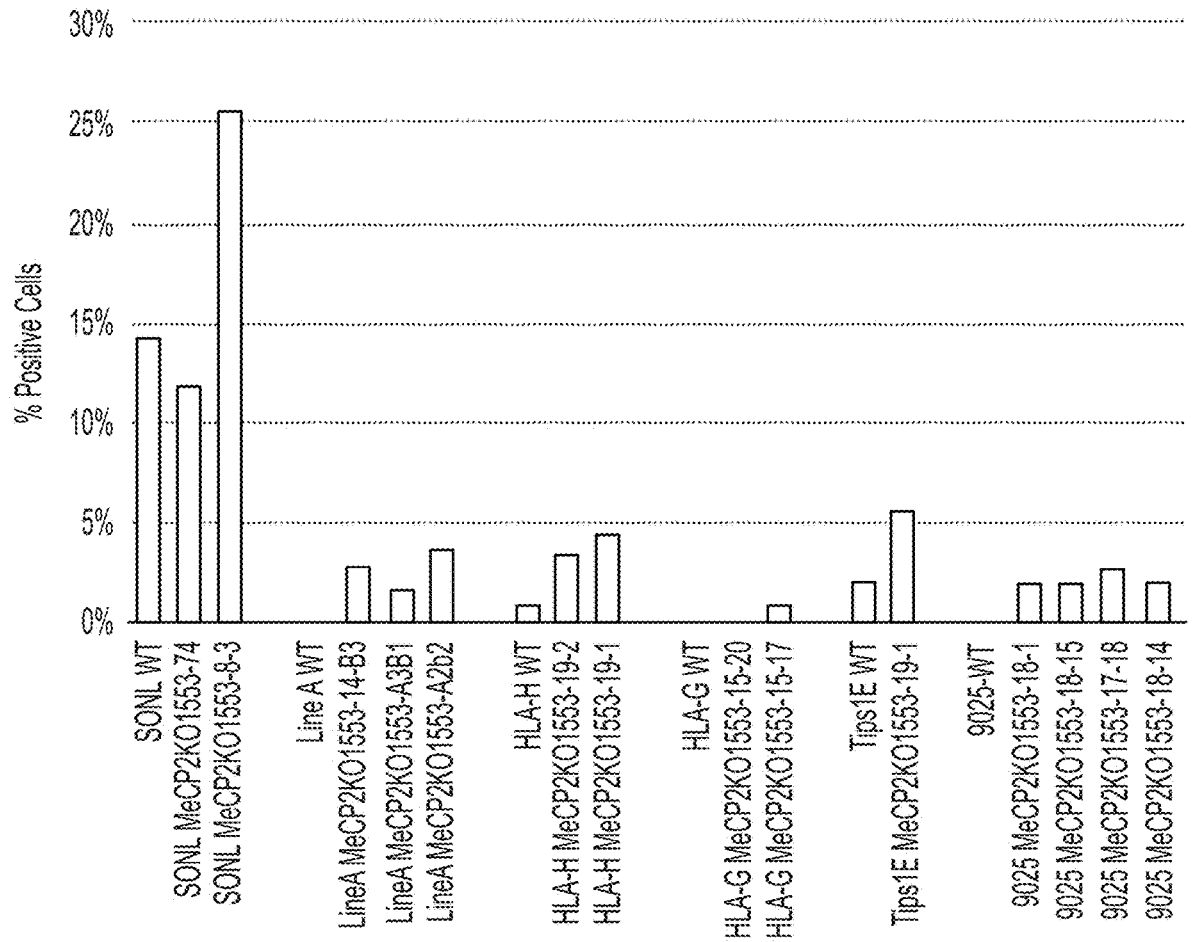

FIG. 31: Percent of CD45-positive cells on Day 9 HPC differentiation derived from indicated MeCP2WT and MeCP2KO iPSC lines.

Figure 32A:
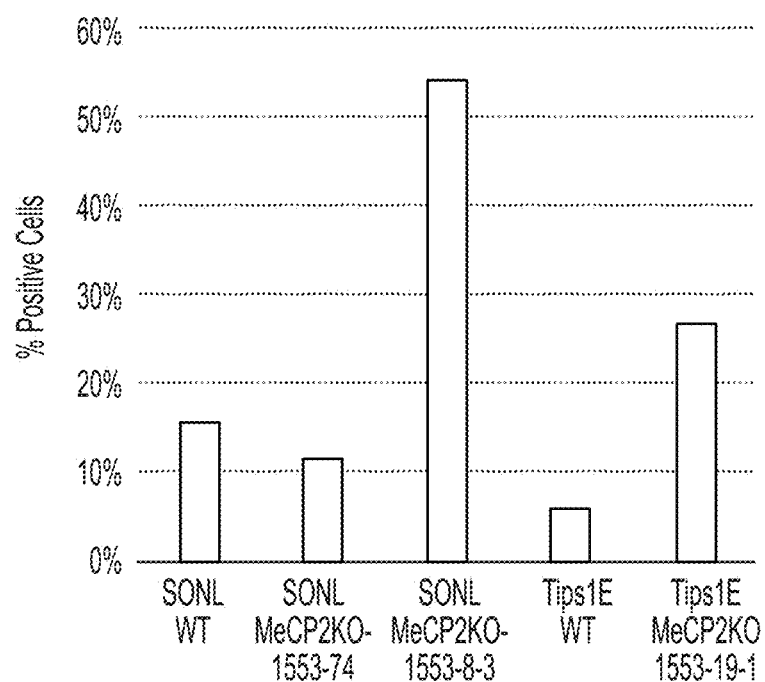
Figure 32B:
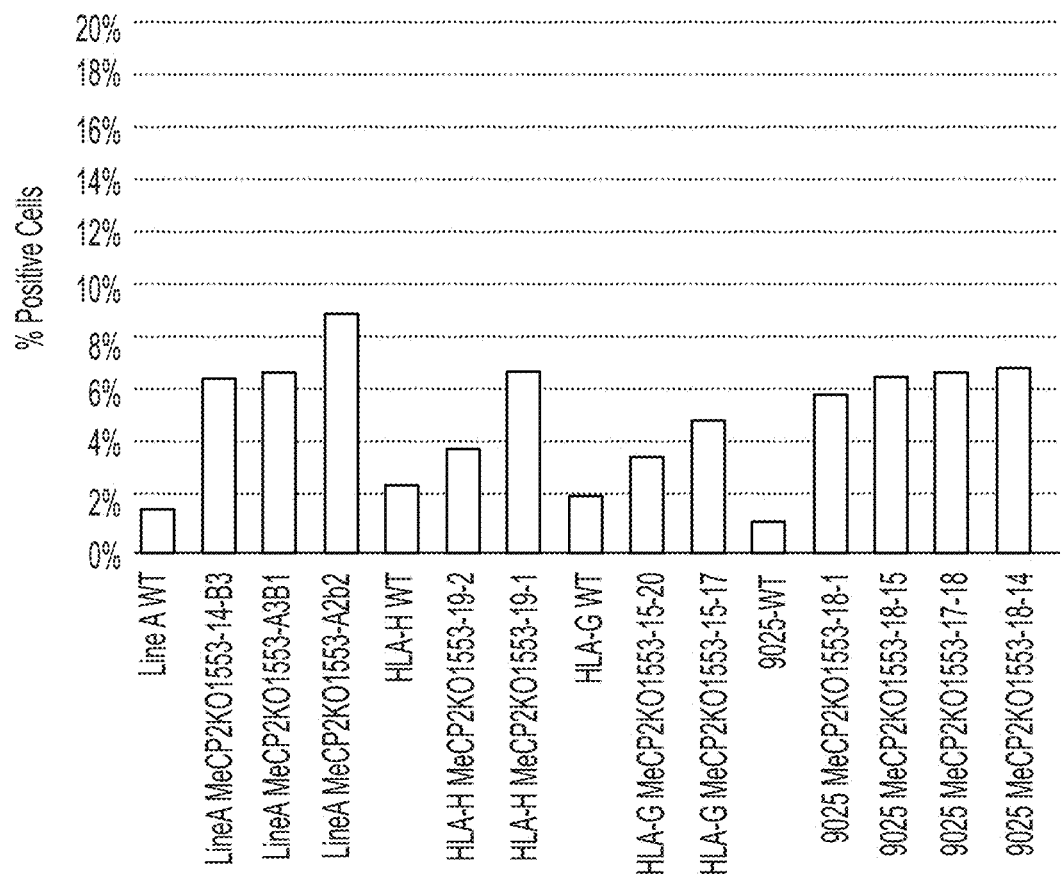

FIGS. 32A-32B: Percent of CD235-positive cells on Day 9 HPC differentiation derived from indicated MeCP2WT and MeCP2KO iPSC lines.

Figure 33:
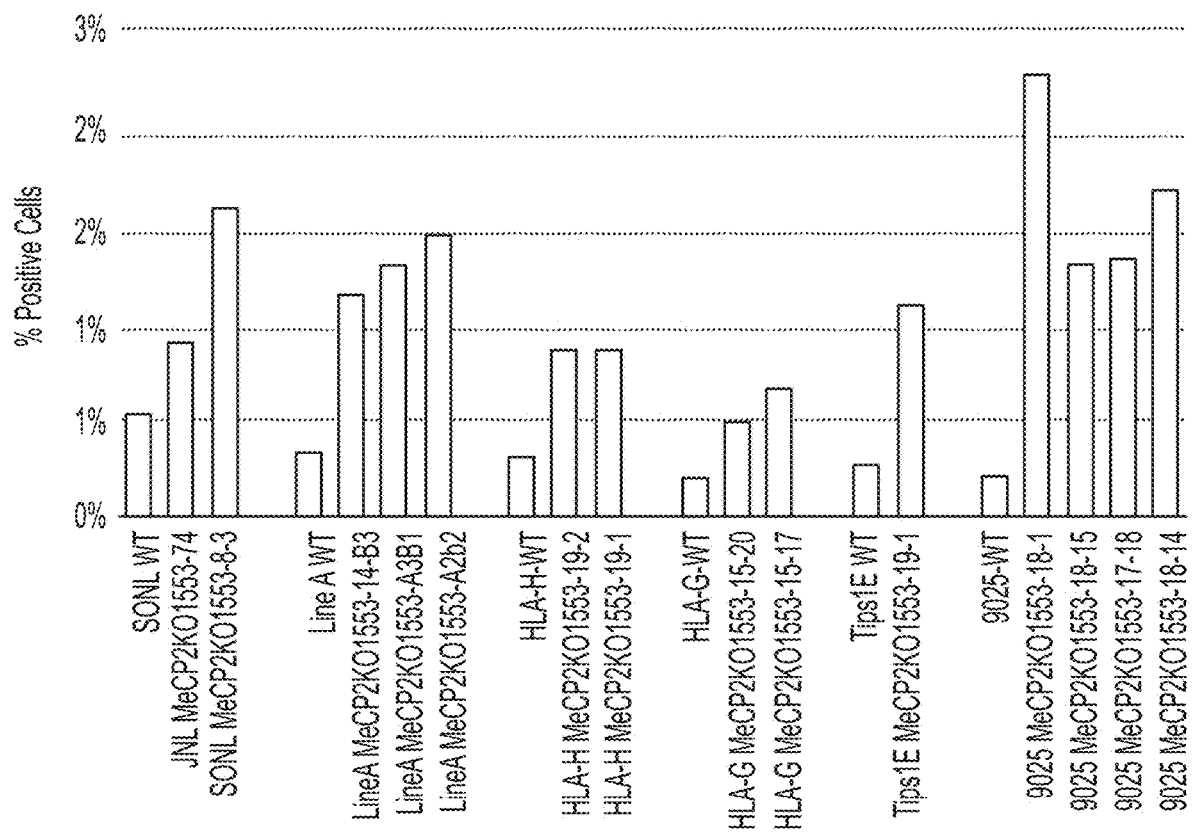

FIG. 33: Percent of DLL4-positive cells on Day 9 HPC differentiation derived from indicated MeCP2WT and MeCP2KO iPSC lines.

Figure 34:
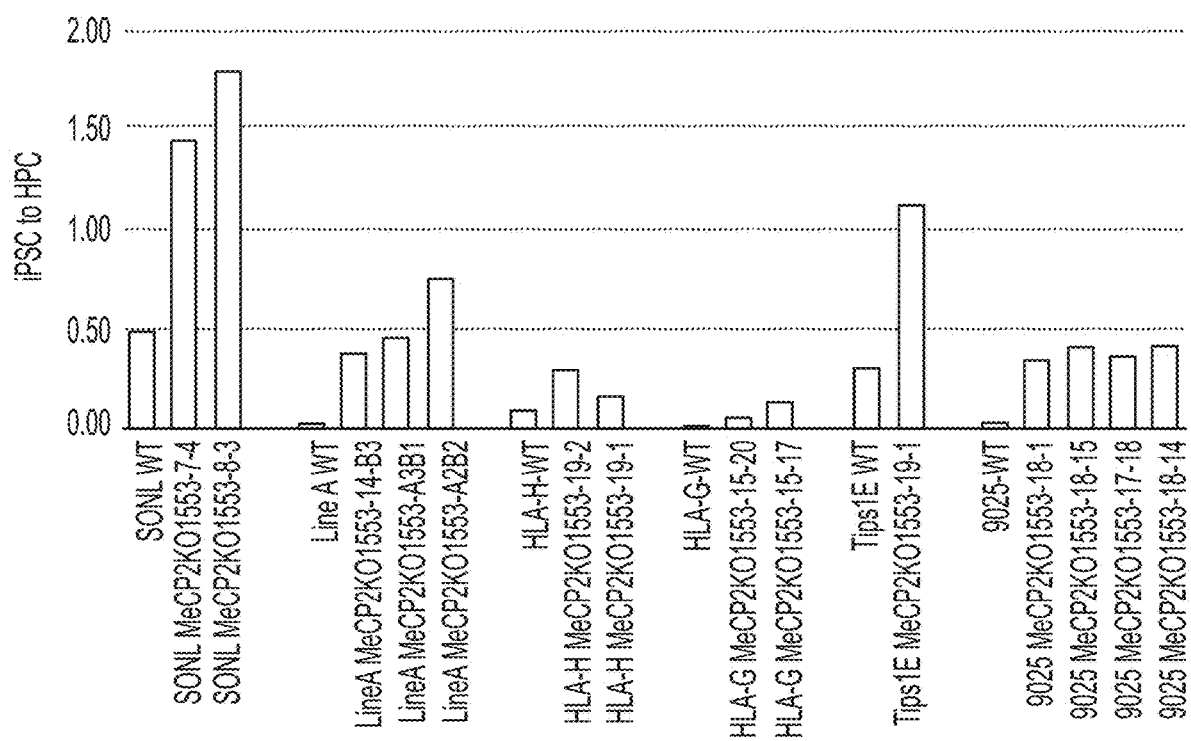

FIG. 34: Efficiency of HPC generation from indicated iPSC MeCP2WT or MeCP2KO lines.

Figure 35:
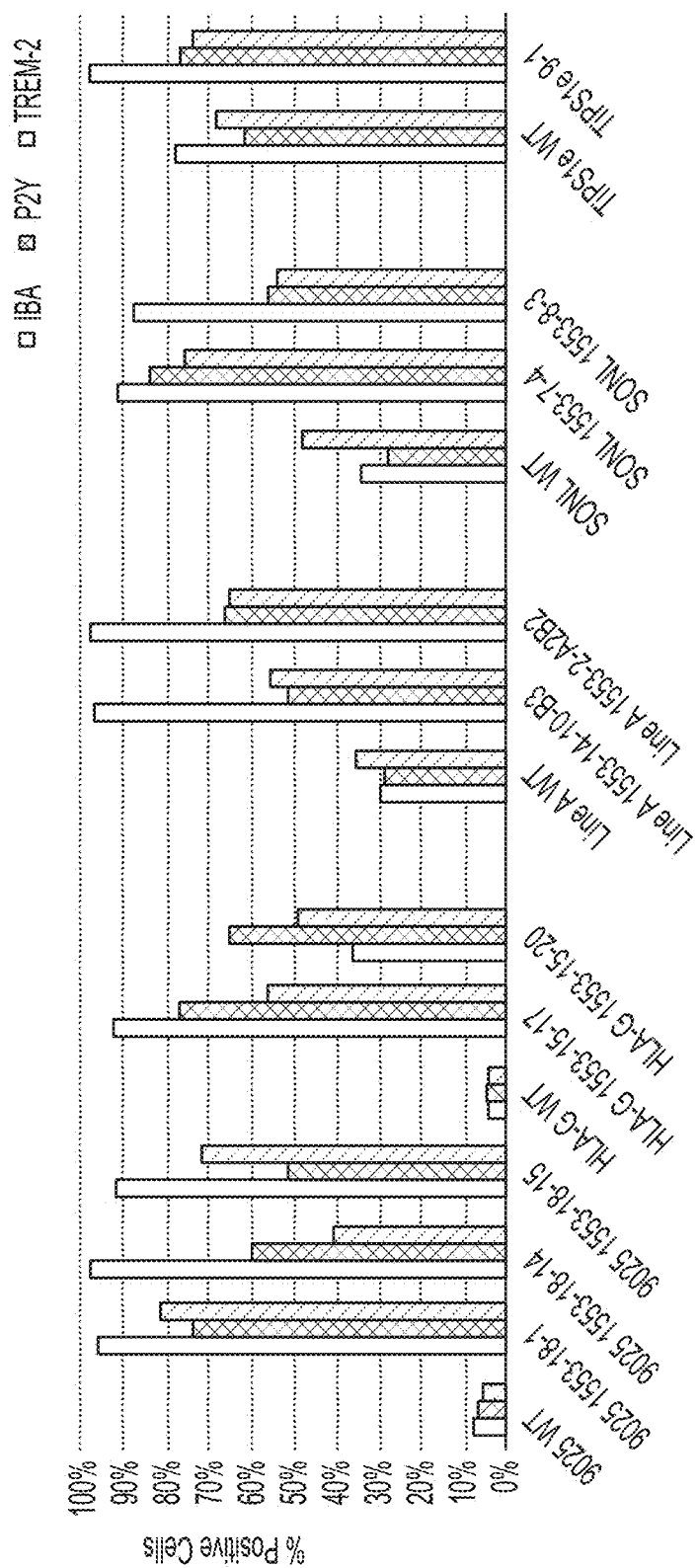

FIG. 35: Microglia were differentiated from the different iPSC clones and their purity was assessed by the markers IBA, P2RY, and TREM-2 to compare MeCP2WT vs. MeCP2KO iPSC cell-derived microglia.

Figure 36:
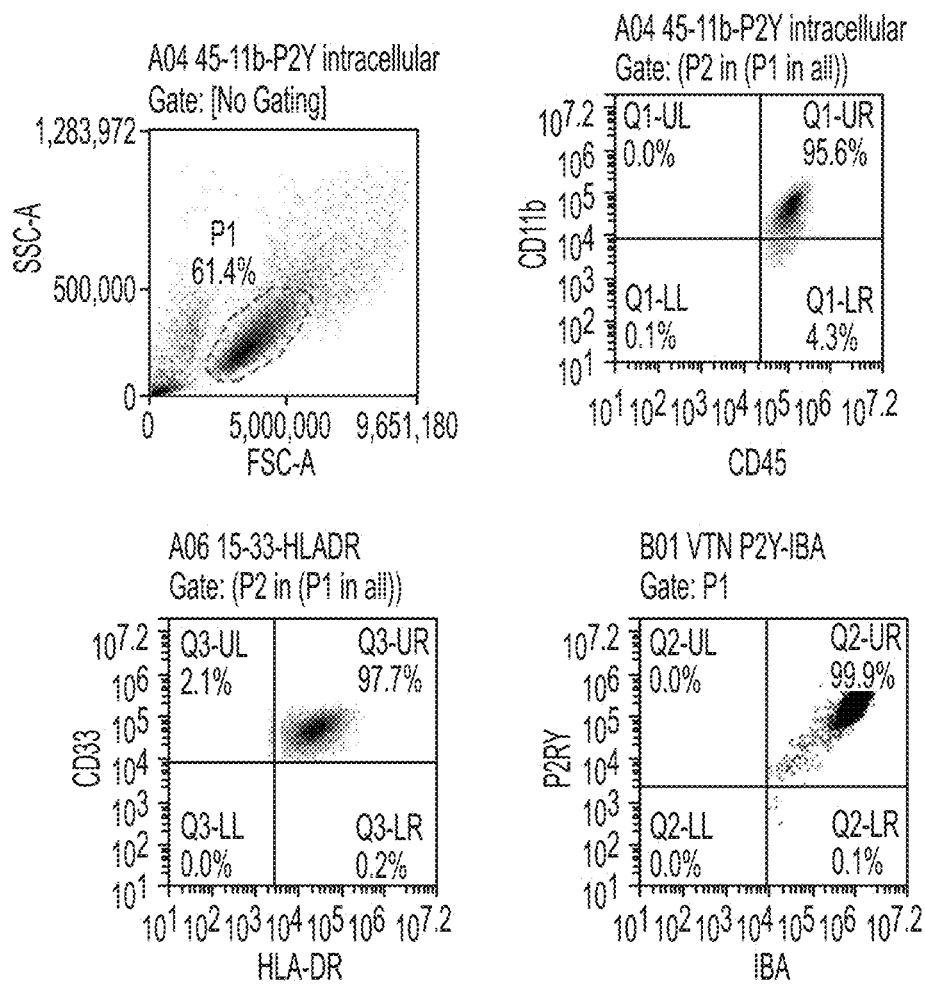

FIG. 36: FACS analysis of the purity of end stage microglia.

Figure 37:
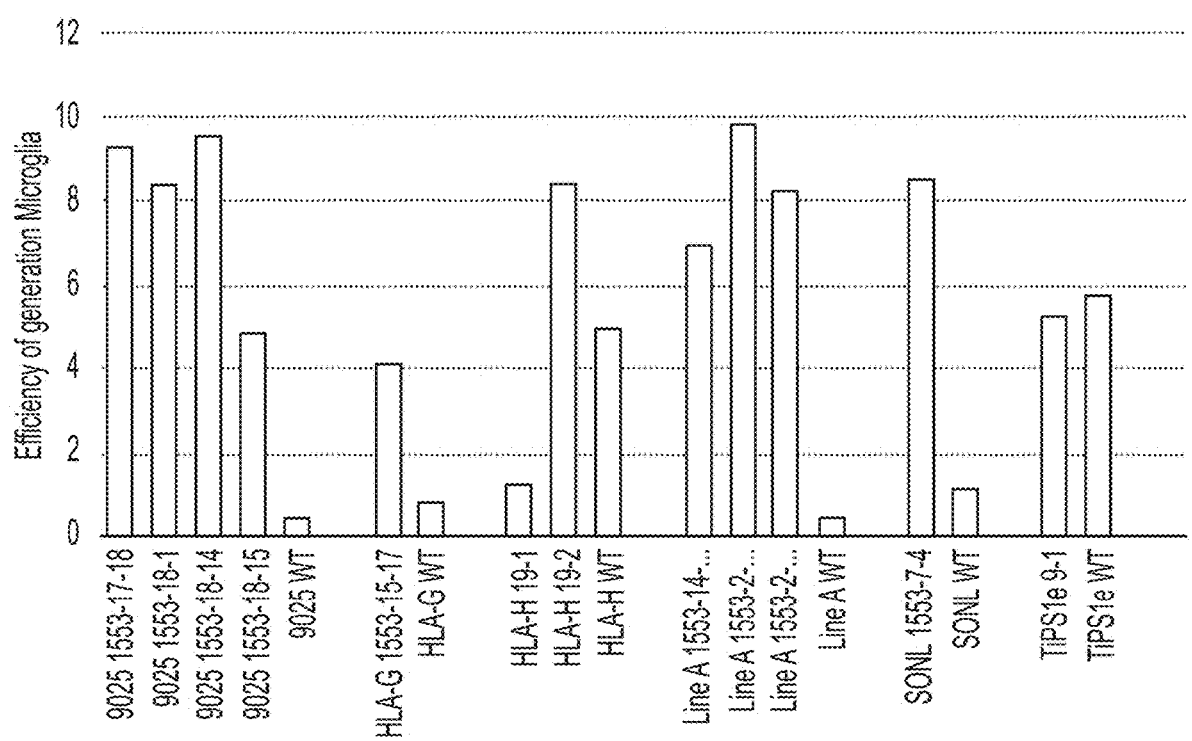

FIG. 37: Efficiency of microglia generation from one HPC derived from the indicated MeCP2WT or MeCP2KO iPSC lines.

Figure 38A:
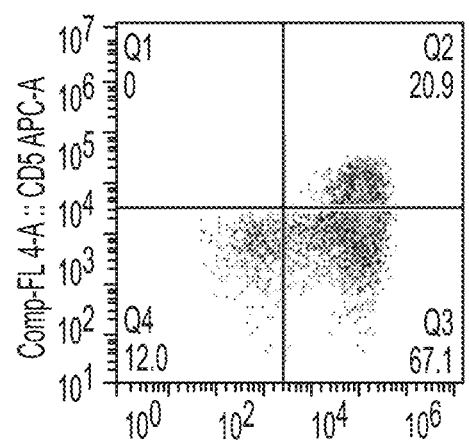
Figure 38B:
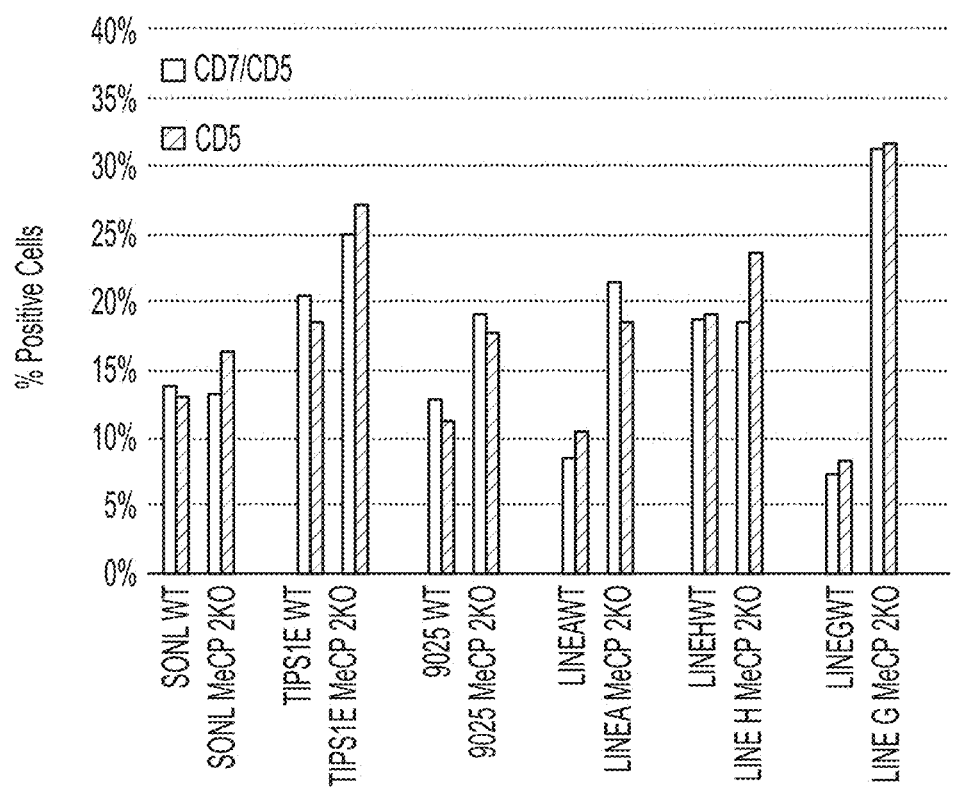
Figure 38C:
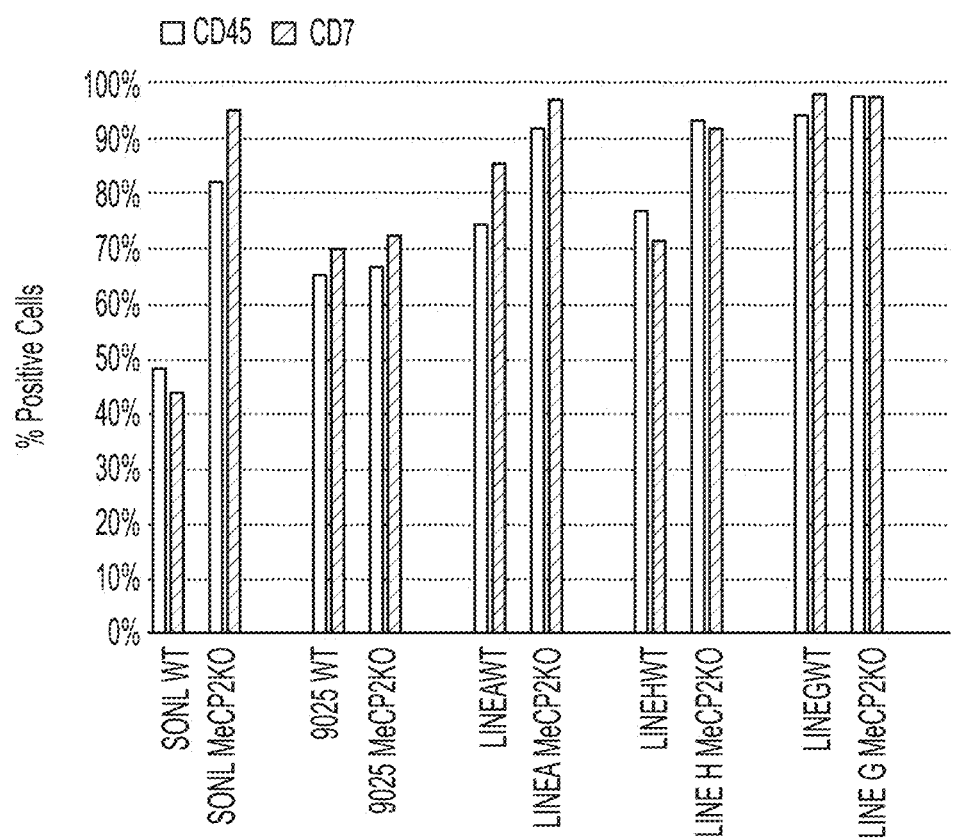

FIGS. 38A-38C: Pre-T cells were differentiated from MeCP2WT or MeCP2KO iPSCs. (38A) Snapshot of FACS profile for pre-T cells as measured by CD5 and CD7. (38B) Cells were harvested at the end of 2 weeks and the percentage of pre-T progenitor cells were quantified by CD7/CD45 (38C) or CD7/CD5.

FIGS. 39A-39F: The pre-T cells of FIG. 38 were differentiated an additional 2 weeks. (39A) Snapshot of FACS profile for T cells as measured by CD3 and CD8. The cells were harvested at the end of 2 weeks and quantified for total CD3-positive cells, cytotoxic T cells (CD3$^+$/CD8$^+$), NK cells (CD3–/CD56$^+$) and NK/T cells (CD3$^+$CD56$^+$). The cells were differentiated from (39B) SONL iPSCs, (39C) 9025 iPSCs, (39D) iPSC Line A, (39E) iPSC line F, or (39F) iPSC line H.

Figure 40:
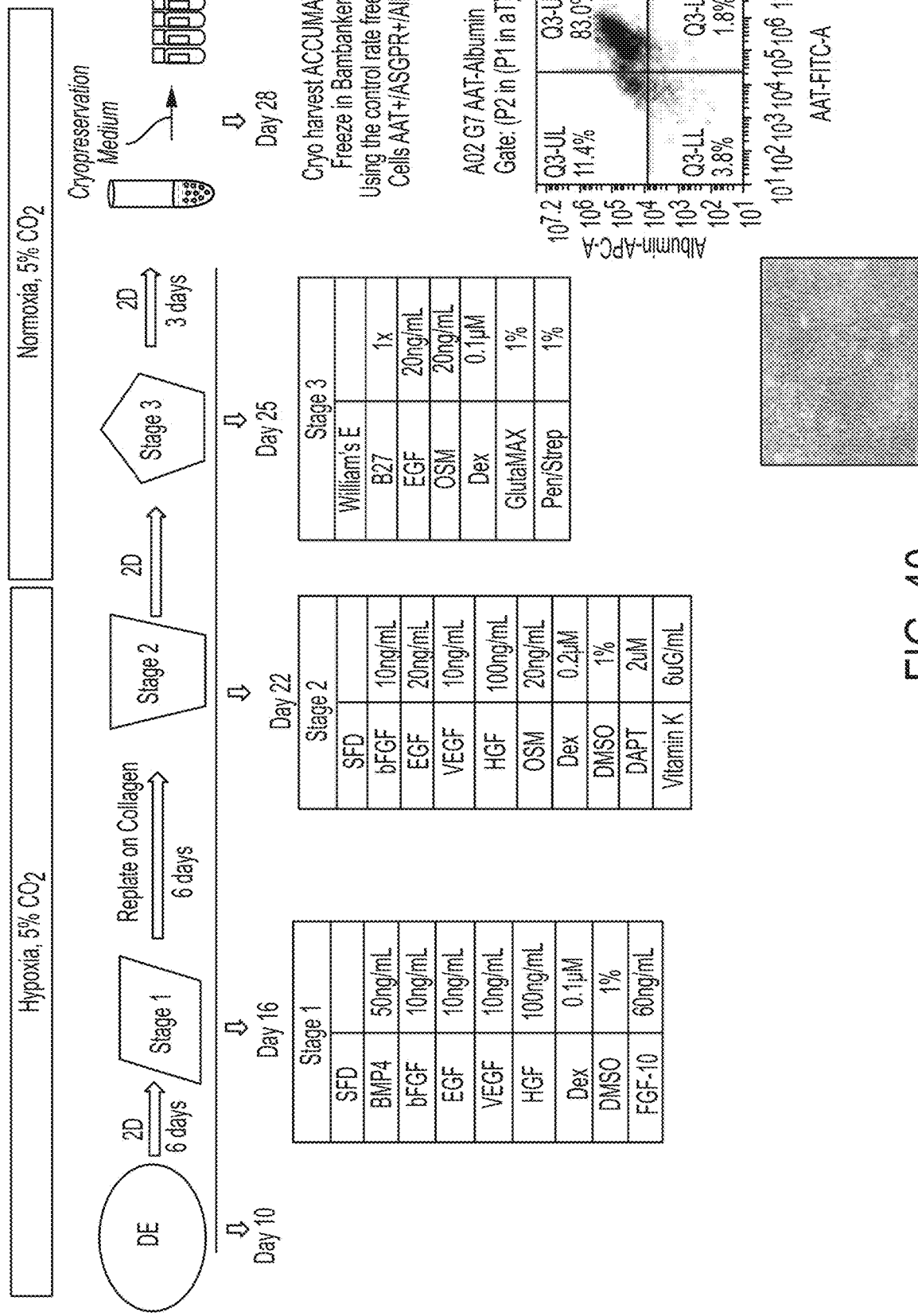

FIG. 40: Schematic depicting 2D protocol to derive hepatocytes from MeCP2WT or MeCP2KO iPSC lines.

Figure 41:
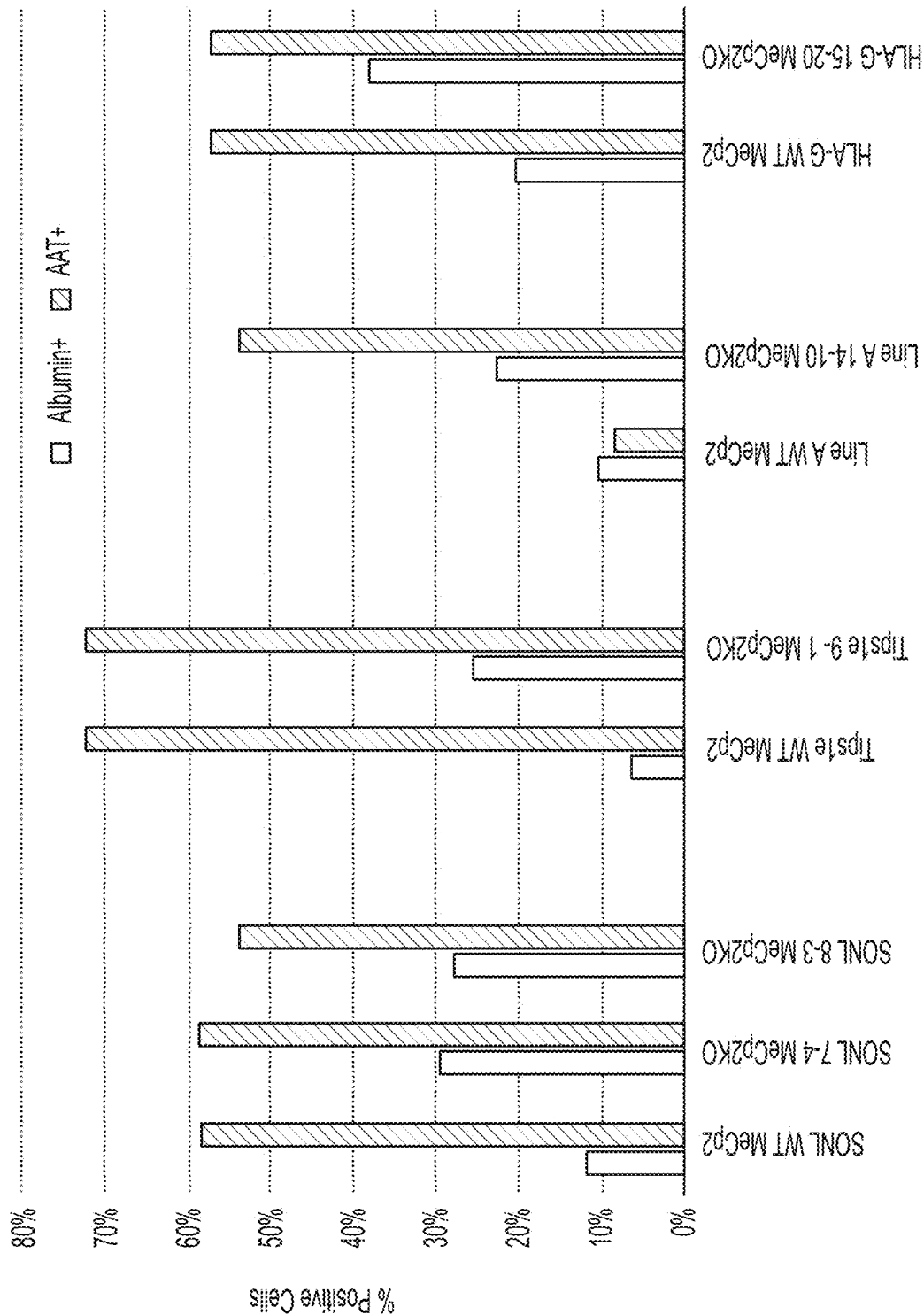

FIG. 41: Hepatocyte differentiation from indicated iPSC lines with MeCP2KO. The percent of cells positive for Albumin or AAT are shown.

Figure 42:
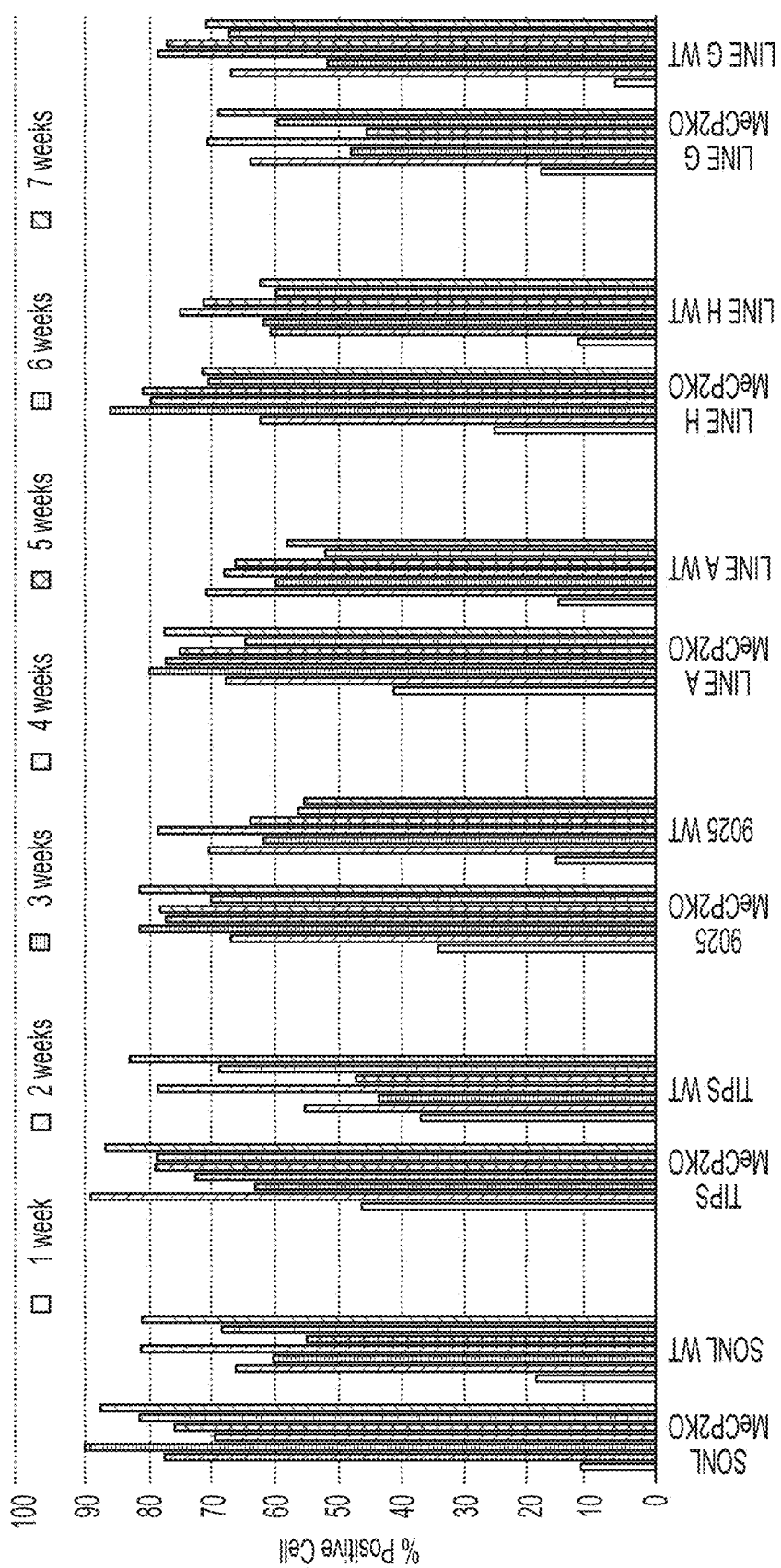

FIG. 42: Effect of MeCP2KO on erythrocyte differentiation. Graph shows percentage of CD235-positive cells during erythroid differentiation for each indicated cell line.

Figure 43A:
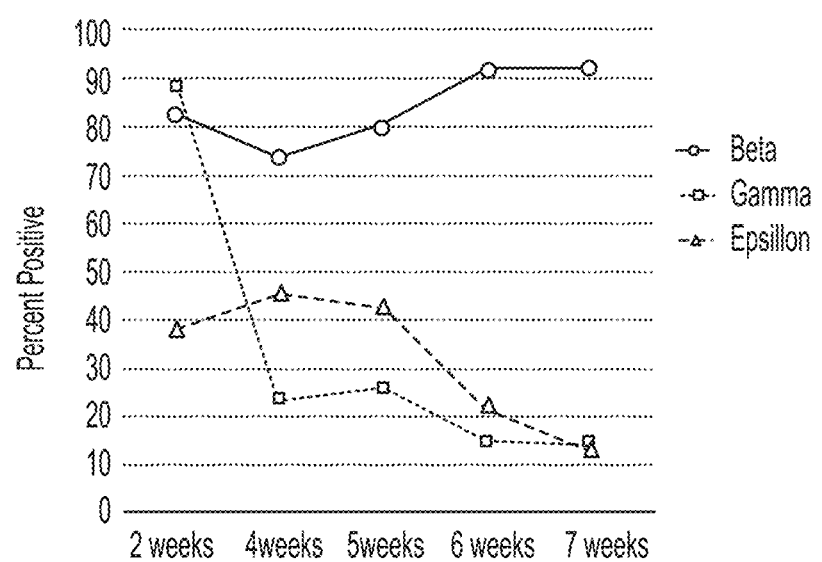
Figure 43B:
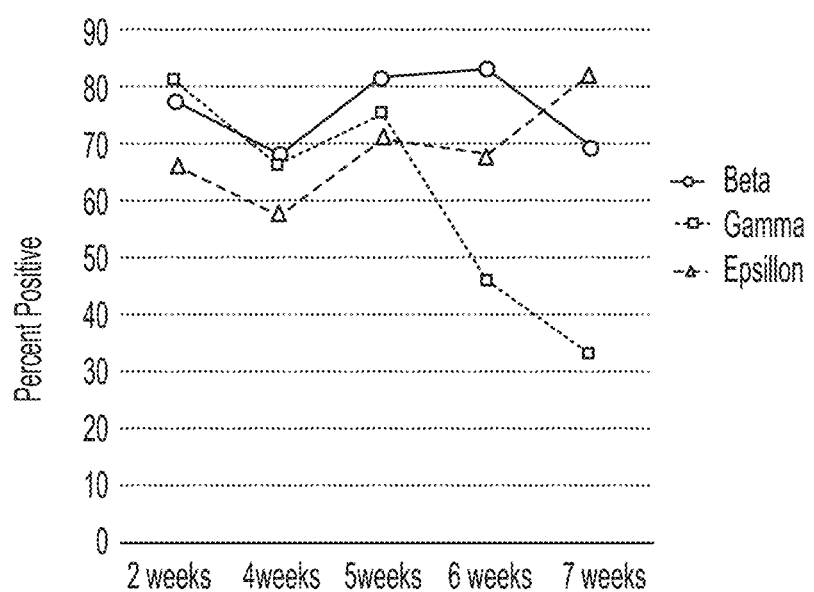

FIGS. 43A-43B: (43A) Globin expression in MeCP2KO erythrocytes differentiated from SONL iPSCs up to 7 weeks. (43B) Globin expression in MeCP2WT erythrocytes differentiated from SONL iPSCs over 7 weeks.

Figure 44A:
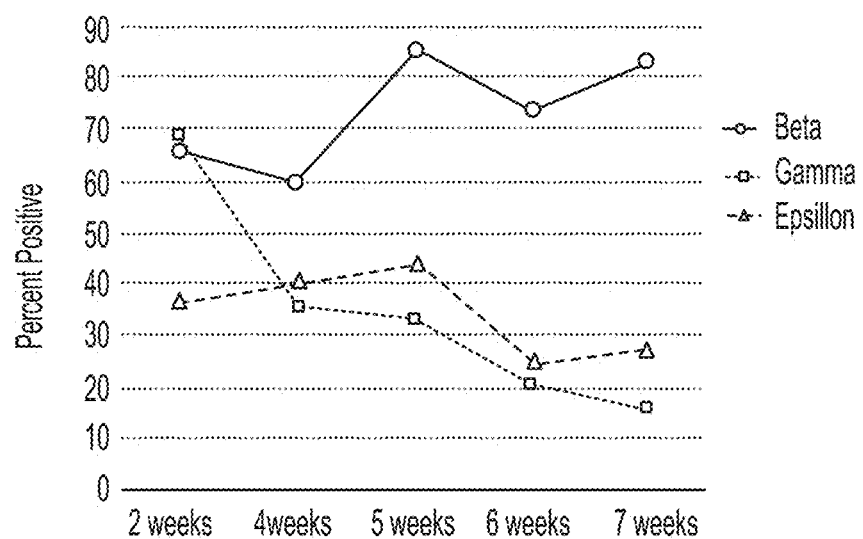
Figure 44B:
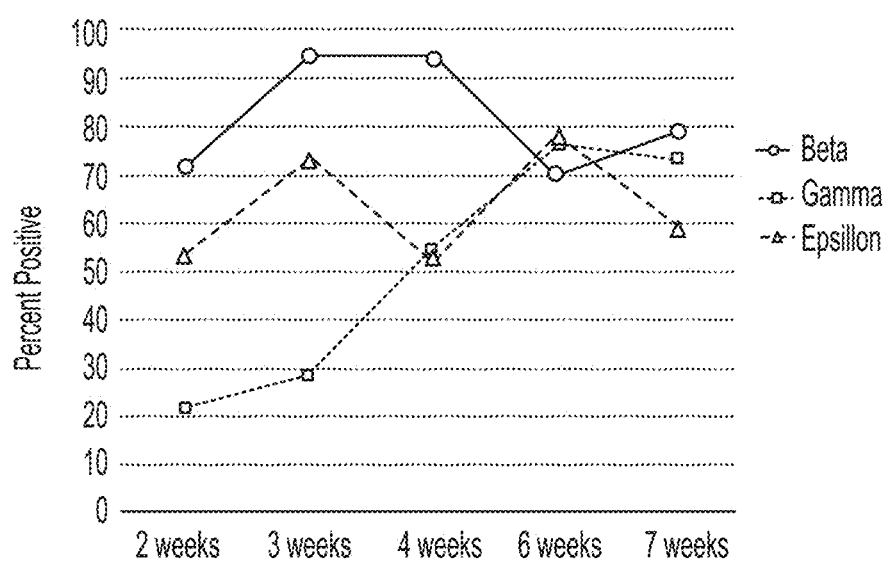

FIGS. 44A-44B: (44A) Globin expression in MeCP2KO erythrocytes differentiated from TiPS iPSCs up to 7 weeks. (44B) Globin expression in MeCP2WT erythrocytes differentiated from TiPS iPSCs over 7 weeks.

Figure 45A:
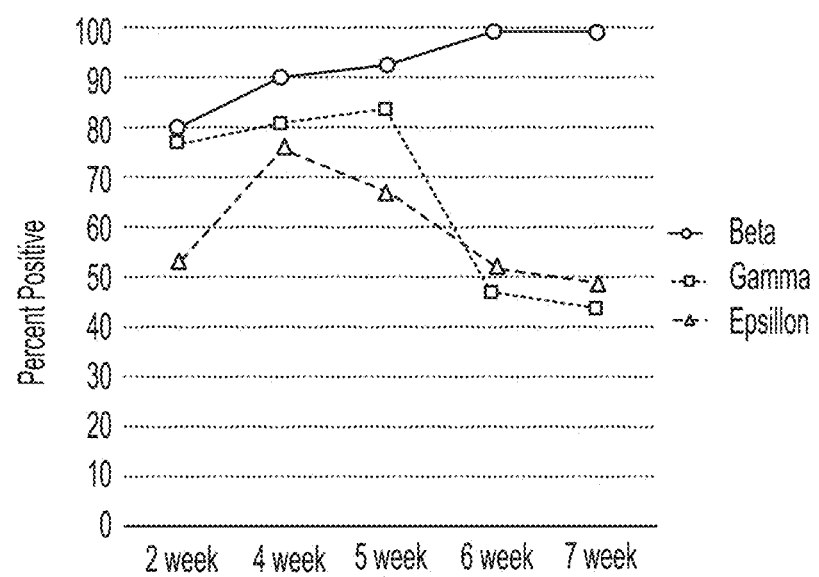
Figure 45B:
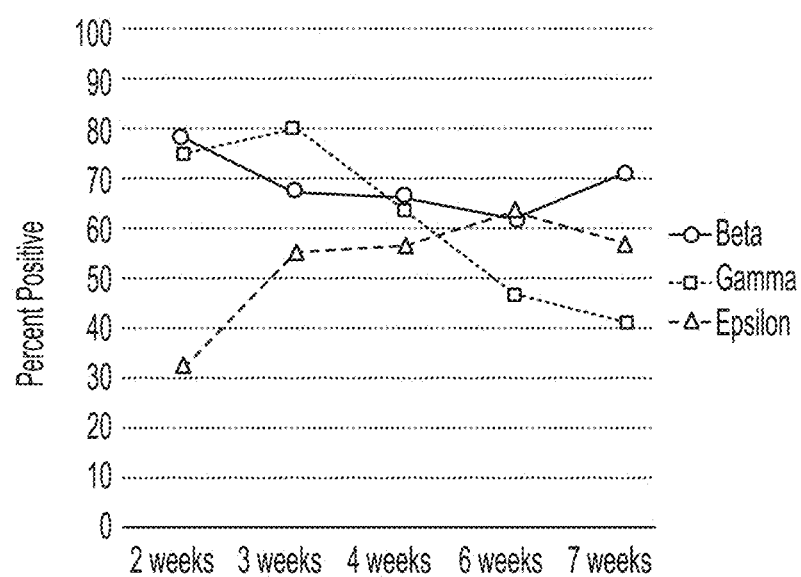

FIGS. 45A-45B: (45A) Globin expression in MeCP2KO erythrocytes differentiated from 9025 iPSCs up to 7 weeks. (45B) Globin expression in MeCP2WT erythrocytes differentiated from 9025 iPSCs over 7 weeks.

Figure 46A:
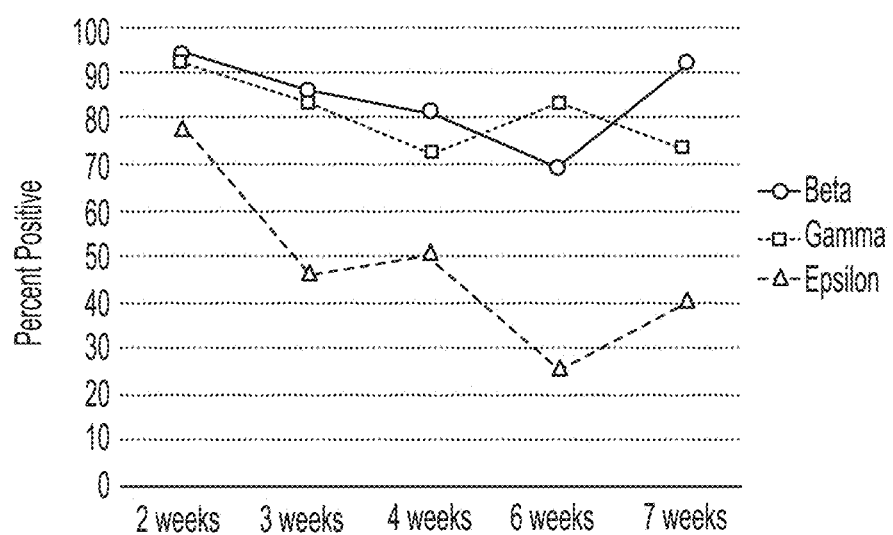
Figure 46B:
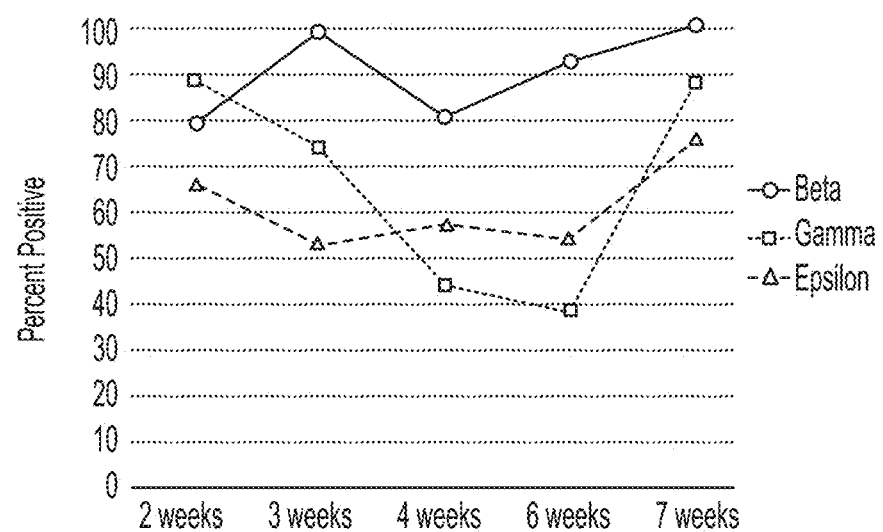

FIGS. 46A-46B: (46A) Globin expression in MeCP2KO erythrocytes differentiated from Line A iPSCs up to 7 weeks. (46B) Globin expression in MeCP2WT erythrocytes differentiated from Line A iPSCs over 7 weeks.

Figure 47A:
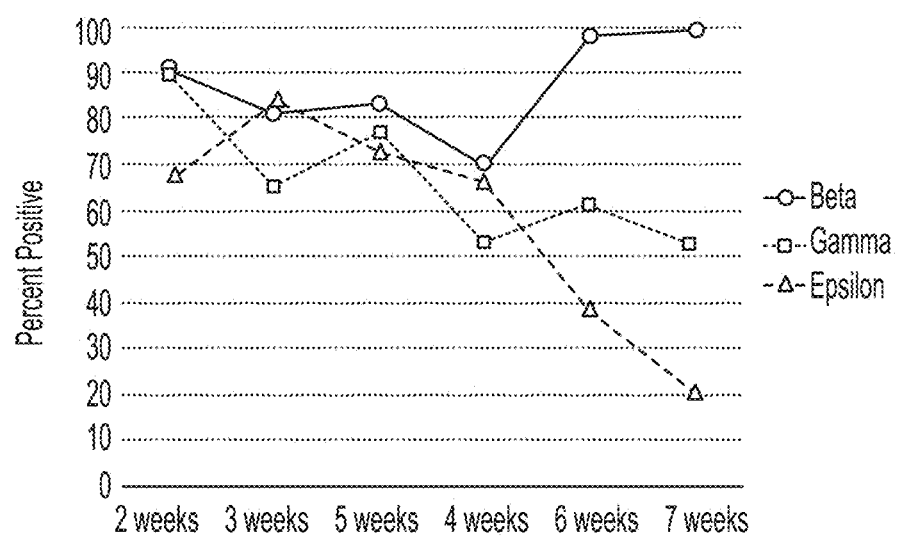
Figure 47B:
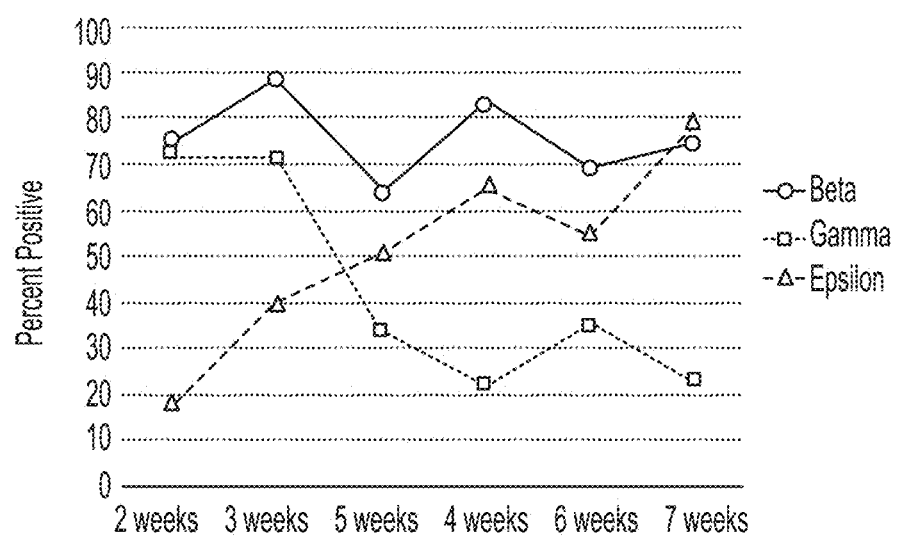

FIGS. 47A-47B: (47A) Globin expression in MeCP2KO erythrocytes differentiated from Line H iPSCs up to 7 weeks. (47B) Globin expression in MeCP2WT erythrocytes differentiated from Line H iPSCs over 7 weeks.

Figure 48A:
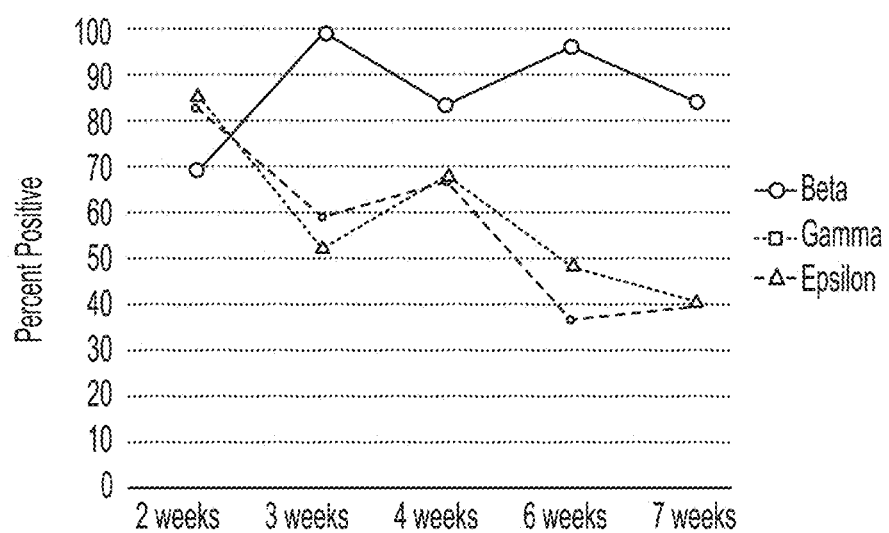
Figure 48B:
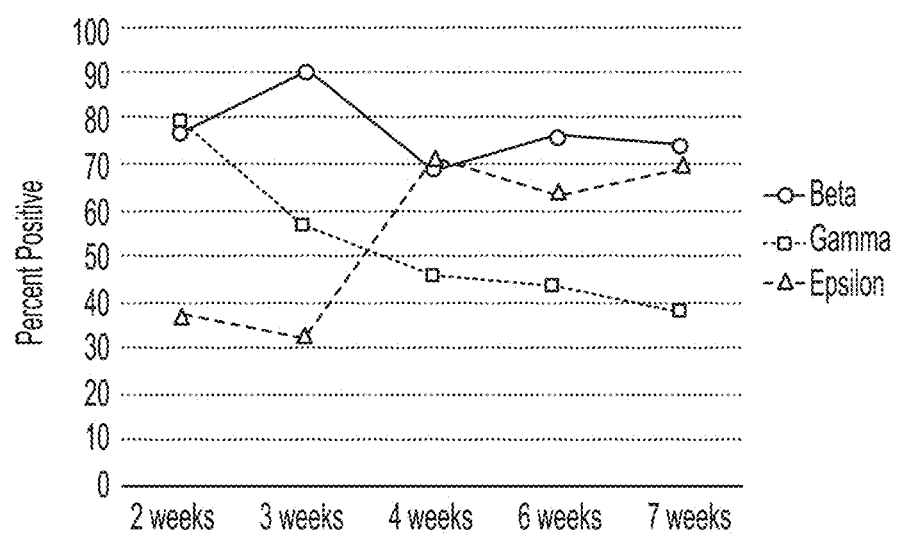

FIGS. 48A-48B: (48A) Globin expression in MeCP2KO erythrocytes differentiated from Line G iPSCs up to 7 weeks. (48B) Globin expression in MeCP2WT erythrocytes differentiated from Line G iPSCs over 7 weeks.

DESCRIPTION OF ILLUSTRATIVE EMBODIMENTS

The MeCP2 gene encodes a protein that is able to bind methylated DNA and to regulate the transcription of target genes. The MeCP2 gene has a methyl-CpG binding domain (MBD), a transcriptional repression domain (TRD), a nuclear localization signal (NLS), and a C-terminal segment (Bird et al., 2008). The studies of the present disclosure provide a new role for MeCP2 in directing differentiation of iPSCs to efficiently generate cells of mature lineages and high purity. MeCP2 was also found to be ubiquitous and circadianly regulated. In addition, the present studies support the role of demethylation with the onset of maturity in iPSC-derived lineages.

Accordingly, the present disclosure provides methods of engineering iPSCs to have disruption of MeCP2 expression, such as knockout using TALENS, to produce enhanced iPSCs which have an increased ability to differentiate to a specific cell lineage including cells of the mesoderm, ectoderm, and endoderm germ layers. The iPSCs with MeCP2 disruption may be efficiently differentiated to erythrocytes, megakaryocytes, macrophages, microglia, T cells, NK cells, NK/T cells, B cells, β cells, dendritic cells, such as plasmacytoid dendritic cells, and hepatocytes.

In particular, the iPSC clones with MeCP2 knockout (MeCP2KO) were found to more efficiently produce hematopoietic precursor cells (HPCs) as well as definitive endoderm(DE) cells and endodermal precursor cells (EPCs). The HPCs may be further differentiated to erythroid, lymphoid or myeloid lineages with a high efficiency and purity. For example, the HPCs may be used to generate mature erythrocytes or microglia as well as cells of the lymphoid lineage, such as T cells, B cells, NK cells, and T/NK cells. The DE cells or EPCs may be further differentiated to cells of the endoderm lineage such as β cells and hepatocytes.

The present studies showed that the MeCP2 disruption in the iPSCs resulted in erythrocytes with higher maturity as seen by increased expression of β globin vs. γ globin or ε globin in contrast to the iPSCs with wild-type (MeCP2WT) expression which expressed more γ globin or ε globin.

In addition, the MeCP2 disruption produced iPSCs which are more efficient at producing cells of the erythroid, myeloid (e.g., microglia) and lymphoid lineages, including T cells and NK cells. The enhanced properties of the iPSCs with MeCP2 disruption were observed across several iPSC lines including virally and episomally reprogrammed iPSCs. Thus, the present disclosure provides methods and compositions for producing mesodermal cells including lymphoid and erythroid, myeloid lineage cells as well as endodermal cells such as hepatocytes and beta cells, from PSCs with a disruption of MeCP2.

In one method, iPSCs with MeCP2 disruption are generated through the engineering of iPSCs using TALENs to insert stop codons before the methyl binding domain of MeCP2. The MeCP2 knockout iPSCs may then be differentiated to HPCs, DE cells, or EPCs under defined feeder free, serum free conditions. The HPCs can then be further differentiated to make other hematopoietic cells of the erythroid, myeloid or lymphoid lineage by the methods disclosed herein, while the DE cells or EPCs may accordingly be differentiated to cells of the endodermal lineage. For example, the MeCP2KO HPCs can be differentiated into mature erythrocytes by placing HPCs in an erythroid expansion medium and generate an enriched population of erythroid cells positive for CD71, CD235a and CD36. Importantly, the mature erythrocytes provided herein express the adult definitive β-globin and display enucleation.

Further, in another exemplary method, the HPCs derived from iPSCs containing an MeCP2 disruption can be differentiated into T cells through the use of RetroNectin and DLL-4 as a feeder free matrix. The T cell differentiation may be further enhanced by the use of ascorbic acid to increase the efficiency and maturation as well as by culturing under hypoxic conditions. Interestingly, the inventors have determined an optimal timeframe during HPC differentiation (e.g., day 7-11) for erythroid, myeloid and lymphoid potential.

In addition, the HPCs derived from iPSCs containing an MeCP2 disruption can be efficiently differentiated to a myeloid differentiation pathway to generate end stage migroglia and macrophages.

Thus, the methods of the present disclosure could provide unlimited numbers of hematopoietic lineage cells, such as T cells, NK cells, T/NK cells, and mature erythrocytes, as well as endodermal lineage cells, such as hepatocytes and β cells, for a wide range of applications such as stable transplantation in vivo, screening of compounds in vitro, and elucidating the mechanisms of hematological diseases and injuries. In particular, the large number and purity of erythroid cells produced make the methods of the present disclosure useful for fundamental research in erythroid development and production of RBCs for transfusion.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid and/or a site at or near where DNA synthesis initiates. As an example, an ori for EBV (Ebstein-Barr virus) includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, methods of the present disclosure may also use genetically engineered replication origin of EBV, such as by insertion or mutation of individual elements, as specifically described in Lindner et al., 2008.

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" or co-expressed" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" or "co-expressed" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs or iPS cells".

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs or iPS cells)" are cells generated by reprogramming a somatic cell by expressing or inducing expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, Klf4, Nanog, and Lin28. In some embodiments, somatic cells are reprogrammed by expressing at least two reprogramming factors, at least three reprogramming factors, at least four reprogramming factors, at least five reprogramming factors, at least six reprogramming factors, or at least seven reprogramming factors to reprogram a somatic cell to a pluripotent stem cell.

"Hematopoietic progenitor cells" or "hematopoietic precursor cells (HPCs)" refers to cells which are committed to a hematopoietic lineage but are capable of further hematopoietic differentiation and include hematopoietic stem cells, multipotential hematopoietic stem cells, common myeloid progenitors, megakaryocyte progenitors, erythrocyte progenitors, and lymphoid progenitors. Hematopoietic stem cells (HSCs) are multipotent stem cells that give rise to all the blood cell types including myeloid (e.g., monocytes and macrophages, granulocytes (e.g., neutrophils, basophils, eosinophils, and mast cells), erythrocytes, megakaryocytes/platelets, dendritic cells), and lymphoid lineages (e.g., T cells, B cells, and NK cells) (see e.g., Doulatov et al., 2012; Notta et al., 2015). A "multilymphoid progenitor" (MLP) is defined to describe any progenitor that gives rise to all lymphoid lineages (e.g., B, T, and NK cells), but that may or may not have other (myeloid) potentials (Doulatov et al., 2010) and is CD45RA$^+$, /CD10$^+$/CD7$^-$. Any B, T, and NK progenitor can be referred to as an MLP. A "common myeloid progenitor" (CMP) refers to CD45RA$^-$/CD135$^+$/CD10$^-$/CD7$^-$ cells that can give rise to granulocytes, monocytes, megakaryocytes and erythrocytes.

"Pluripotent stem cell (PSC)" refers to a stem cell that has the potential to differentiate into all cells constituting one or more tissues or organs, or preferably, any of the three germ layers: endoderm (e.g., interior stomach lining, gastrointestinal tract, the lungs), mesoderm (e.g., muscle, bone, blood, urogenital), or ectoderm (e.g., epidermal tissues and nervous system).

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation.

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming.

"Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Typically, transdifferentiation by programming occurs without the cells passing through an intermediate pluripotency stage—i.e., the cells are programmed directly from one differentiated cell type to another differentiated cell type. Under certain conditions, the proportion of progeny with characteristics of the new cell type may be at least about 1%, 5%, 25% or more in order of increasing preference.

The term "forward programming" refers to the programming of a multipotent or pluripotent cell, as opposed to a differentiated somatic cell that has no pluripotency, by the provision of one or more specific lineage-determining genes or gene products to the multipotent or pluripotent cell. For example, forward programming may describe the process of programming ESCs or iPSCs to hematopoietic precursor cells or other precursor cells, or to hematopoietic cells or other differentiated somatic cells.

As used herein, the term "subject" or "subject in need thereof" refers to a mammal, preferably a human being, male or female at any age that is in need of a cell or tissue transplantation. Typically the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation.

As used herein, a "disruption" of a gene refers to the elimination or reduction of expression of one or more gene products encoded by the subject gene in a cell, compared to the level of expression of the gene product in the absence of the disruption. Exemplary gene products include mRNA and protein products encoded by the gene. Disruption in some cases is transient or reversible and in other cases is permanent. Disruption in some cases is of a functional or full length protein or mRNA, despite the fact that a truncated or non-functional product may be produced. In some embodiments herein, gene activity or function, as opposed to expression, is disrupted. Gene disruption is generally induced by artificial methods, i.e., by addition or introduction of a compound, molecule, complex, or composition, and/or by disruption of nucleic acid of or associated with the gene, such as at the DNA level. Exemplary methods for gene disruption include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination. Examples include insertions, mutations, and deletions. The disruptions typically result in the repression and/or complete absence of expression of a normal or "wild type" product encoded by the gene. Exemplary of such gene disruptions are insertions, frameshift and missense mutations, deletions, knock-in, and knock-out of the gene or part of the gene, including deletions of the entire gene. Such disruptions can occur in the coding region, e.g., in one or more exons, resulting in the inability to produce a full-length product, functional product, or any product, such as by insertion of a stop codon. Such disruptions may also occur by disruptions in the promoter or enhancer or other region affecting activation of transcription, so as to prevent transcription of the gene. Gene disruptions include gene targeting, including targeted gene inactivation by homologous recombination.

"Notch ligand" is a protein capable of binding to a Notch receptor polypeptide present in the membrane of a number of different mammalian cells such as hematopoietic stem cells. The Notch receptors that have been identified in human cells include Notch-1, Notch-2, Notch-3, and Notch-4. Notch ligands typically have a diagnostic DSL domain (D-Delta, S-Serrate, and L-Lag2) comprising 20 to 22 amino acids at the amino terminus and between 3 to 8 EGF-like repeats (Furie and Furie, 1988; Knust et al., 1987; Suzuki et al., 1987) on the extracellular surface.

II. PLURIPOTENT STEM CELLS

In certain embodiments of the present disclosure, there are disclosed methods and compositions for providing multilineage HPCs, DE cells, or EPCs from PSCs. The PSCs may be stem cells including but are not limited to, iPSCs and embryonic stem cells (ESCs).

The PSCs used in the present method to produce HPCs or EPCs are characterized by the ability to renew themselves through mitotic cell division and the ability to differentiate into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, and also maintain the normal turnover of regenerative organs, such as blood, skin or intestinal tissues.

In particular aspects, the PSCs used herein are human ESCs or iPSCs which are capable of long-term proliferation in vitro, while retaining the potential to differentiate into all cell types of the body, including the HPCs, DE cells, or EPCs of the present disclosure. Thus, these cells could potentially provide an unlimited supply of patient-specific functional cells for both drug development and therapeutic uses. Certain aspects provide multi-lineage HPCs, DE cells, or EPCs by forward programming from human PSCs such as ESCs and iPSCs via expression of a combination of programming genes.

A. Embryonic Stem Cells

In certain aspects, the PSCs are embryonic stem cells (ESCs). ES cells are derived from the inner cell mass of blastocysts and have a high in vitro differentiating capability. ES cells can be isolated by removing the outer trophectoderm layer of a developing embryo, then culturing the inner mass cells on a feeder layer of non-growing cells. The replated cells can continue to proliferate and produce new colonies of ES cells which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913). ES cells have the potential to proliferate while maintaining their pluripotency. For example, ES cells are useful in research on cells and on genes which control cell differentiation. The pluripotency of ES cells combined with genetic manipulation and selection can be used for gene analysis studies in vivo via the generation of transgenic, chimeric, and knockout mice.

Methods for producing mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001).

ES cells can also be derived from other organisms including rhesus monkey and marmoset by previously described methods (Thomson and Marshall, 1998; Thomson et al., 1995; Thomson and Odorico, 2000; U.S. Pat. No. 5,843, 780), as well as from established mouse and human cell lines. For example, established human ES cell lines include MAOI, MA09, ACT-4, HI, H7, H9, H13, H14 and ACT30. As a further example, mouse ES cell lines that have been established include the CGR8 cell line established from the inner cell mass of the mouse strain 129 embryos, and cultures of CGR8 cells can be grown in the presence of LIF without feeder layers.

ES stem cells can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

B. Induced Pluripotent Stem Cells

In other aspects, the PSCs used herein are induced pluripotent stem (iPS) cells, commonly abbreviated iPS cells or iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of germ cells, any cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648; U.S. Publication No. 2015/0191697). There is no limitation on the degree of cell differentiation or the age of an animal from which cells are collected; even undifferentiated progenitor cells (including somatic stem cells) and finally differentiated mature cells can be used as sources of somatic cells in the methods disclosed herein. iPS cells can be grown under conditions that are known to differentiate human ES cells into specific cell types, and express human ES cell markers including: SSEA-1, SSEA-3, SSEA-4, TRA-1-60, and TRA-1-81.

Somatic cells can be reprogrammed to produce iPS cells using methods known to one of skill in the art. One of skill in the art can readily produce iPS cells, see for example, Published U.S. Patent Application No. 2009/0246875, Published U.S. Patent Application No. 2010/0210014; Published U.S. Patent Application No. 2012/0276636; U.S. Pat. Nos. 8,058,065; 8,129,187; PCT Publication NO. WO 2007/069666 A1, U.S. Pat. Nos. 8,268,620; 8,546,140; 9,175,268; 8,741,648; U.S. Patent Application No. 2011/0104125, and U.S. Pat. No. 8,691,574, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized or Oct3/4, Sox2, Nanog, and Lin28.

Mouse and human cDNA sequences of these nuclear reprogramming substances are available with reference to the NCBI accession numbers mentioned in WO 2007/069666 and U.S. Pat. No. 8,183,038, which are incorporated herein by reference. Methods for introducing one or more reprogramming substances, or nucleic acids encoding these reprogramming substances, are known in the art, and disclosed for example, in U.S. Pat. Nos. 8,268,620, 8,691,574, 8,741,648, 8,546,140, in published U.S. Pat. Nos. 8,900,871 and 8,071,369, which are both incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF. Other methods for the culture and maintenance of iPSCs, as would be known to one of skill in the art, may be used with the methods disclosed herein.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™/Essential 8™ medium (Chen et al., 2011).

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments, plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. In particular aspects, the plasmids do not comprise a tyrosinase enhancer or promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, and U.S. application Ser. No. 12/478,154 which are incorporated herein by reference.

An episomal gene delivery system can be a plasmid, an Epstein-Barr virus (EBV)-based episomal vector (U.S. Pat. No. 8,546,140), a yeast-based vector, an adenovirus-based vector, a simian virus 40 (SV40)-based episomal vector, a bovine papilloma virus (BPV)-based vector, or a lentiviral vector. A viral gene delivery system can be an RNA-based or DNA-based viral vector (PCT/JP2009/062911, PCT/JP2011/069588).

C. Embryonic Stem Cells Derived by Somatic Cell Nuclear Transfer

PSCs for producing the HPCs, DE cells, or EPCs could also be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo.

III. METHYL-CPG BINDING PROTEIN 2 GENE DISRUPTION

In certain aspects, MeCP2 gene expression, activity or function is disrupted in cells, such as PSCs (e.g., ESCs or iPSCs). In some embodiments, the gene disruption is carried out by effecting a disruption in the gene, such as a knock-out, insertion, missense or frameshift mutation, such as biallelic frameshift mutation, deletion of all or part of the gene, e.g., one or more exon or portion therefore, and/or knock-in. For example, the disruption can be effected be sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of the MeCP2 gene or a portion thereof.

In some embodiments, the disruption of the expression, activity, and/or function of the gene is carried out by disrupting the gene. In some aspects, the gene is disrupted so that its expression is reduced by at least at or about 20, 30, or 40%, generally at least at or about 50, 60, 70, 80, 90, or 95% as compared to the expression in the absence of the gene disruption or in the absence of the components introduced to effect the disruption.

In some embodiments, the disruption is transient or reversible, such that expression of the gene is restored at a later time. In other embodiments, the disruption is not reversible or transient, e.g., is permanent.

In some embodiments, gene disruption is carried out by induction of one or more double-stranded breaks and/or one or more single-stranded breaks in the gene, typically in a targeted manner. In some embodiments, the double-stranded or single-stranded breaks are made by a nuclease, e.g., an endonuclease, such as a gene-targeted nuclease. In some aspects, the breaks are induced in the coding region of the gene, e.g., in an exon. For example, in some embodiments, the induction occurs near the N-terminal portion of the coding region, e.g., in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the gene. For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/or a premature stop codon results in disruption of the expression, activity, and/or function of the gene.

In some embodiments, gene disruption is achieved using antisense techniques, such as by RNA interference (RNAi), short interfering RNA (siRNA), short hairpin (shRNA), and/or ribozymes are used to selectively suppress or repress expression of the gene. siRNA technology is RNAi which employs a double-stranded RNA molecule having a sequence homologous with the nucleotide sequence of mRNA which is transcribed from the gene, and a sequence complementary with the nucleotide sequence. siRNA generally is homologous/complementary with one region of mRNA which is transcribed from the gene, or may be siRNA including a plurality of RNA molecules which are homologous/complementary with different regions. In some aspects, the siRNA is comprised in a polycistronic construct. In particular aspects, the siRNA suppresses both wild-type and mutant MeCP2 translation from endogenous mRNA.

In some aspects, the gene disruption is carried out by the administration of a pharmacological drug or small molecule inhibitor of MeCP2. There is a link between DNA methylation and the deacetylation of chromatin. There are both histone deacetylase (HDAC)-dependent and HDAC-independent modes of transcriptional repression by MeCP2. Thus, HDAC inhibitors such as trichostatin A (TSA) or Valproic acid can be used to disrupt MeCP2. In addition, protein inhibitors, DNA binding proteins that inhibit transcription, and proteins that bind to MeCP2 protein and inhibit function may be used. Further, in differentiated female mouse embryonic stem cells, a PDPK1 inhibitor decreased Xist levels and increased MeCP2 mRNA levels compared with vehicle (Bhatnagar et al., 2014).

A. Endonucleases

In some embodiments, the disruption is achieved using a DNA-targeting molecule, such as a DNA-binding protein or DNA-binding nucleic acid, or complex, compound, or composition, containing the same, which specifically binds to or hybridizes to the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease. Zinc finger, TALE, and CRISPR system binding domains can be engineered to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 2011/0301073.

In some embodiments, the DNA-targeting molecule, complex, or combination contains a DNA-binding molecule and one or more additional domain, such as an effector domain to facilitate the repression or disruption of the gene. For example, in some embodiments, the gene disruption is carried out by fusion proteins that comprise DNA-binding proteins and a heterologous regulatory domain or functional fragment thereof. In some aspects, domains include, e.g., transcription factor domains such as activators, repressors, co-activators, co-repressors, silencers, oncogenes, DNA repair enzymes and their associated factors and modifiers, DNA rearrangement enzymes and their associated factors and modifiers, chromatin associated proteins and their modifiers, e.g. kinases, acetylases and deacetylases, and DNA modifying enzymes, e.g. methyltransferases, topoisomerases, helicases, ligases, kinases, phosphatases, polymerases, endonucleases, and their associated factors and modifiers. See, for example, U.S. Patent Application Publication Nos. 2005/0064474; 2006/0188987 and 2007/0218528, incorporated by reference in their entireties herein, for details regarding fusions of DNA-binding domains and nuclease cleavage domains. In some aspects, the additional domain is a nuclease domain. Thus, in some embodiments, gene disruption is facilitated by gene or genome editing, using engineered proteins, such as nucleases and nuclease-containing complexes or fusion proteins, composed of sequence-specific DNA-binding domains fused to or complexed with non-specific DNA-cleavage molecules such as nucleases.

In some aspects, these targeted chimeric nucleases or nuclease-containing complexes carry out precise genetic modifications by inducing targeted double-stranded breaks or single-stranded breaks, stimulating the cellular DNA-repair mechanisms, including error-prone nonhomologous end joining (NHEJ) and homology-directed repair (HDR). In some embodiments the nuclease is an endonuclease, such as a zinc finger nuclease (ZFN), TALE nuclease (TALEN), and RNA-guided endonuclease (RGEN), such as a CRISPR-associated (Cas) protein, or a meganuclease.

In some embodiments, a donor nucleic acid, e.g., a donor plasmid or nucleic acid encoding the genetically engineered antigen receptor, is provided and is inserted by HDR at the site of gene editing following the introduction of the DSBs. Thus, in some embodiments, the disruption of the gene and the introduction of the antigen receptor, e.g., CAR, are carried out simultaneously, whereby the gene is disrupted in part by knock-in or insertion of the CAR-encoding nucleic acid.

In some embodiments, no donor nucleic acid is provided. In some aspects, NHEJ-mediated repair following introduction of DSBs results in insertion or deletion mutations that can cause gene disruption, e.g., by creating missense mutations or frameshifts.

1. ZFPs and ZFNs

In some embodiments, the DNA-targeting molecule includes a DNA-binding protein such as one or more zinc finger protein (ZFP) or transcription activator-like protein (TAL), fused to an effector protein such as an endonuclease. Examples include ZFNs, TALEs, and TALENs. See Lloyd et al, 2013.

In some embodiments, the DNA-targeting molecule comprises one or more zinc-finger proteins (ZFPs) or domains thereof that bind to DNA in a sequence-specific manner. A ZFP or domain thereof is a protein or domain within a larger protein that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP. Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice. See, for example, Beerli et al., 2002; Pabo et al., 2001; Isalan et al., 2001; Segal et al., 2001; Choo et al., 2000; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

In some aspects, disruption of MeCP2 is carried out by contacting a first target site in the gene with a first ZFP, thereby disrupting the gene. In some embodiments, the target site in the gene is contacted with a fusion ZFP comprising six fingers and the regulatory domain, thereby inhibiting expression of the gene.

In some embodiments, the step of contacting further comprises contacting a second target site in the gene with a second ZFP. In some aspects, the first and second target sites are adjacent. In some embodiments, the first and second ZFPs are covalently linked. In some aspects, the first ZFP is a fusion protein comprising a regulatory domain or at least two regulatory domains.

In some embodiments, the first and second ZFPs are fusion proteins, each comprising a regulatory domain or each comprising at least two regulatory domains. In some embodiments, the regulatory domain is a transcriptional repressor, a transcriptional activator, an endonuclease, a methyl transferase, a histone acetyltransferase, or a histone deacetylase.

In some embodiments, the ZFP is encoded by a ZFP nucleic acid operably linked to a promoter. In some aspects, the method further comprises the step of first administering the nucleic acid to the cell in a lipid:nucleic acid complex or as naked nucleic acid. In some embodiments, the ZFP is encoded by an expression vector comprising a ZFP nucleic acid operably linked to a promoter. In some embodiments, the ZFP is encoded by a nucleic acid operably linked to an inducible promoter. In some aspects, the ZFP is encoded by a nucleic acid operably linked to a weak promoter.

In some embodiments, the target site is upstream of a transcription initiation site of the gene. In some aspects, the target site is adjacent to a transcription initiation site of the gene. In some aspects, the target site is adjacent to an RNA polymerase pause site downstream of a transcription initiation site of the gene.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type liS restriction enzyme and one or more zinc finger binding domains, which may or may not be engineered. In some embodiments, the cleavage domain is from the Type liS restriction endonuclease Fok I. Fok I generally catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al., 1992; Li et al., 1993; Kim et al., 1994a; Kim et al., 1994b. 269:31, 978-31, 982.]

In some embodiments, ZFNs target a gene present in the engineered cell. In some aspects, the ZFNs efficiently generate a double strand break (DSB), for example at a predetermined site in the coding region of the gene. Typical regions targeted include exons, regions encoding N terminal regions, first exon, second exon, and promoter or enhancer regions. In some embodiments, transient expression of the ZFNs promotes highly efficient and permanent disruption of the target gene in the engineered cells. In particular, in some embodiments, delivery of the ZFNs results in the permanent disruption of the gene with efficiencies surpassing 50%.

Many gene-specific engineered zinc fingers are available commercially. For example, Sangamo Biosciences (Richmond, Calif., USA) has developed a platform (CompoZr) for zinc-finger construction in partnership with Sigma-Aldrich (St. Louis, Mo., USA), allowing investigators to bypass zinc-finger construction and validation altogether, and provides specifically targeted zinc fingers for thousands of proteins (Gaj et al., Trends in Biotechnology, 2013, 31(7), 397-405). In some embodiments, commercially available zinc fingers are used or are custom designed. (See, for example, Sigma-Aldrich catalog numbers CSTZFND, CSTZFN, CTil-1KT, and PZD0020).

2. TALs, TALEs and TALENs

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 2011/0301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Di-residue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NO binds to T and non-canonical (atypical) RVDs are also known. See, U.S. Patent Publication No. 2011/0301073. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE nuclease (TALEN). In some aspects the TALEN is a fusion protein comprising a DNA-binding domain derived from a TALE and a nuclease catalytic domain to cleave a nucleic acid target sequence.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation (Critchlow and Jackson, 1998) or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., 2013). A library of TALENs targeting 18,740 human protein-coding genes has been constructed (Kim et al., 2013). Custom-designed TALE arrays are commercially available through Cellectis Bioresearch (Paris, France), Transposagen Biopharmaceuticals (Lexington, Ky., USA), and Life Technologies (Grand Island, N.Y., USA). Specifically, TALENs that target CD38 are commercially available (See Gencopoeia, catalog numbers HTN222870-1, HTN222870-2, and HTN222870-3). Exemplary molecules are described, e.g., in U.S. Patent Publication Nos. US 2014/0120622, and 2013/0315884.

In some embodiments the TALEN s are introduced as trans genes encoded by one or more plasmid vectors. In some aspects, the plasmid vector can contain a selection marker which provides for identification and/or selection of cells which received said vector.

3. RGENs (CRISPR/Cas Systems)

In some embodiments, the disruption is carried out using one or more DNA-binding nucleic acids, such as disruption via an RNA-guided endonuclease (RGEN). For example, the disruption can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2.

The CRISPR enzyme can be Cas9 (e.g., from S. pyogenes or S. pneumonia). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

B. Delivery of Nucleic Acids

In some aspects, a nucleic acid encoding the DNA-targeting molecule, complex, or combination, is administered or introduced to the cell. The nucleic acid typically is administered in the form of an expression vector, such as a viral expression vector. In some aspects, the expression vector is a retroviral expression vector, an adenoviral expression vector, a DNA plasmid expression vector, or an AAV expression vector. In some aspects, one or more polynucleotides encoding the disruption molecule or complex, such as the DNA-targeting molecule, is delivered to the cell. In some aspects, the delivery is by delivery of one or more vectors, one or more transcripts thereof, and/or one or more proteins transcribed therefrom, is delivered to the cell.

In some embodiments, the polypeptides are synthesized in situ in the cell as a result of the introduction of polynucleotides encoding the polypeptides into the cell. In some aspects, the polypeptides could be produced outside the cell and then introduced thereto. Methods for introducing a polynucleotide construct into animal cells are known and include, as non-limiting examples stable transformation methods wherein the polynucleotide construct is integrated into the genome of the cell, transient transformation methods wherein the polynucleotide construct is not integrated into the genome of the cell, and virus mediated methods. In some embodiments, the polynucleotides may be introduced into the cell by for example, recombinant viral vectors (e.g. retroviruses, adenoviruses), liposome and the like. For example, in some aspects, transient transformation methods include microinjection, electroporation, or particle bombardment. In some embodiments, the polynucleotides may be included in vectors, more particularly plasmids or virus, in view of being expressed in the cells.

In some embodiments, viral and non-viral based gene transfer methods can be used to introduce nucleic acids in mammalian cells or target tissues. Such methods can be used to administer nucleic acids encoding components of a CRISPR, ZFP, ZFN, TALE, and/or TALEN system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, 1992; Nabel & Feigner, 1993; Mitani & Caskey, 1993; Dillon, 1993; Miller, 1992; Van Brunt, 1988; Vigne, 1995; Kremer & Perricaudet, 1995; Haddada et al., 1995; and Yu et al., 1994.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in (e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91117424; WO 91116024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer.

In some aspects, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP), may be introduced into the cell to encode a gene product which serves as a marker by which to measure the alteration or modification of expression of the gene product. In a further embodiment, the DNA molecule encoding the gene product may be introduced into the cell via a vector. In some embodiments, the gene product is luciferase.

In certain embodiments, the transgene cassette is integrated through the use of transposase systems. A transposable element (TE or transposon) is a DNA sequence that can change its position within the genome, sometimes creating or reversing mutations and altering the cell's genome size. Transposons can be used in genetic research and recombinant genetic engineering for insertional mutagenesis. Insertional mutagenesis is when transposons function as vectors to help remove and integrate genetic sequences. Given their relatively simple design and inherent ability to move DNA sequences, transposons are highly compatible at transducing genetic material, making them ideal genetic tools. Generally, transposase systems include Sleeping Beauty, miniTol2 and PiggyBac.

A miniTol2 plasmid system (Balciunas et al., 2006) may be used for integration of the transgene. In the two-plasmid system, one plasmid contains the terminal Tol2 sequences flanking the promoter driving the reporter gene and the other plasmid (pTrans) contains the transposase sequence under the control of another promoter. Promoters for use in the miniTol2 plasmid system can be the pCAGGS promoter, the CMV IE promoter. In this system, the miniTol-reporter gene sequence is incorporated into the target genomic DNA while the pTrans sequence will not be incorporated.

The PiggyBac transposon which is a mobile genetic element that efficiently transposes between vectors and chromosomes via a "cut and paste" mechanism may be used. During transposition, the Super PB transposase recognizes transposon-specific inverted terminal repeat sequences (ITRs) located on both ends of the transposon vector and moves the contents from the original sites and efficiently integrates them into TTAA chromosomal sites. The powerful activity of the PiggyBac transposon system enables genes of interest between the two ITRs in the PB vector to be easily mobilized into target genomes.

IV. PRODUCTION OF MATURE LINEAGE CELLS

In some embodiments, the present disclosure provides iPSC cells with MeCP2 disruption, such as MeCP2KO, which may be differentiated to mature lineages, such as through HPCs, DE cells, or EPCs. The HPCs may be further differentiated to erythroid, lymphoid or myeloid lineages with a high efficiency and purity. For example, the HPCs may be used to generate mature erythrocytes or microglia as well as cells of the lymphoid lineage, such as T cells, B cells, NK cells, and T/NK cells. The DE cells or EPCs may be further differentiated to cells of the endoderm lineage such as β cells and hepatocytes.

The present studies also support the role of demethylation with the onset of maturity in iPSC-derived lineages. In the mammalian genome, approximately 60% to 90% of CpGs are methylated. The remaining unmethylated CpGs are clustered into what are termed CpG islands, which comprise around 1% of the genome. Proteins of the methyl-CpGbinding domain (MBD) family recruit chromatin remodelers, histone deacetylases and methylases to act on methylated DNA leading to epigenetic remodeling and transcriptional repression. They essentially function as biological clocks to organize the chromatin and orchestrate coherent transcription in response to niche dependent signals (Bird, 1986; Jones and Takai, 2001). The present studies showed that knocking out MeCP2 in iPSCs alters the methylation status that manipulates the biological clock within the cells to generate mature lineages in vitro. Thus, it offers a window to include transient stage-specific demethylation (via small molecules, RNAi, or compounds) steps during differentiation to generate mature lineages from iPSC in vitro. This finding could be unique to iPSCs due to their primed developmental stage and the unique in vitro differentiation environment. Accordingly, in some embodiments, the present disclosure provides methods of altering iPSC methylation status by disrupting MeCP2 in order to provide iPSCs which can be differentiated to cells of mature lineages efficiently.

A. Production of HPCs

The PSCs (e.g., ES cells or iPS cells) engineered to have disruption of MeCP2 can be differentiated into HPCs by methods known in the art such as described in U.S. Pat. No. 8,372,642, which is incorporated by reference herein. For example, combinations of BMP4, VEGF, Flt3 ligand, IL-3, and GMCSF may be used to promote hematopoietic differentiation. In certain embodiments, the sequential exposure of cell cultures to a first media that includes BMP4 and VEGF (and optionally FGF-2), followed by culture in a second media that includes Flt3 ligand, SCF, TPO, IL-3, and IL-6 can differentiate pluripotent cells into hematopoietic precursor cells and hematopoietic cells. Further, inclusion of FGF-2 (50 ng/ml) in the media containing BMP4 and VEGF can enhance the efficiency of the generation of hematopoietic precursor cells from pluripotent cells.

Differentiation of pluripotent cells into HPCs may be performed using defined or undefined conditions. Generally, it will be appreciated that defined conditions are generally preferable in embodiments where the resulting cells are intended to be administered to a human subject. HPCs may be cultured from PSCs under defined conditions (e.g., using a TeSR media and a matrix component such as Matrigel™), and hematopoietic cells may be generated from embryoid bodies derived from the pluripotent cells. In other embodiments, pluripotent cells may be co-cultured on OP9 cells or mouse embryonic fibroblast cells and subsequently differentiated.

Pluripotent cells may be allowed to form embryoid bodies or aggregates as a part of the differentiation process. The formation of "embryoid bodies" (EBs), or clusters of growing cells, in order to induce differentiation generally involves in vitro aggregation of human pluripotent stem cells into EBs and allows for the spontaneous and random differentiation of human pluripotent stem cells into multiple tissue types that represent endoderm, ectoderm, and mesoderm origins. Three-dimensional EBs can thus be used to produce some fraction of hematopoietic cells and endothelial cells.

EBs may be formed using the following protocol. Undifferentiated hESC or iPSC adapted to feeder free growth on Matrigel™ or Vitronectin Coated Plates May be harvested at confluence using 0.5 mM EDTA treatment for about 8-10 minutes at room temperature. The EDTA is aspirated after the incubation and the EBs may be formed by collecting the cells in EB basal media containing rock inhibitor or blebbistatin. The media may be changed the next day to EB differentiation media containing different cytokine formulations. The cells are placed at a density of 0.25-0.5 million cells per ml to promote aggregate formation.

To promote EB formation, the cells may be transferred to low-attachment plates for an overnight incubation in serum-free differentiation (SFD) medium, consisting of 75% IMDM (Gibco), 25% Ham's Modified F12 (Cellgro) supplemented with 0.5% N2 and 1% B-27 without RA supplements, 200 mM l-glutamine, 0.05 mg/ml Ascorbic Acid-2-phosphate Magnesium Salt (Asc 2-P) (WAKO), GlutaMAX, Pen/Strep, and $4.5 \times 10^{-4}$ MTG as previously described (Nat Biotechnol. 2006 November; 24(11):1402-11) The next day the cells may be collected from each well and centrifuged. The cells may then be resuspended in "EB differentiation media," which consists of SFD basal media supplemented with about 50 ng/ml bone morphogenetic factor (BMP-4), about 50 ng/ml vascular endothelial growth factor (VEGF), and 50 ng/ml zb FGF for the first four days of differentiation. The cells are half fed every 48 hrs. On the fifth day of differentiation the media is replaced with a second media comprised of SFD media supplemented with 50 ng/ml stem cell factor (SCF), 50 ng/ml Flt-3 ligand (Flt-3L), 50 ng/ml interleukin-6 (IL-6), IL-3, 50 ng/mL, and 50 ng/ml thrombopoieitin (TPO). The cells are half fed every 48 hours with fresh differentiation media. The media changes are performed by spinning down the differentiation cultures at 300 g for 5 minutes and aspirating half the volume from the differentiating cultures and replenishing it with the same volume of fresh media. In certain embodiments, the EB differentiation media may include BMP4 (e.g., about 50 ng/ml), VEGF (e.g., about 50 ng/ml), and optionally FGF-2 (e.g., about 25-75 ng/ml or about 50 ng/ml). The supernatant may be aspirated and replaced with fresh differentiation medium. Alternately the cells may be half fed every two days with fresh media. The cells may be harvested at different time points during the differentiation process.

HPCs may be cultured from PSCs using a defined medium. Methods for the differentiation of pluripotent cells into hematopoietic CD34+ stem cells using a defined media are described, e.g., in U.S. application Ser. No. 12/715,136 which is incorporated by reference in its entirety without disclaimer. It is anticipated that these methods may be used with the present disclosure.

For example, a defined medium may be used to induce hematopoietic CD34+ differentiation. The defined medium may contain the growth factors BMP-4, VEGF, Flt3 ligand, IL-3 and/or GMCSF. Pluripotent cells may be cultured in a first defined media comprising BMP4, VEGF, and optionally FGF-2, followed by culture in a second media comprising either (Flt3 ligand, IL-3, and GMCSF) or (Flt3 ligand, IL-3, IL-6, and TPO). The first and second media may also comprise one or more of SCF, IL-6, G-CSF, EPO, FGF-2, and/or TPO. Substantially hypoxic conditions (e.g., less than 20% O2) may further promote hematopoietic or endothelial differentiation.

Cells may be substantially individualized via mechanical or enzymatic means (e.g., using a trypsin or TrypLE™). A ROCK inhibitor (e.g., H1152 or Y-27632) may also be included in the media. It is anticipated that these approaches may be automated using, e.g., robotic automation. iPSCs may be conditioned by culturing them under hypoxic conditions.

In certain embodiments, substantially hypoxic conditions may be used to promote differentiation of pluripotent cells into hematopoietic progenitor cells. As would be recognized by one of skill in the art, an atmospheric oxygen content of less than about 20.8% would be considered hypoxic. Human cells in culture can grow in atmospheric conditions having reduced oxygen content as compared to ambient air. This relative hypoxia may be achieved by decreasing the atmospheric oxygen exposed to the cells in culture. Embryonic cells typically develop in vivo under reduced oxygen conditions, generally between about 1% and about 6% atmospheric oxygen, with carbon dioxide at ambient levels. Without wishing to be bound by theory, it is anticipated that hypoxic conditions may mimic an aspect of certain embryonic developmental conditions. As shown in the below examples, hypoxic conditions can be used in certain embodiments to promote additional differentiation of pluripotent cells, such as iPSC or hESC, into a more differentiated cell type, such as hematopoietic precursor cells.

The following hypoxic conditions may be used to promote differentiation of pluripotent cells into hematopoietic progenitor cells. In certain embodiments, an atmospheric oxygen content of less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, about 5%, about 4%, about 3%, about 2%, or about 1% may be used to promote differentiation into hematopoietic precursor cells. In certain embodiments, the hypoxic atmosphere comprises about 5% oxygen gas.

Regardless of the specific medium being used in any given hematopoietic progenitor cell expansion, the medium used is preferably supplemented with at least one cytokine at a concentration from about 0.1 ng/mL to about 500 ng/mL, more usually 10 ng/mL to 100 ng/mL. Suitable cytokines, include but are not limited to, c-kit ligand (KL) (also called steel factor (StI), mast cell growth factor (MGF), and stem cell factor (SCF)), IL-6, G-CSF, IL-3, GM-CSF, IL-1α, IL-11, MIP-1α, LIF, c-mpl ligand/TPO, and flk2/flk3 ligand (Flt2L or Flt3L) (Nicola et al., 1979; Golde et al., 1980; Lusis, 1981; Abboud et al., 1981; Okabe, 1982; Fauser et al., 1981). Particularly, the culture will include at least one of SCF, Flt3L and TPO. More particularly, the culture will include SCF, Flt3L and TPO.

In one embodiment, the cytokines are contained in the media and replenished by media perfusion. Alternatively, when using a bioreactor system, the cytokines may be added separately, without media perfusion, as a concentrated solution through separate inlet ports. When cytokines are added without perfusion, they will typically be added as a 10× to 100× solution in an amount equal to one-tenth to 1/100 of the volume in the bioreactors with fresh cytokines being added approximately every 2 to 4 days. Further, fresh concentrated cytokines also can be added separately, in addition to cytokines in the perfused media.

A. Erythroid Differentiation

HPCs may be differentiated into erythroid cells using, e.g., an erythroid differentiation medium. An erythroid differentiation medium may be a serum-free or defined medium, and the medium may contain SCF, EPO, TPO, insulin, dexamethasone or hydrocortisone, and transferrin (Slukvin et al., 2007). Erythroid progenitors may be generated by placing the hematopoietic precursor cells with disruption of MeCP2 in media containing hydrocortisone, holotransferrin, and EXCYTE®.

In one exemplary method, HPCs are transferred in low attachment plates to a medium containing SFEM (Stem Cell Technologies), heparin (e.g., 1 to 10 U/mL, such as 5 U/mL, Sigma), TPO (e.g., 50 to 150 ng/mL, such as 100 ng/mL), human recombinant SCF (e.g., 50 to 150 ng/mL, such as 100 ng/mL), FLT3L (e.g., 50 to 150 ng/mL, such as 100 ng/mL), IL-3 (e.g., 1 to 20 ng/mL, such as 10 ng/mL), and IL-6 (e.g., 1 to 20 ng/mL, such as 10 ng/mL). After about 4-6 days erythroid cells are expanded in SFEM medium containing 0.1% to 0.5% Excyte, such as 0.3% Excyte (Serologicals), Holo-Transferrin (e.g., 0.5 to 5 mg/mL, such as 1 mg/mL, Sigma), Hydrocortisone (e.g., 0.5 to 5 mM, such as 1 mM, Sigma), Insulin (e.g., 5 to 50 ng/mL, such as 20 ng/mL, Sigma), SCF (e.g., 10 to 100 ng/mL, such as 50 ng/mL, R&D Systems), EPO (e.g., 1 to 5 U/mL, such as 2 U/mL, R&D Systems), IL-3 (e.g., 1 to 10 ng/mL, such as 5 ng/mL), IL-6 (e.g., 1 to 25 ng/mL, such as 10 ng/mL) and TPO (e.g., 10 to 100 ng/mL, such as 50 ng/mL), for an additional 2-3 weeks. Subsequently, IL-3, IL-6 and TPO are removed from the medium and the cells are cultured in the presence of SCF and EPO. The presence of erythroblasts in the cell suspension is quantified by surface staining CD235a (glycophorin A), CD36, and CD71 by flow cytometry.

Methylcellulose may be used to induce differentiation of erythrocytes, macrophages and/or granulocytes from HPCs. Methylcellulose is a relatively inert polymer that forms a stable gel with good optical clarity. It is commonly used at a final concentration of 0.9-1.2% in culture medium supplemented with compounds including fetal bovine serum (FBS), bovine serum albumin (BSA), 2-mercaptoethanol, insulin, transferrin and recombinant cytokines or conditioned medium as a source of colony-stimulating factors. Methods involving methylcellulose differentiation of cells are described, e.g., in Kaufman et al. (2001).

Methylcellulose-based medium permits better growth of erythroid lineage cells than other types of semi-solid matrices, thus allowing the assay of erythroid, granulocyte, monocyte and multi-potential CFCs within the same culture. Megakaryocyte progenitors are suitably cultured in supplemented collagen-based medium and specifically identified using immunocytochemical staining.

An erythroid cell generated by the methods described may be characterized by expression of one or more hematopoietic/erythroid markers selected from the group consisting of: CD31; CD34; CD36; CD41a; CD43; CD45; CD71; and CD235a. Additionally, erythroid cells may be characterized by evaluation of the expression of globins including embryonic (epsilon) and fetal (gamma) and adult (beta) globins. In particular aspects, the mature erythroid cells will have higher expression of β-globin as compared to expression of γ-globin and ε-globin. Wright staining can be performed with cytospins of the cells to confirm the enucleated morphology of erythroblasts. The erythroid cells can also be co-stained for various globins with the cell surface marker CD235.

B. Myeloid Differentiation

1. Megakaryocyte Differentiation

HPCs may be further differentiated into megakaryocytes. In the body, megakaryocytes are found in the blood marrow and produce platelets from processes, or proplatelets, which form on the cells. Megakaryocyte cells in the human body only represent a small fraction of bone marrow cells but can increase in number up to 10-fold in response to certain diseases. In the body, megakaryocytes typically differentiate from hematopoietic cells as follows: hemacytoclasts differentiate into megakaryoblasts, megakaryoblasts then differentiate into promegakaryocytes, and promegakaryocytes then differentiate into megakaryocytes.

Various media and methods may be used to differentiate pluripotent cells or hematopoietic precursor cells into megakaryocytes. For example, methods and media for differentiating pluripotent cells into megakaryocytes as described in US 2007/0077654, which is incorporated by reference in its entirety without disclaimer, may be used with the present disclosure.

Growth factors are preferentially included in a megakaryocyte differentiation medium. For example, a megakaryocyte differentiation medium may contain one, two, three, four, or all of FLT-3 ligand, stem cell factor (SCF), thrombopoietin (TPO), interleukin-3 (IL-3), and interleukin-6 (IL-6). In certain embodiments, only SCF may be included in a megakaryocyte differentiation medium. In other embodiments, SCF may be used in combination with one or both of IL-3 and/or IL-6. In various embodiments, FLT-3 ligand and/or TPO may be excluded from a megakaryocyte differentiation medium of the present disclosure.

Hematopoietic cells may be differentiated into megakaryocytes by placing the hematopoietic precursor cells in media containing 100 ng/ml TPO, SCF, FLT-3, 20% BIT9500. A megakarocyte differentiation medium may be used to induce generation of megakarocytes. Various products and approaches for the generation of megakarocytes have been described and may be used with the present disclosure, such as described in WO2006/050330. Additionally, Megacult™ is available from Stem Cell Technologies and may be used for producing/differentiating megakaryocytes. In various embodiments, thrombopoeitin (TPO), interleukin 3 (IL-3), interleukin 6 (IL-6) and/or stem cell factor may be included in a megakarocyte differentiation medium. Methods for megakarocyte differentiation of cells are described, e.g., in Kaufman et al. (2001).

2. Mast Cell Generation

HPCs may be further differentiated into mast cells. Exposure of pluripotent stem cells to stem cell factor (SCF), IL-6, IL-3, IL-4, IL-9 and/or IL-10 may promote mast cell differentiation.

In certain embodiments, the following protocol may be used to promote differentiation into mast cells. Hematopoietic cells may be first differentiated into megakaryocytes by placing hematopoietic precursor cells in media "MK5" containing 100 ng/ml each of TPO, SCF, FLT-3, 20% BIT9500. Mast cells may be subsequently produced by expanding the precursor in MK5 expansion medium followed by 50 ng/ml SCF, 50 ng/ml IL-6 containing media.

In various embodiments, methods for differentiation of cord blood or peripheral blood into mast cells may also be used to promote megakaryocyte differentiation. For example, Schernthaner et al. (2001) describes methods for differentiating cord blood progenitors into mast cells using SCF in combination with IL-6 or a combination of IL-4, IL-6, and IL-10 at various time points. Lappalainen et al. (2007) provides methods for differentiating peripheral blood into mast cells by culturing cells using SCF and other cytokines (such as IL-3, IL-6, IL-9, and IL-4) added for various periods of time. It is anticipated that either of these methods may be successfully used with the present disclosure.

3. Macrophages and Dendritic Cells

Hematopoietic precursor cells may be further differentiated into dendritic cells. For example, hematopoietic precursor cells HPCs are transferred in low attachment plates to a medium containing SFEM (Stem Cell Technologies), heparin (e.g., 1 to 10 U/mL, such as 5 U/mL, Sigma), TPO (e.g., 50 to 150 ng/mL, such as 100 ng/mL), human recombinant SCF (e.g., 50 to 150 ng/mL, such as 100 ng/mL), FLT3L (e.g., 50 to 150 ng/mL, such as 100 ng/mL), IL-3 (e.g., 1 to 20 ng/mL, such as 10 ng/mL), and IL-6 (e.g., 1 to 20 ng/mL, such as 10 ng/mL) for 8 days. The cells are subsequently placed in the media containing 100 ng/ml GMCSF for 8 days to generate a common myeloid progenitor. These cells may then be further differentiated into either macrophages by placing the cells in M-CSF (20 ng/ml) and IL-1β (10 ng/ml) containing media for about 2 weeks, or dendritic cells by placing the cells in 20 ng/ml GMCSF, 20 ng/ml IL-4. The presence of macrophages that might emerge in the cultures can be quantified by staining for the presence of cell surface expression of CD163, CD14, CD68, and CD45.

4. Microglia Generation

The aggregates, such as from day 9 of HPC of differentiation, or $CD34^+/CD43^+$ magnetically sorted pure HPCs on Day 13 of HPC differentiation, may be plated on Matrigel coated plates at a cell density of 10-15 k/cm² to initiate microglia differentiation according to the method described by Abud et al., 2017. Microglia differentiation may be performed under normoxic conditions.

In one exemplary method, the cells are fed with microglia differentiation media containing 25 ng/ml MCSF, 50 ng/ml TGFβ, and 100 ug/ml IL-34 for the first 22 days of differentiation. The cells are then placed in microglia maturation media containing 25 ng/ml MCSF, 50 ng/ml TGFβ, 100 ug/ml IL-34, CD200 and CX3CL1. The cells are harvested on day 27 and stained for the presence of P2RY, TREM-2, IBA and CXC3CR1 by intracellular flow cytometry to confirm the emergence of microglia in end stage cultures.

C. Lymphoid Differentiation

The HPCs may also be further differentiated to the lymphoid lineage. In some aspects, HPCs isolated at day 7-11, such as day 7, day 8, day 9, day 10 or day 11 of the differentiation process can be differentiated to lymphoid cells such as T and NK cells. In some aspects, the timing of the origin for lymphoid progenitors coincides with the decline of hematoendothelial progenitors and the emergence of erythroid progenitors during HPC differentiation. In particular aspects, Day 9 HPCs may have an increased efficiency at generating T cells. HPCs capable of lymphoid differentiation can be isolated and/or identified by the expression of certain markers. For example, cells with surface expression of CD34 and/or CD43 may be selected for lymphoid differentiation. Additional markers for detecting lymphoid progenitors include DLL4, CD144, CD31, CD34, $CD43^{lo}$, $CD45^{lo/-}$, CD235, CD7, Flk-1, APNLR. In particular aspects, the presence of CD34/CD7, CD235/CD7, DLL4/CD34, DLL4/CD31, DLL4/CD144, or $CD34/CD43^{lo}$ double positive populations is used to identify lymphoid progenitors.

The HPCs may be cultured in defined, feeder free conditions for lymphoid differentiation. A culture media may contain one or more matrix components, such as RetroNectin, fibronectin or a RGD peptide. Without wishing to be bound by any theory, a matrix component may provide a solid support for the growth of embryonic stem cells. In certain embodiments, a matrix component may be applied to a culturing surface and contacted with culture media prior to seeding cells into the media. For example, cells may be cultured in a defined media (e.g., a TeSR media) on plates coated with fibronectin or Matrigel™ prior to mechanically separating the cells into clumps or individualizing cells and inducing differentiation into hematopoietic precursor cells.

Various matrix components may be used to culture pluripotent cells including a collagen (e.g., collagen IV), laminin, vitronectin, Matrigel™, gelatin, polylysine, thrombospondin (e.g., TSP-1, -2, -3, -4 and/or -5), and/or ProNectin-F™. In certain embodiments, the use of only Matriga™, collagen IV, or laminin with cells previously cultured using TeSR may be avoided due to possible adverse effects on cell viability; nonetheless, these compositions may be advantageously used in combination with other matrix components. Combinations of these matrix components may provide additional benefit for promoting cell growth and cell viability. In certain embodiments, 1, 2, 3, 4, 5, 6, or more of the above matrix components may be used to culture cells, e.g., prior to hematopoietic differentiation.

An exemplary feeder free matrix for lymphoid differentiation is disclosed in Example 4. In particular aspects, a non tissue culture-treated plate may be coated with DLL4:Fc chimera protein and RetroNectin (fibronectin fragment CH-296; Takara Shuzo, Japan) for use in lymphoid differentiation of HPCs.

In some embodiments, ascorbic acid may be used to enhance lymphoid differentiation. The defined media may be supplemented with about 10 µM to about 1 mM ascorbic acid, such as about 50 µM to about 100 µM, particularly about 95 µM.

1. T Cell Differentiation

In an aspect, the present disclosure provides a method for in vivo expansion of cells of the T cell lineage in a subject by modulating the differentiation of hematopoietic progenitor cells by altering the endogenous activity of a Notch ligand by administering a substance that increases the production of the Notch ligand in a subject. The method also includes culturing the cells in a medium, wherein the medium includes an effective amount of a notch ligand and one or more cytokines selected from the group consisting of IL-7, IL-11, SCF, Flt-3 and IL-3. In some particular embodiments, the medium can further include IL-6. In some embodiments, the notch ligand is delta4 notch ligand (DLL4), such as DLL4: Fc chimera. For example, the cultured cells may be monitored by flow cytometry for the development of T cells by staining the cells with anti-CD3 antibodies. The cells may be analyzed for the presence of T and NK cells using the cell surface markers CD4, CD8, CD3, CD94 and CD56. For example, cells which are $CD8^+$/$CD3^+$ would be indicative of differentiated T cells while NK cells would be $CD3^-$/$CD56^+$ and NK/T cells would be $CD3^+$/$CD56^+$.

A Notch ligand is selected that promotes and maintains differentiation and proliferation of cells of the T cell lineage. A Notch ligand may be human in origin, or may be derived from other species, including mammalian species such as rodent, dog, cat, pig, sheep, cow, goat, and primates. Particular examples of Notch Ligands include the Delta family. The Delta family includes Delta-1 (Genbank Accession No. AF003522, *Homo sapiens*), Delta-3 (Genbank Accession No. AF084576, *Rattus norvegicus*), Delta-like 1 (Genbank Accession No. NM_005618 and NP_005609, *Homo sapiens*; Genbank Accession No. X80903, I48324, *M. musculus*), Delta-like 3 (Genbank Accession No. NM_053666, N_446118, *Rattus norvegicus*), Delta-4 (Genbank Accession No. AF273454, BAB18580, *Mus musculus*; Genbank Accession No. AF279305, AAF81912, *Homo sapiens*), and Delta-like 4 (Genbank Accession. No. Q9NR61, AAF76427, AF253468, NM_019074, *Homo sapiens*; Genbank Accession No. NM_019454, *Mus musculus*). Notch ligands are commercially available or can be produced by recombinant DNA techniques and purified to various degrees.

2. NK Cell Differentiation

The method further includes the step of maintaining the HPC MeCP2-KO cells in the culture described above for a duration of time sufficient to produce differentiated NK cells. In some embodiments, differentiated NK cells emerge in the cultures along with T cells, however the NK cells may cease to proliferate after week 6. In general, the determination of an increase in the number of NK cells and/or their state of differentiation is assessed using conventional methods known to those of ordinary skill in the art. For example, the cultured cells may be monitored by flow cytometry for the development of NK cells by staining the cells with anti-CD56 and anti-CD3 antibodies. Cells which are $CD56^+$/$CD3^-$ would be indicative of differentiated NK cells.

D. Production of DE Cells and EPCs

Certain embodiments of the present disclosure provide methods for the production of DE cells or EPCs derived from induced pluripotent stem cells maintained under feeder-free conditions. The DE cells and EPCs derived by this method are capable of generating mono-hormonal β cells and hepatocytes. A schematic representation of one exemplary process is provided in FIG. 21. The stages of the pancreatic differentiation process are provided in FIG. 23C. In particular aspects, the differentiation is performed under hypoxic conditions.

Definitive endoderm (DE) is a transient state that quickly differentiates, cannot be proliferated, does not have a distinct morphology, and may not be fully committed to an endoderm fate. On the other hand, EPCs are not transient, have a distinct morphology, and may be cultured indefinitely (Cheng et al., 2012). Endoderm progenitor cells are also characterized as expressing CXCR4, CD117, FOXA1, FOXA2, EOMES, CD34, and SOX17. Endoderm progenitor cells can generate cells in the endoderm lineage, such as liver, pancreas, and intestine, but cannot generate mesoderm or ectoderm either in vitro or in vivo. Likewise, EP cells do not form teratomas in immune-deficient mice. Therefore, DE and EP cells may represent distinct developmental intermediaries and may have different development potentials The method further includes the step of maintaining the DE cell or EPC derived from MeCP2WT and MeCP2KO cells in the culture described above for a duration of time sufficient to produce differentiated glucose responsive beta cells. DE cells or EPCs generated in suspension culture are placed in differentiation medium for the generation of pancreatic cell types. For pancreatic differentiation of EP cells, a protocol described by Nostro et al. (2011) further modified by Cheng et al. (2012) may be utilized. The entire process may be continued as a 3D culture under hypoxic conditions.

In an exemplary method, EPC cultures are expanded for 15 days and cultured in SFD media containing Wnt3A (3 ng/ml), FGF-10 (50 ng/ml) and Dorsomorphin (0.75 µM) for three days to generate foregut/midgut endoderm cells. The cells are cultured in high glucose DMEM media containing GlutaMAX (1%), B27 without retinoic acid (1%), ascorbic acid (50 µg/ml), Pen/Strep (1%), KAAD-Cyclopamine (0.25 µM), trans-Retinoic acid (2 µM), Noggin (50 ng/ml), and FGF-10 (50 ng/ml) for three days to generate pancreatic endoderm cells. Following this step the cells are cultured in high glucose DMEM media containing GlutaMAX (1%), B27 without retinoic acid (1%), ascorbic acid (50 g/ml), Pen/Strep (1%), SB431542 (6 M), and Noggin (50 ng/ml) for three days. Next, the cells are cultured in the previous high glucose DMEM medium supplemented with a Secretase inhibitor (DAPT at 2 µM) for one to two days. From this stage the cells are cultured in SFD media containing glucose (40 mM), nicotinamide (10 mM), SB431542 (6 µM), and Noggin (50 ng/ml) for one to two days. Finally, the cells are cultured in SFD medium containing SB431542 (5.4 µM), Noggin (50 ng/ml), insulin (800 pM), and nicotinamide (10 mM) that is alternated every day between such medium with additional glucose added (40 mM) and no additional glucose added for the next 10 days. Nicotinamide may be added at a concentration of about 0.1 mM to about 15 mM, such as about 10 mM. The presence of mono hormonal beta cells is detected between days 10-15 of differentiation in a 2D format.

Beta cell cultures are harvested on day 21-25 of differentiation, fixed, and stained for quantitation of PDX1/NeuroD1/C-Peptide/Glucagon/Somatostatin by intracellular flow cytometry. The end-stage cultures reveal the presence of mono-hormonal cells. The end-stage cultures are positive for PDX1, NeuroD1 and some levels of NKX6.1. The end-stage aggregates reveal responsiveness to glucose.

In another aspect, the definitive endoderm cells (DE) are differentiated to hepatocytes by methods known in the art. In one method, the hepatocytes may be differentiated from DE cells as depicted in FIG. 40. For example, the entire differentiation process is performed under hypoxic conditions until Day 25 of the differentiation process. Briefly, the DEs are cultured in 2D for about 6 days in SFD media supplemented with BMP4 (50 ng/mL), bFGF (10 ng/mL), EGF (10 ng/mL), VEGF (10 ng/mL), HGF (100 ng/mL), Dex (0.1 μM), DMSO (1%), and FGF-10 (60 ng/mL). The cells are then replated on collagen for about 6 days in SFD medium supplemented with bFGF (10 ng/mL), EGF (20 ng/mL), VEGF (10 ng/mL), HGF (100 ng/mL), OSM (20 ng/mL), Dex (0.2 μM), DMSO (1%), DAPT (2 μM), and Vitamin K (6 μg/mL). For the $3^{rd}$ stage, the cells are plated in 2D in William's E medium supplemented with B27 (1×), EGF (20 ng/mL), OSM (20 ng/mL), Dex (0.1 μM), GlutaMAX (1%), and Pen/Strep (1%) to produce hepatocytes.

E. Cell Culture

In certain embodiments, substantially hypoxic conditions may be used to promote differentiation of PSCs to HPCs, HPCs to erythroid, myeloid or lymphoid lineages, or DE cells or EPCs to endoderm lineages. In certain embodiments, an atmospheric oxygen content of less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, about 5%, about 4%, about 3%, about 2%, or about 1% may be used to promote differentiation. In certain embodiments, the hypoxic atmosphere comprises about 5% oxygen gas.

As described herein, one or more defined culture medium may be advantageously used to promote the differentiation of the present cells; in particular, the elimination of animal products such as serum and mouse feeder layers can reduce the risks associated with exposure of cells to animal products and allow for the generation of cells that could be more safely administered to a human subject. As traditional stem cell culture development has relied on serum products and mouse feeder layers for differentiating stem cells into a variety of cell types, these traditional procedures have limited the scale on which differentiation can be conducted, increased biological variability and potential contamination, and severely hampered the use of ES cells in translational therapies in which they might otherwise prove useful.

Generally, cells of the present disclosure are cultured in a culture medium, which is a nutrient-rich buffered solution capable of sustaining cell growth. Culture media suitable for isolating, expanding and differentiating the present cells according to the method described herein include but not limited to high glucose Dulbecco's Modified Eagle's Medium (DMEM), DMEM/F-15, RPMI 1640, Iscove's modified Dulbecco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human ExCyte lipoprotein, transferrin, insulin, vitamins, essential and non-essential amino acids, sodium pyruvate, glutamine and a mitogen is also suitable. As used herein, a mitogen refers to an agent that stimulates division of a cell. An agent can be a chemical, usually some form of a protein that encourages a cell to commence cell division, triggering mitosis. In one embodiment, serum free media such as those described in U.S. Ser. No. 08/464,599 and WO 96/39487, and the "complete media" as described in U.S. Pat. No. 5,486,359 are contemplated for use with methods described herein. In some embodiments, the culture medium is supplemented with 10% Fetal Bovine Serum (FBS), human autologous serum, human AB serum, or platelet rich plasma supplemented with heparin (2 U/ml).

Myeloid, erythroid, and lymphoid cells can be generated by culturing pluripotent stem cells or hematopoietic precursor cells in a medium under conditions that increase the intracellular level of factors sufficient to promote differentiation of the cells into erythroid, myeloid or lymphoid lineages. The medium may also contain one or more hematopoietic cell differentiation and maturation agents, like various kinds of growth factors. These agents may either help induce cells to commit to a more mature phenotype—or preferentially promote survival of the mature cells—or have a combination of both of these effects. Differentiation and maturation agents may include soluble growth factors (peptide hormones, cytokines, ligand-receptor complexes, and other compounds) that are capable of promoting the growth of cells of the hematopoietic cell lineage. Non-limiting examples of such agents include but are not limited to hematopoietic or endothelial growth factors such as fibroblast growth factor (FGF), vascular endothelial growth factor (VEGF), stem cell factor (SCF), thrombopoietin (TPO), FLT-3 ligand (FLT3L), interleukin-3 (IL-3), interleukin-6 (IL-6), interleukin-9 (IL-9), or granulocyte colony-stimulating factor (G-CSF), or isoforms or variants thereof.

V. USES OF MATURE LINEAGE CELLS

The mature lineage cells (e.g., erythroid, myeloid, lymphoid, and endoderm) provided by methods and compositions of the present disclosure can be used in a variety of applications. These include but are not limited to transplantation or implantation of the cells in vivo; screening cytotoxic compounds, carcinogens, mutagens growth/regulatory factors, pharmaceutical compounds, etc., in vitro; elucidating the mechanism of hematological diseases and injuries; studying the mechanism by which drugs and/or growth factors operate; diagnosing and monitoring cancer in a patient; gene therapy; and the production of biologically active products, to name but a few.

A. Test Compound Screening

Erythroid, myeloid, lymphoid, and endodermal lineages provided herein can be used to screen for factors (such as solvents, small molecule drugs, peptides, and polynucleotides) or environmental conditions (such as culture conditions or manipulation) that affect the characteristics of erythroid, myeloid and lymphoid cells provided herein.

Particular screening applications of this disclosure relate to the testing of pharmaceutical compounds in drug research. The reader is referred generally to the standard textbook *In vitro Methods in Pharmaceutical Research*, Academic Press, 1997. In certain aspects, erythroid, myeloid, lymphoid, and endoderm cells play the role of test cells for standard drug screening and toxicity assays, as have been previously performed on hematopoietic cells and precursors in short-term culture. Assessment of the activity of candidate pharmaceutical compounds generally involves combining the hematopoietic cells or precursors provided in certain aspects of this disclosure with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on hematopoietic cells or precursors, or because a compound designed to have effects elsewhere may have unintended effects on hematopoietic cells or precursors. Two or more drugs can be tested in combination (by combining with the cells either simultaneously or sequentially), to detect possible drug-drug interaction effects.

B. Hematopoietic Cell Therapy

Embodiments also provide for the use of erythroid, myeloid, lymphoid, and endoderm cells provided herein to restore a degree of function to a subject needing such therapy, perhaps due to a hematological disease or disorder or an injury. For example, erythroid, myeloid, lymphoid, and endoderm cells derived by methods disclosed herein may be used to treat hematological diseases and disorders such as hemoglobinopathies, anemias, etc. In addition, erythroid and myeloid lineage cells may be useful in supplying blood or blood cells (such as, for example, red blood cells, platelets, and neutrophil granulocytes) to subjects in need thereof (such as, for example, subjects in need of a blood transfusion or subjects having a hematological disorder). Such cells may be useful for the treatment of hematopoietic cell deficiencies caused by cell-suppressive therapies, such as chemotherapy.

To determine the suitability of cells provided herein for therapeutic applications, the cells can first be tested in a suitable animal model. At one level, cells are assessed for their ability to survive and maintain their phenotype in vivo. Cells provided herein are administered to immunodeficient animals (such as NOD mice, or animals rendered immunodeficient chemically or by irradiation) at a site amenable for further observation, such as under the kidney capsule, into the spleen, into a liver lobule, or into the bone marrow. Tissues are harvested after a period of a few days to several weeks or more, and assessed as to whether starting cell types such as erythrocytes are still present. This can be performed by providing the administered cells with a detectable label (such as green fluorescent protein, or β-galactosidase); or by measuring a constitutive marker specific for the administered human cells. Where cells provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided elsewhere in this disclosure.

Erythroid, myeloid, lymphoid, and endodermal lineages provided by methods of the present disclosure may be tested in various animal models for their ability to treat hematological disorders and injuries. For example, a sickle cell anemia mouse model or the TB cell-deficient Rag-2 knockout mouse may be particularly useful animal models for testing the erythroid, myeloid and lymphoid cells disclosed herein.

Erythroid, myeloid, lymphoid, and endodermal lineages provided in certain aspects of this disclosure that demonstrate desirable functional characteristics or efficacy in animal models, may also be suitable for direct administration to human subjects in need thereof. For purposes of hemostasis, the cells can be administered at any site that has adequate access to the circulation. Hematopoietic cells or precursors thereof may also be delivered at a site of injury or disease.

The cells provided in certain aspects of this disclosure can be used for therapy of any subject in need thereof. Human conditions that may be appropriate for such therapy include the various anemias and hemoglobinopathies, as well as diseases characterized by decreased numbers of hematopoietic cells (such as, for example, myelodysplastic syndrome, myelofibrosis, neutropenia, agranulocytosis, Glanzmann's thrombasthenia, thrombocytopenia, and acquired immune deficiency syndrome). For human therapy, the dose is generally between about $10^9$ and $10^{12}$ cells, and typically between about $5 \times 10^9$ and $5 \times 10^{10}$ cells, making adjustments for the body weight of the subject, nature and severity of the affliction, and the replicative capacity of the administered cells. The ultimate responsibility for determining the mode of treatment and the appropriate dose lies with the managing clinician.

In some embodiments, the mature hepatocytes of the present disclosure may be used for drug metabolism and toxicity testing, in the study of viruses that target hepatic tissue, and as therapeutics. The mature hepatocytes preferably exhibit functional hepatic enzyme activity. In one embodiment, the method includes the steps of (a) exposing one or more mature hepatocytes above to the compound, and (b) monitoring the one or more mature hepatocytes for signs of toxicity. In another embodiment, such a method includes the steps of (a) exposing one or more mature hepatocytes, wherein the compound is metabolized by the hepatocytes; (b) contacting the resulting metabolite(s) of the compound with one or more non-hepatocyte cells; and (c) monitoring the non-hepatocyte cells for any metabolite-induced changes. A method for studying the metabolism of a compound may include the steps of (a) exposing one or more mature hepatocytes; and (b) determining what metabolites are produced by the hepatic processing of the compound. A method of treating a liver disorder may comprise the step of administering one or more mature hepatocytes to a patient having a liver disorder. Non-limiting examples of liver disorders that could be treated using this method include acute liver damage or a metabolic liver disease, such as alpha 1 antitrypsin deficiency or Wilson's disease.

The present disclosure also provides methods for using mature beta cells generated using the methods disclosed herein in cell therapy methods, for example, in the treatment of conditions in which a reduction in beta cell number or beta cell function is causative or contributory.

In some embodiments, the mature microglia, such as with M1 or M2 polarization, provided herein may be used for screening of treatments for neurological diseases, such as Alzheimer's, as well as their treatment.

In some embodiments, the mature macrophages, such as with M1 or M2 polarization, of the present disclosure may be used for screening and therapies. M1 and M2 have distinct expression profiles of chemokines. The term "polarization" is used herein to designate the phenotypic features and the functional features of the macrophages. The phenotype can be defined through the surface markers expressed by the macrophages. M1 macrophages express CXCL9 and CXCL10 chemokines which are known for attracting Th1, while M2 macrophages express CCL17, CCL22 and CCL24. Chemokines such as CCL2 and CXCL4 can also polarize macrophages to an M2-like phenotype.

Additionally, the mature lymphoid cells, such as T cells, NK cells, NK/T cells, and B cells, may be used for various screening and therapeutic applications. In some aspects, the lymphoid lineages may be used for in vitro screening of compounds for therapies. The lymphoid lineages may also be used as adoptive cell therapy, such as for the treatment of cancer.

C. Distribution for Commercial, Therapeutic, and Research Purposes

For purposes of manufacture, distribution, and use, the erythroid, myeloid, lymphoid, and endoderm cells of the present disclosure are typically supplied in the form of a cell culture or suspension in an isotonic excipient or culture medium, optionally frozen to facilitate transportation or storage.

This disclosure also includes different reagent systems, comprising a set or combination of cells that exist at any time during manufacture, distribution, or use. The cell sets comprise any combination of two or more cell populations described in this disclosure, exemplified but not limited to programming-derived cells (hematopoietic lineage cells, their precursors and subtypes), in combination with undifferentiated stem cells, somatic cell-derived hematopoietic cells, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Generation of MeCP2 Knockout Cell Line

To determine the role of MeCP2 in the hematopoietic differentiation process, a MeCP2 knockout iPSC cell lines were generated. The male wildtype (WT) 01279 iPSC line was engineered to knockout MeCP2 to create the MyCell® 01279.107.3902 cell line. Using TAL nuclease, a series of stop codons were inserted prior to the methyl CpG binding domain (FIG. 1B) of MeCP2 by transfection of MeCP2 TALENs and the donor plasmid containing the stop codon insertion was followed by insertion of LoxP flanked, PGKp-Puromycin-SV40 pA in the reverse orientation. The 01279 iPSCs were transfected with MeCP2 TALENS and Donor plasmid p1553 expressing wild-type EBNA1. Additional iPSC lines including iPSC 9025, SONL (i.e., iPSCs episomally reprogrammed using the Sox-2, Oct-4, Nanog, and Lin28 reprogramming factors), TIPS1e (i.e., iPSCs differentiated from T cells), HLA-H, Line A, and HLA-G were also transfected with MeCP2 TALENS and the donor plasmid.

The cells positive for insertion were selected for with puromycin selection, and colonies were then picked and screened by integration PCR. Initial screening was performed on all picked colonies for right-arm, left-arm, and backbone. All colonies were rescreened around passage 3 to confirm the MeCPR2 knockout status by PCR. The clones were transitioned to E8 medium and hypoxic conditions after confirmation of PCR. Of the colonies selected for screening, about 6-50% were found to be correctly engineered.

TABLE 1

Summary of Screening Post-Transfection

| Number colonies picked | Number of Colonies Passed Screening | Percentage Correctly Engineered |
|---|---|---|
| 37 | 4 | 10.81% |
| 7 | 2 | 28.57% |
| 5 | 1 | 20.00% |
| 4 | 2 | 50.00% |
| 20 | 4 | 20.00% |
| 33 | 2 | 6.06% |

TABLE 2

Summary of Engineered MeCP2KO iPSC Clones

| Cell Line | Sex | Reprogramming Method | Reprogramming Factors | Cell source for reprogramming | MECP2 Status |
|---|---|---|---|---|---|
| 9025 | Male | Episosmal | 7 | Progenitor cells blood | Wild Type Exon 3/Exon 4 |
| 9025 1553-18-1 P47(3) | Male | Episosmal | 7 | Progenitor cells blood | MeCP2KO Exon 3 |
| 9025 1553-18-4 P47(3) | Male | Episosmal | 7 | Progenitor cells blood | MeCP2KO Exon 3 |
| 9025 1553-18-15 P48(4) | Male | Episosmal | 7 | Progenitor cells blood | MeCP2KO Exon 3 |
| SONL | Male | Viral | 4 | Progenitor cells blood | Wild Type Exon 3/Exon 4 |
| SONL 1553-7-4 P29(4) | Male | Viral | 4 | Progenitor cells blood | MeCP2KO Exon 3 |
| SONL 1553-8-3 P 29(4) | Male | Viral | 4 | Progenitor cells blood | MeCP2KO Exon 3 |
| Tips1e | Male | Viral | 4 | T cells | Wild Type Exon 3/Exon 4 |
| Tips1E 1553-9-1 P27(4) | Male | Viral | 4 | T cells | MeCP2KO Exon 3 |
| HLA-H | Male | Episosmal | 6 | Progenitor cells blood | Wild Type Exon 3/Exon 4 |
| Line-H 1553-19-1 P20(4 | Male | Episosmal | 6 | Progenitor cells blood | MeCP2KO Exon 3 |
| Line-H 1553-19-2 P20(4) | Male | Episosmal | 6 | Progenitor cells blood | MeCP2KO Exon 3 |
| Line A | Male | Episosmal | 6 | Progenitor cells blood | Wild Type Exon 3/Exon 4 |
| Line A 1553-13-2-A1 P33(11) | Male | Episosmal | 6 | Progenitor cells blood | MeCP2KO Exon 3 |
| Line A 1553-13-2-A1B2 P33(11) | Male | Episosmal | 6 | Progenitor cells blood | MeCP2KO Exon 3 |

TABLE 2-continued

Summary of Engineered MeCP2KO iPSC Clones

| Cell Line | Sex | Reprogramming Method | Reprogramming Factors | Cell source for reprogramming | MECP2 Status |
|---|---|---|---|---|---|
| Line A 1553-13-2-A1B2 P33(11) | Male | Episosmal | 6 | Progenitor cells blood | MeCP2KO Exon 3 |
| Line A 1553-14-10-B3 P33(11) | Male | Episosmal | 6 | Progenitor cells blood | MeCP2KO Exon 3 |
| Line-G | Male | Episosmal | 6 | Progenitor cells blood | Wild Type Exon 3/Exon 4 |
| Line G 1553-15-17 P21(6 | Male | Episosmal | 6 | Progenitor cells blood | MeCP2KO Exon 3 |
| Line G 1553-15-20 P21(6) | Male | Episosmal | 6 | Progenitor cells blood | MeCP2KO Exon 3 |

Of the screened colonies for the 01279 iPSC line, 96% were positive for insertion by two PCR screening reactions. Fourteen of the clones were expanded and screened at passage 3, and eight of the clones were found to be negative for the integration of the backbone plasmid. Thus, three of the remaining clones were sequenced through the insert and two were found to be polyclonal. The one monoclonal line 01279.107.3902 was selected and fully characterized for further studies. Additional clones were also obtained and characterized as correctly engineered. The amino acid alignment of MeCP2 variants 001, 002, 005 and 008 is depicted in FIG. 1C. The variant 008 does not code for a Methyl CpG binding domain.

Example 2—3D Protocol for Production of HPCs

The 01279.107.3902 MeCP2 knockout (MeCP2KO) cells of Example 1 and WT 01279 cells were subjected to the 3D differentiation protocol for the production of HPCs (FIG. 1A). First, the iPSCs were acclimatized to hypoxic conditions for 5-10 passages under feeder-free conditions on Matrigel™- or Vitronectin-coated in Essential 8 (E8) media. Aggregates were made from sub confluent iPSCs at a density of 0.25-0.5 million cells per ml in the presence Serum Free Defined (SFD) media supplemented with 5 uM blebbistatin. The process was performed in ultra-low attachment (ULA) plates or spinner flasks in SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, GlutaMAX, Pen/Strep and $4.5 \times 10^{-4}$ M monothioglycerol.

Once the embryoid bodies (EBs) had formed, differentiation was initiated by supplementing the SFD basal media with 50 ng/ml of BMP-4, VEGF, and bFGF for the first 4 days. On the fifth day, the EB cultures were placed in the presence of Flt-3 Ligand, IL3, IL6, SCF, and TPO each at 50 ng/ml and heparin at 5 U/ml. The EB cultures were supplemented with half the volume of fresh differentiation media containing cytokines every 2 days during the differentiation process until day 12-16 of differentiation under hypoxic conditions. The cells were harvested after the differentiation process and the phenotype was assessed by flow cytometry and the functional capability was assessed using the CFU assay.

For flow cytometry analysis the cells were collected and washed once with media. The cell pellet was digested using TrypLE™ or 0.5% trypsin for 5-10 minutes in a 37° C. incubator followed by washes with media and passaged through a 70-μm cell strainer. The cells were resuspended in PBS-FBS containing FACS buffer, counted to estimate cell viability and stained with fluorochrome-conjugated monoclonal antibodies: anti-human CD43 (1G10), anti-human CD31 (WM-59), anti-human CD41 (HIP8); anti-human CD45 (HI30); anti-human CD34 (581, 8G12) (BD Biosciences San Jose, Calif.); and anti-human CD235. Non-viable cells were excluded with 7-aminoactinomycin D (7-AAD, BD Biosciences) or PI. Live cell analysis was performed on a FACSCalibur™ or Accuri flow cytometer.

For the clonogenic hematopoietic progenitors assay (CFU assay) the EBs were dispersed into single cell suspensions using TrypLE or 0.5% trypsin/EDTA. Viable cells were quantified, plated (50,000-300,000 cells per mL), and assayed in humidified chambers for hematopoietic CFCs in using Human Methylcellulose Complete Media (R&D Systems, Minneapolis, Minn.) containing stem cell factor (SCF) 50 ng/mL, erythropoietin (EPO) 3 U/mL, granulocyte-macrophage colony-stimulating factor (GM-CSF) 10 ng/mL, interleukin-3 (IL-3) 10 ng/mL. After 14 days the colonies were scored according to their morphology and colonies per $10^5$ cells plated were quantified. Serum-containing or Serum-Free MethoCult™ media (Stem Cell Technologies) can be used to generate colonies.

Example 3—Effect of MeCP2 on Erythroid Differentiation

To determine the effect of MeCP2 knockout on erythroid differentiation, a panel of HPCs derived from iPSC were evaluated for their potential to generate mature erythroid cells including the MeCP2 knockout 01279.107.3902 HPCs, WT 01279 HPCs, iCell® HPCs (i.e., 01279 cells produced from forward programming), CD34⁻ derived fraction (i.e., the CD34 negative fraction of 01279 cells), 2D derived 01279 HPCs, and cord blood HPCs (PCT Publication No. WO2012/109208).

Figure 2A:
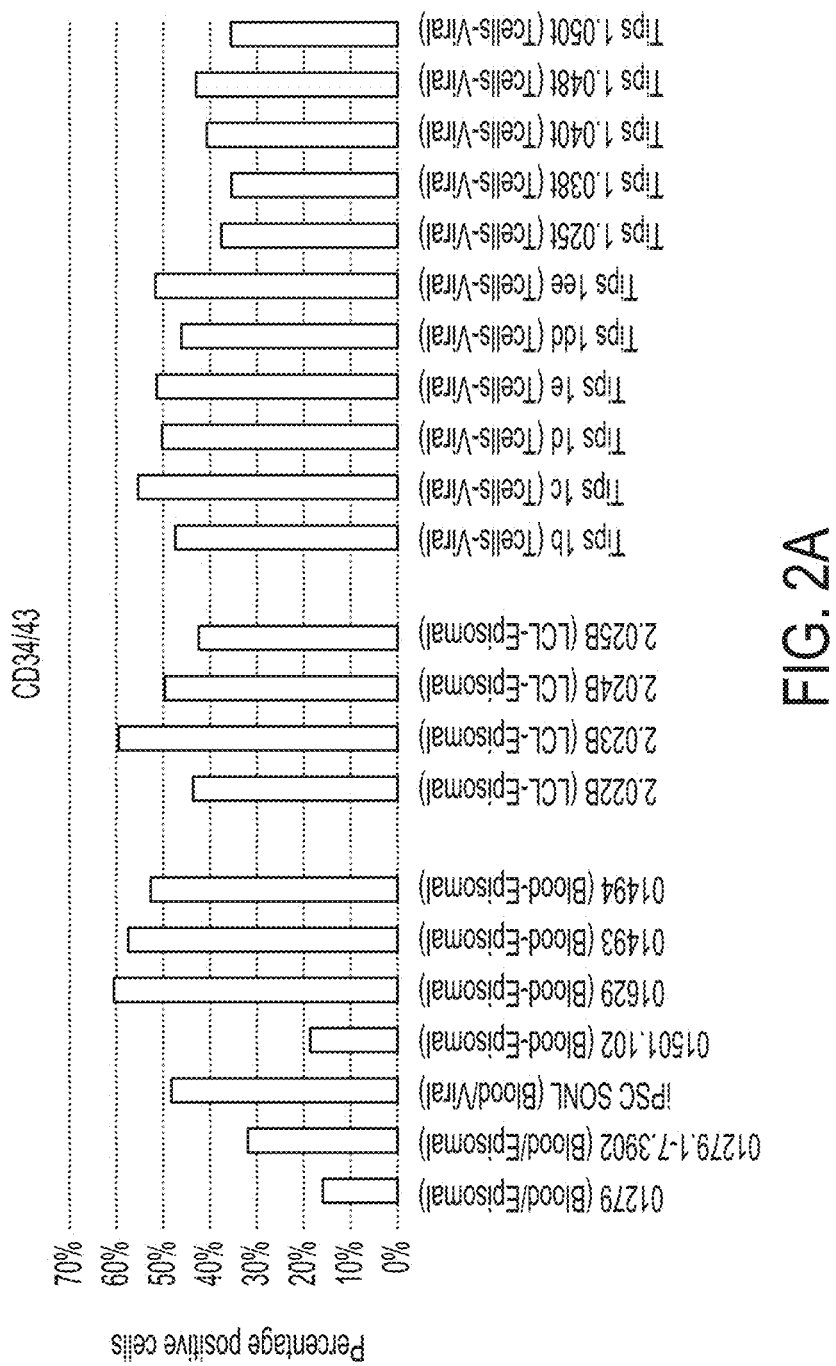
FIGS. 2A-2B: (2A) Summary of HPC differentiation across many iPSC cell lines on day 12 of differentiation. The percentage of HPC ($CD43^+/CD34^+$) double positive cells is quantified by flow cytometry. (2B) The efficiency of HPC generation is calculated by dividing the absolute number of HPCs generated per input number of iPSCs shown in the graph.
Figure 2B:
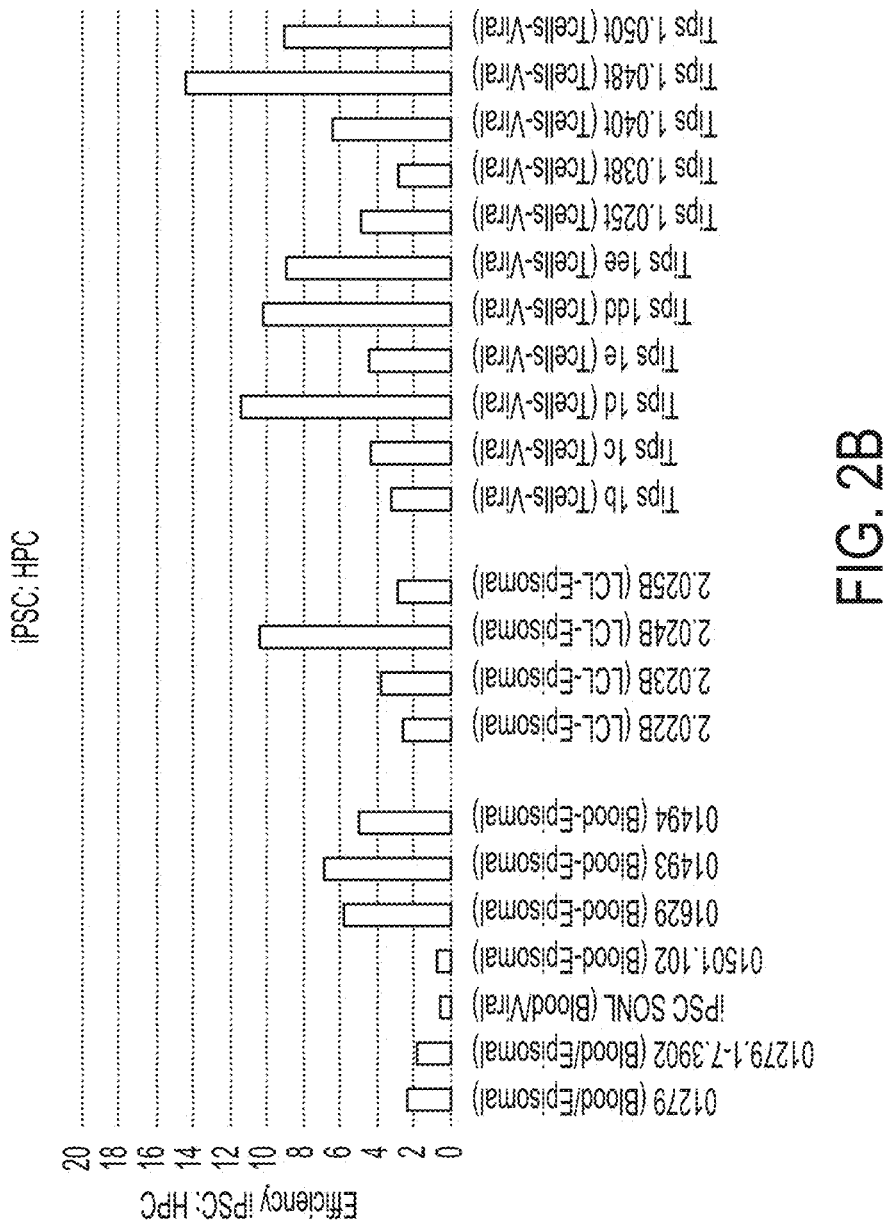

To induce hematopoietic differentiation, iPSCs cells were harvested using EDTA and placed in serum-free EB basal media for 12 hours in low-attachment plates to facilitate aggregate formation. SFD was supplemented with bone morphogenetic factor (BMP-4), vascular endothelial growth factor (VEGF) and zebrafish FGF-2 for the first 4 days followed by incubation with media supplemented with Flt-3 ligand (Flt-3L), interleukin-3 (IL-3), interleukin-6 (IL-6), Thrombopoietin (TPO), heparin, and Stem cell factor (SCF) for the next 8 days. The resulting HPCs were harvested and the percentage of CD43/CD34 cells was quantified by flow cytometry (FIG. 2A). The efficiency of the process was calculated by dividing the absolute number of HPCs generated per input number of iPS cells (FIG. 2B).

Figure 3:
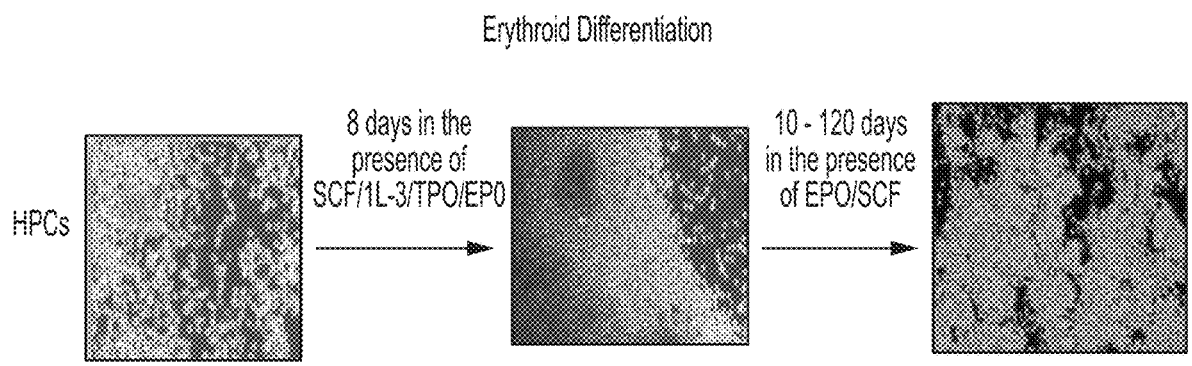
FIG. 3: A schematic overview of erythroid lineage differentiation from iPSC derived HPCs. Day 12 HPCs are differentiated in the presence of SCF, IL3, TPO and EPO for a period of 8 days followed by further culture of cells in the presence of EPO and SCF alone for up to 120 days to generate a pure culture of erythrocytes.

To generate human erythroblasts from HPCs derived from iPSCs the cells were cultured at a density of 0.5-1×10⁶ cells/mL in Primitive Erythroid Expansion Medium (pEEM) for 1-2 weeks (FIG. 3). The pEEM media comprised SFEM medium supplemented with 0.3% Excyte (Serologicals), Holo-Transferrin (1 mg/ml, Sigma), Hydrocortisone (1 mM, Sigma), SCF (50 ng/ml, R&D Systems), EPO (2 U/ml, R&D Systems), IL-3 (5 ng/ml), IL-6 (10 ng/ml) and TPO (50 ng/ml). After 2 weeks, the cells in culture at this stage were observed to have surface expression of CD71, CD235, and CD36. Thus, the cells were differentiating toward the erythroid lineage. The MeCP2KO cells exhibited greater levels of CD235 positive cells than MeCP2WT cells (Table 3).

TABLE 3

Enhanced CD235 expression in iPS cell clones containing MeCP2KO on day 16 of differentiation.

| IPSC Clone | MeCP2 status | CD235 Expression |
| --- | --- | --- |
| 01279.107.03902 | MeCP2KO | 26% |
| 01279 | MeCP2 WT | 7.5% |

In contrast, to differentiate the HPCs towards erythrocyte differentiation, HPCs were cultured in Erythroid Expansion Media (EEM). The EEM media comprised SFEM medium supplemented with 0.3% Excyte (Serologicals), Holo-Transferrin (1 mg/ml, Sigma), Hydrocortisone (1 mM, Sigma), SCF (50 ng/ml, R&D Systems), and EPO (2 U/ml, R&D Systems). The cells remained in this media for the next 1-2 weeks and were fed every other day with a fresh media exchange. The presence of an enriched population of erythroid cells was observed at the end of 2 weeks revealing 80-90% to express CD71, CD235a and CD36.

Figure 4A:
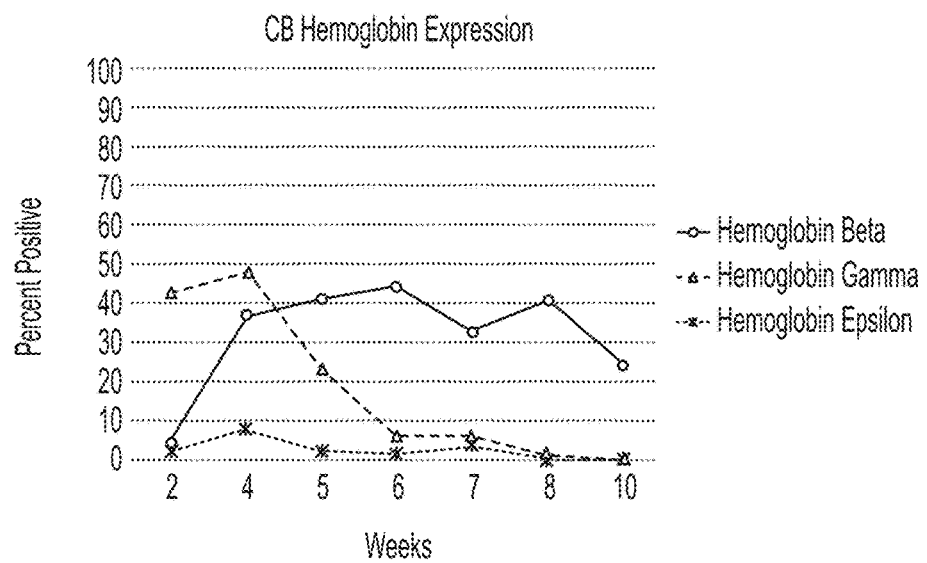
FIGS. 4A-4D: (4A) Time course of emergence of globins during in vitro erythroid differentiation using HPCs from cord blood cells. Schematic representation of the emergence of β-globin expression and the developmental switches, from embryonic to fetal globins during the first trimester of conception, and from fetal to adult around the time of birth as depicted by Orkin et al., 2012. (4B) FACS profile of surface staining of CD235 of cord blood (CB) derived HPCs, iPSC MeCP2WT and MeCP2KO clones between 2-8 weeks of erythroid differentiation. (4C) FACS profile of surface staining of CD71 of CB-derived HPCs, iPSC MeCP2WT and MeCP2KO clones between 2-7 weeks of erythroid differentiation. (4D) FACS profile of surface staining of CD36 of CB-derived HPCs, iPSC MeCP2WT and MeCP2KO clones between 2-8 weeks of erythroid differentiation.
Figure 4B:
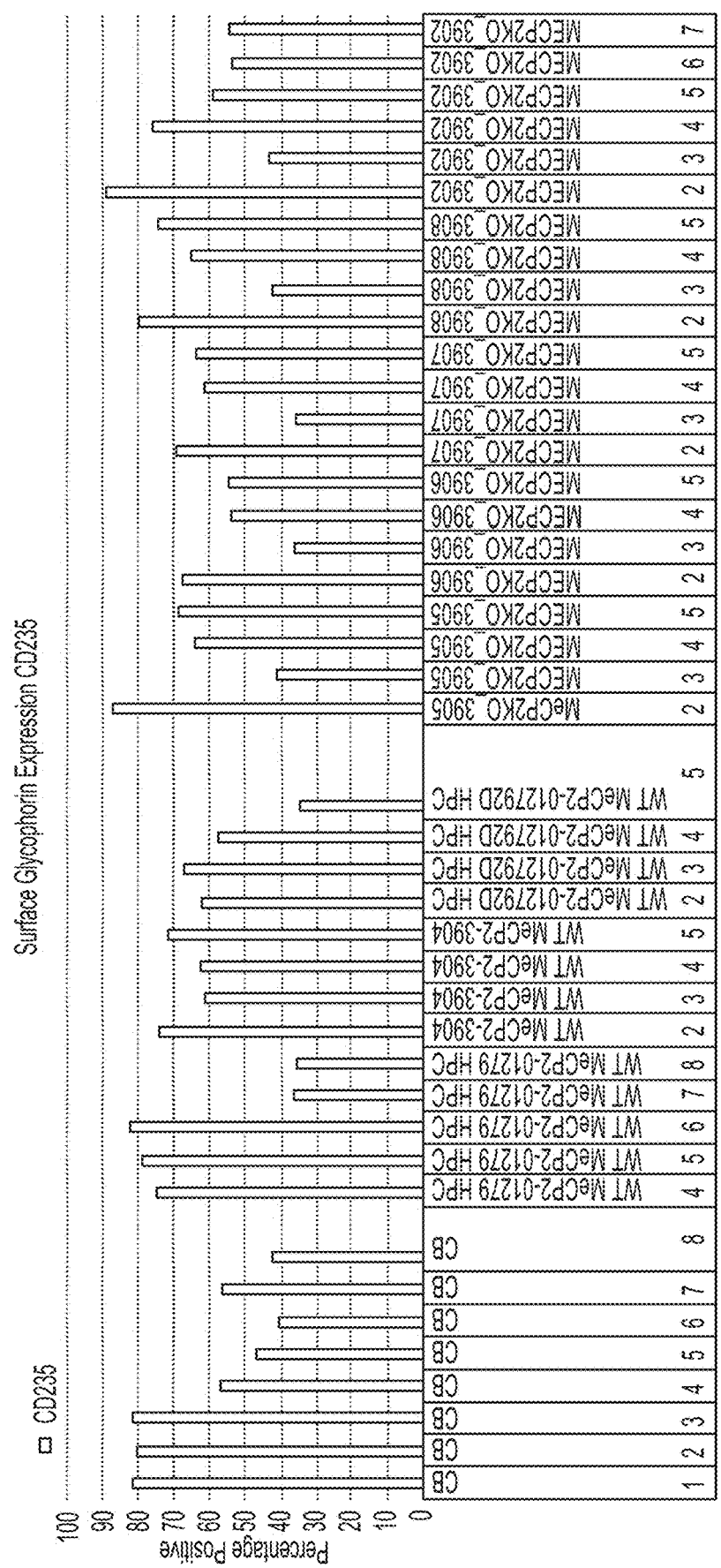
Figure 4C:
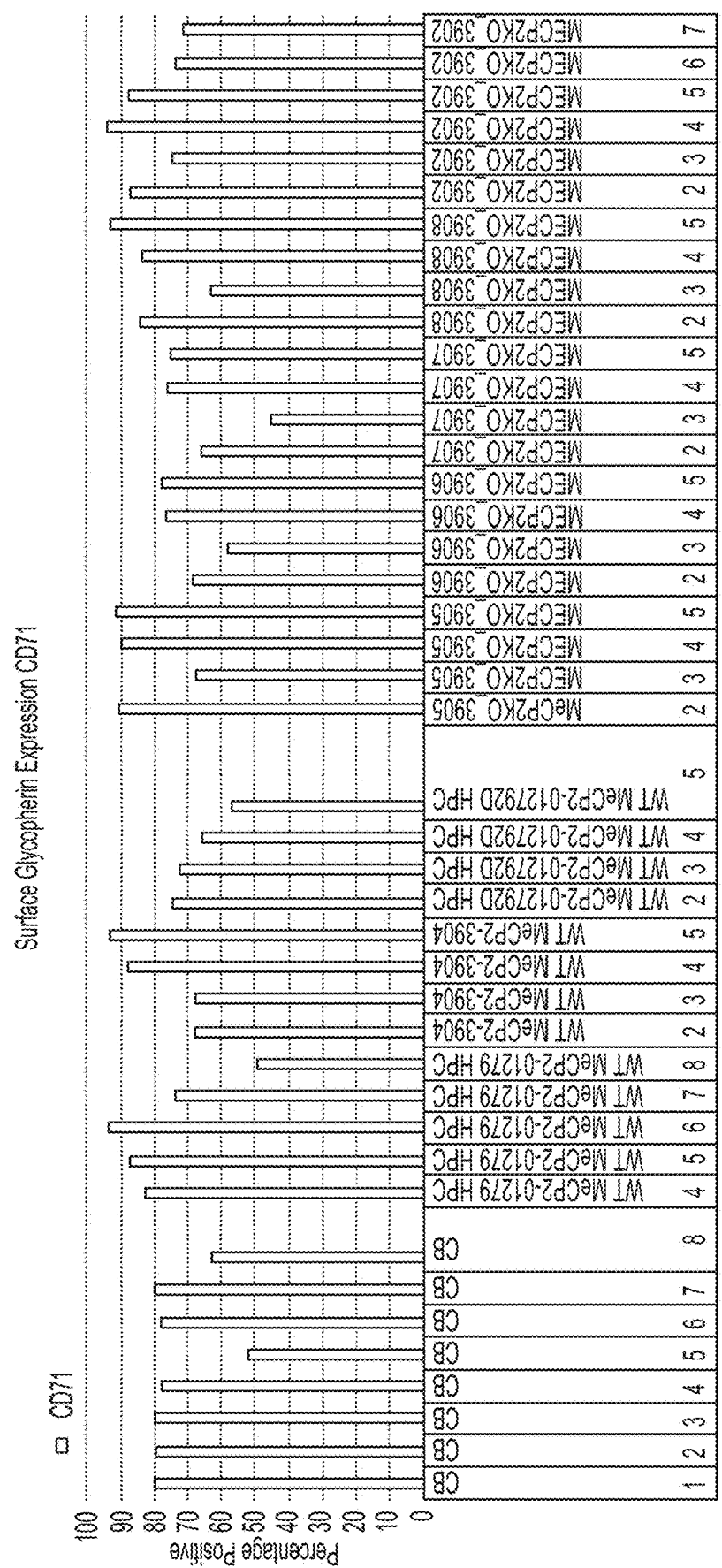
Figure 4D:
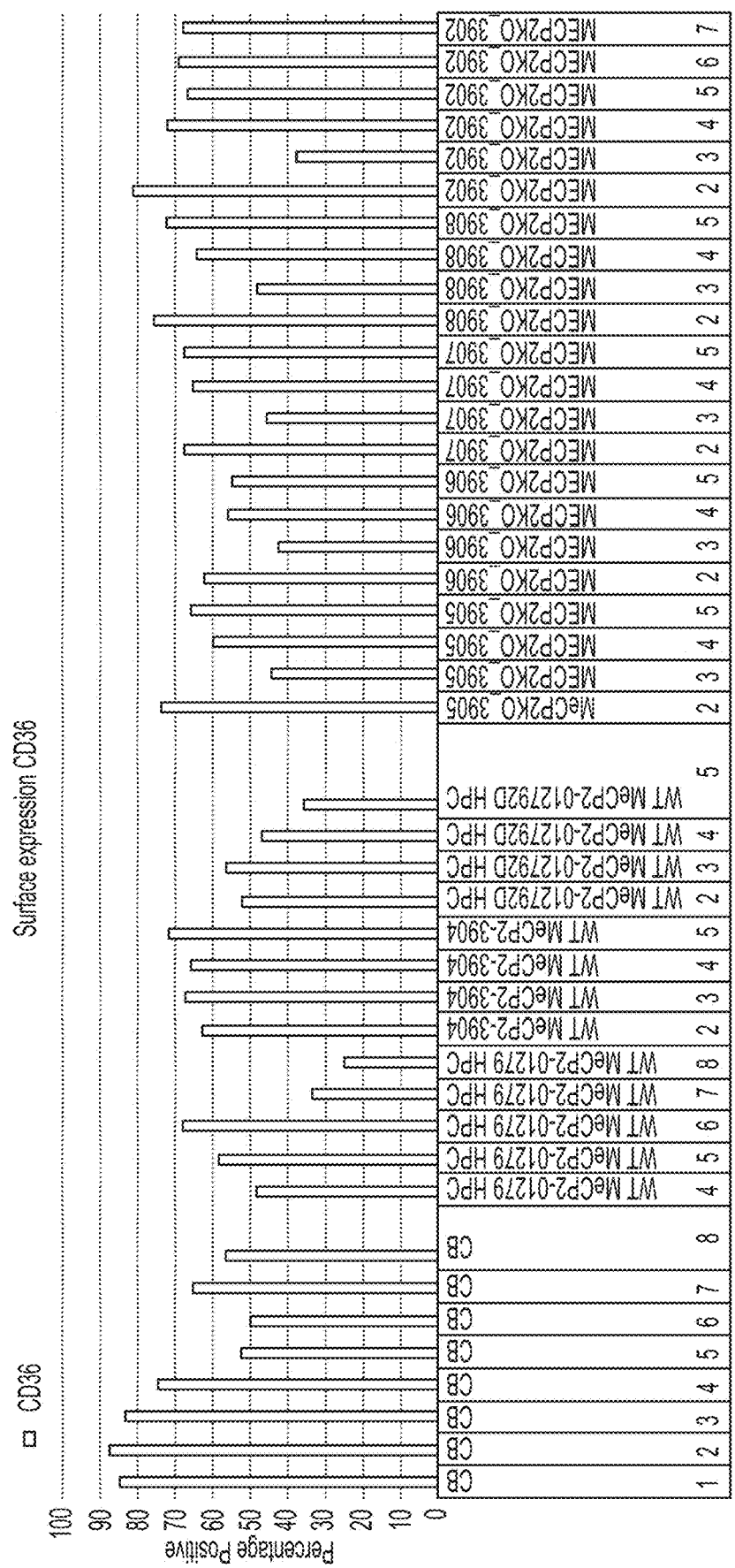

Further analysis of the erythrocyte differentiation exhibited by the various HPC cell lines was performed by measuring the percentage of cells positive for the cell surface markers CD71, CD235a, CD36, CD71/235a, CD235a/36, and CD71/36 at weeks 2-8 of differentiation (FIGS. 4A-4C). It was found that the 01279.107.3902 HPCs had a significantly higher percentage of cells positive for the cell surface markers for erythroblasts. Thus, while all of the cell lines except for the iCell® HPCs were shown to differentiate to erythrocytes for 4 weeks of differentiation, the MeCP2KO enhanced the production of red blood cells.

Next, the cell count for each of the HPC cell lines was measured over 9 weeks of the erythrocyte differentiation process. While most of the cell lines were observed to have decreased cell numbers over the differentiation process, the 01279.107.3902 cells had increased cell counts from week 0 to week 4. In addition, the 01279.107.3902 cells had increased expression of the erythrocyte marker Glycophorin A (CD235a) from week 4 to week 6 as compared to the other cell lines.

Figure 5A:
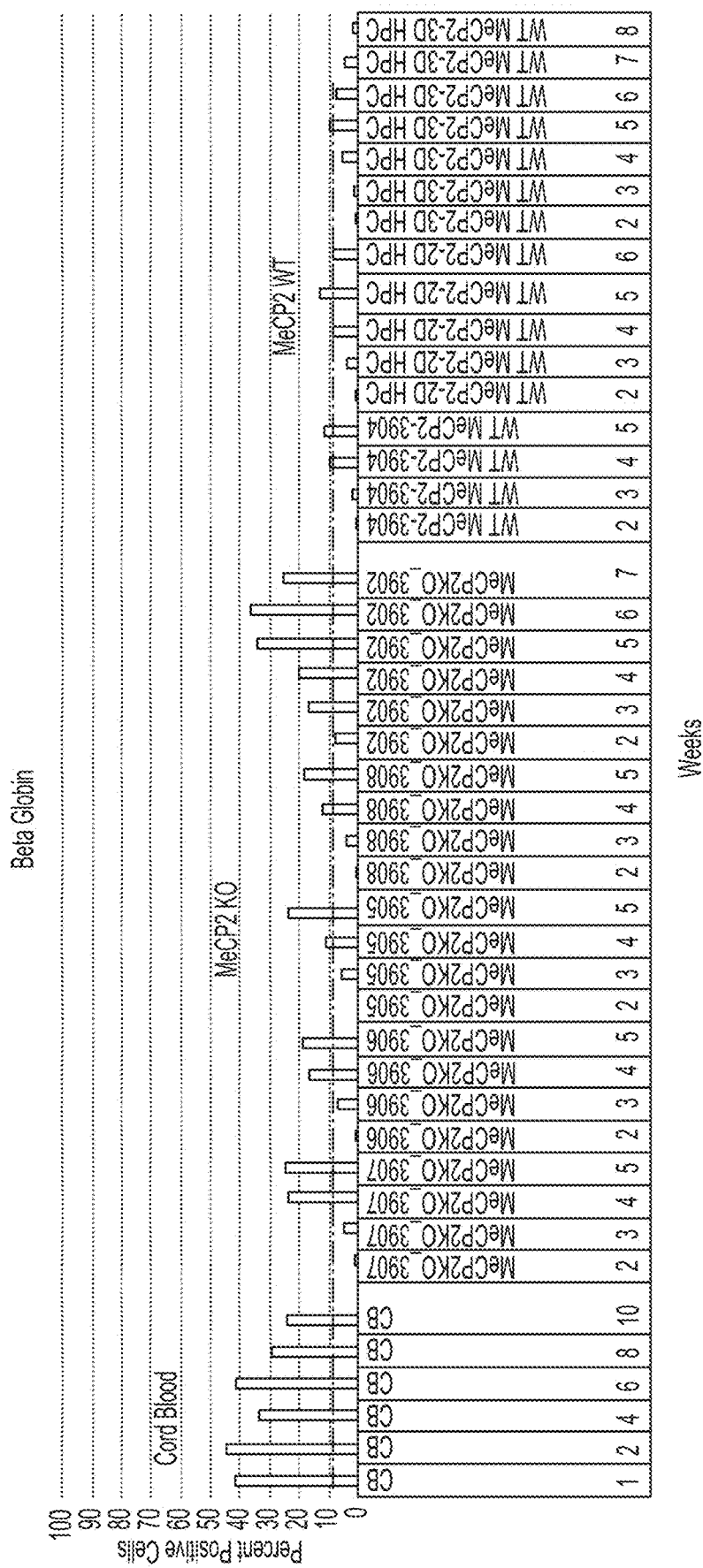
FIGS. 5A-5C: (5A) Comparative analysis of intracellular adult globin expression in erythrocyte cultures derived from CB, iPSC MeCP2WT, and iPSC MeCP2KO clones. (5B) Comparative analysis of intracellular embryonic ε globin expression in erythrocyte cultures derived from CB, iPSC MeCP2WT, and iPSC MeCP2KO clones. (5C) Comparative analysis of intracellular fetal γglobin expression in erythrocyte cultures derived from CB, iPSC MeCP2WT, and iPSC MeCP2KO clones (5C).
Figure 5B:
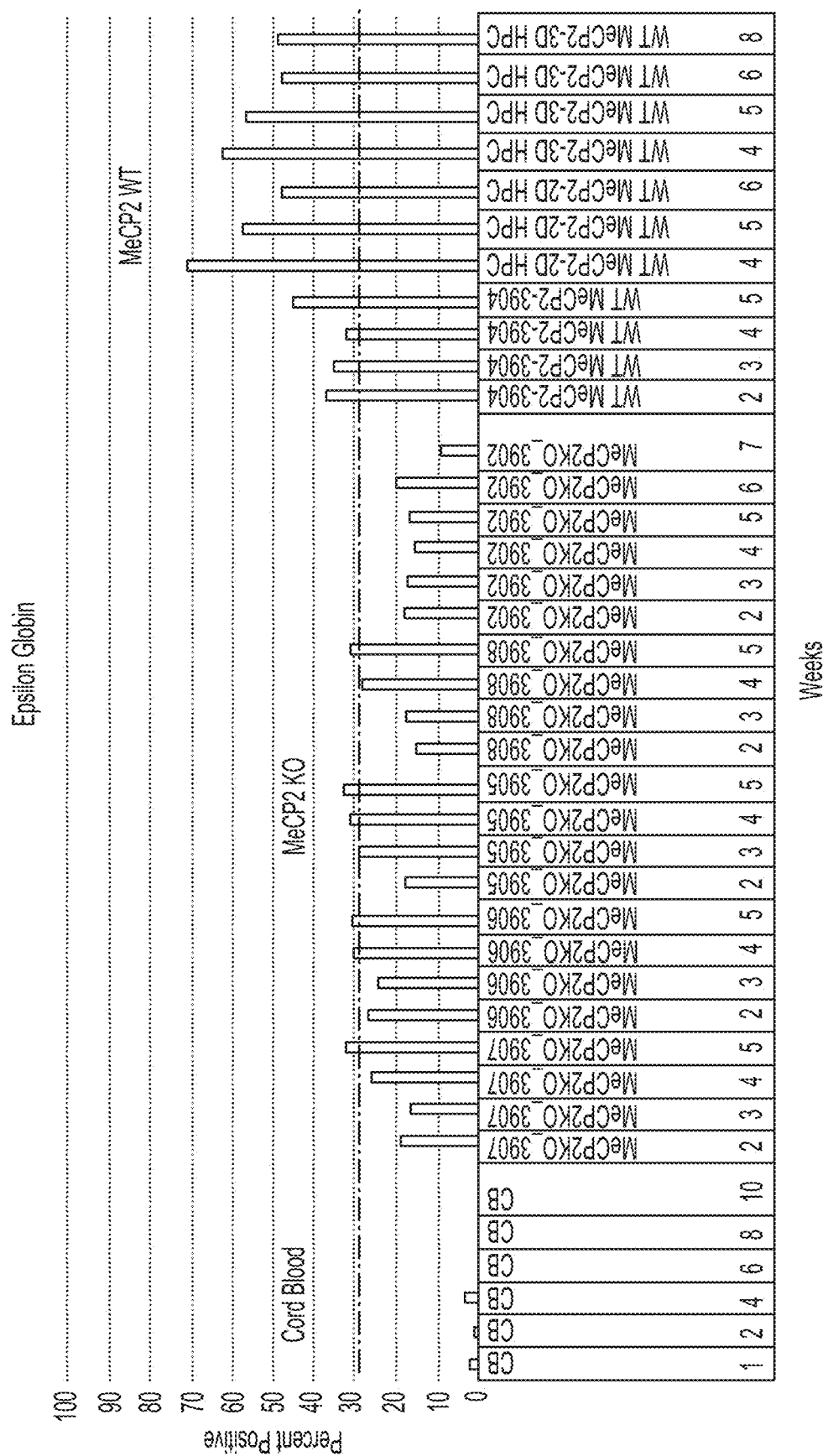
Figure 5C:
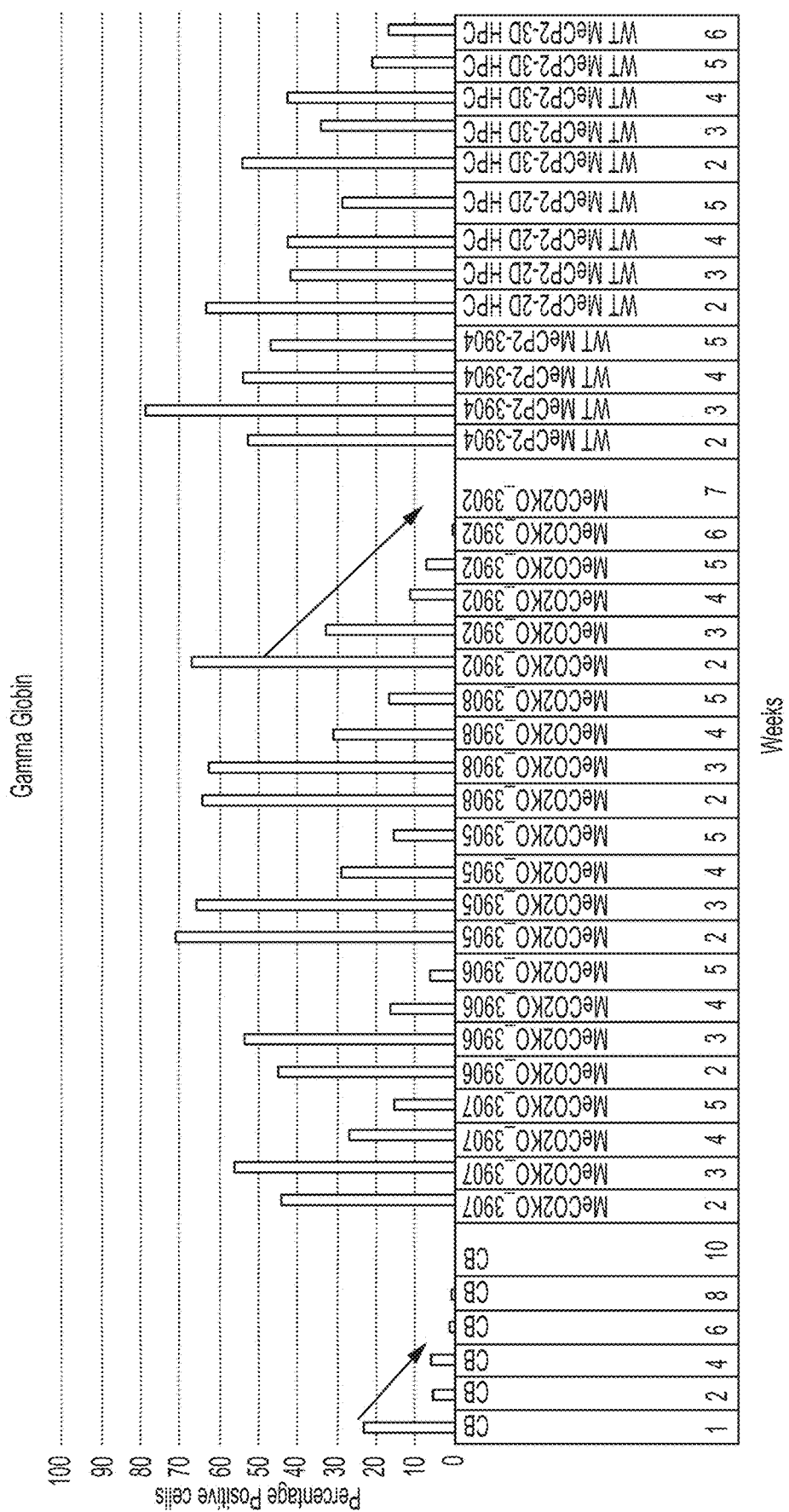
Figure 6:
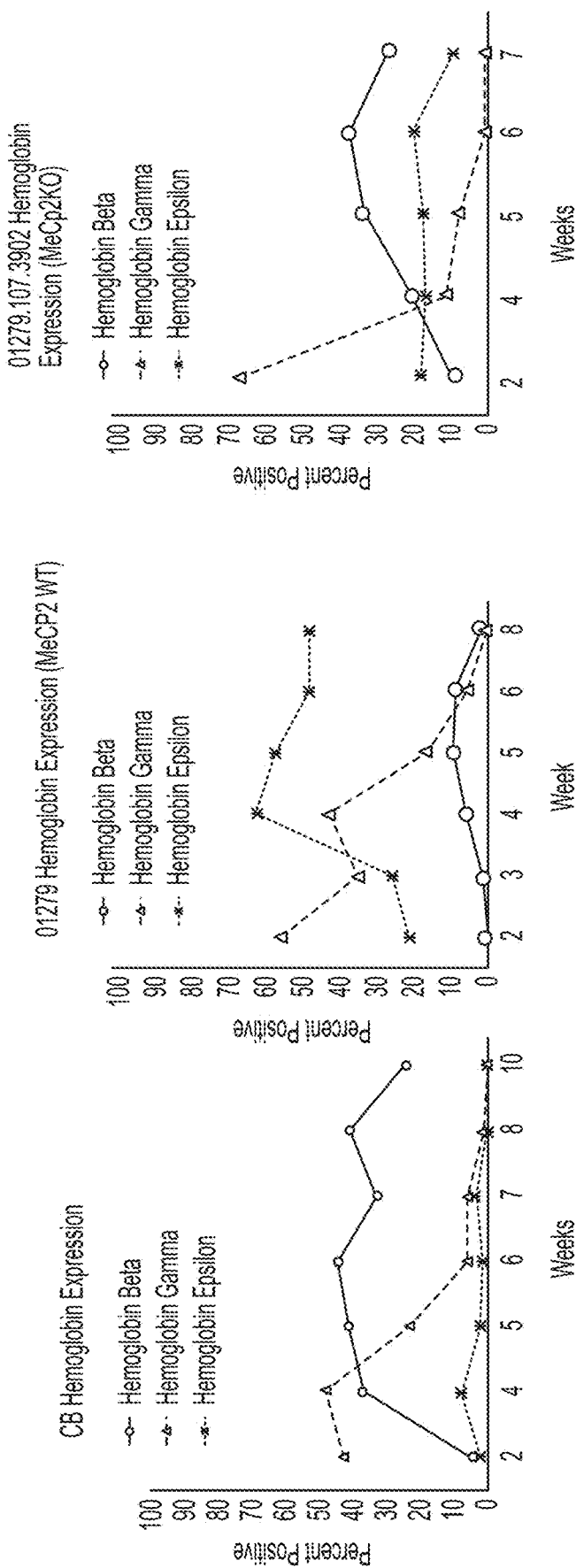
FIG. 6: Quantification and comparative analysis of intracellular globins (β, ε, and γ) during week 2-7 of erythrocyte differentiation derived from CB, iPSC 01279 (MeCP2WT) and iPSC 01279.107.3902 (MeCP2KO).

The cells were then co-stained for CD235a and various globins, including β globin, γ globin and ε globin. It was observed that the 7 and 8 week old cells differentiated from the 01279.107.3902 cell line had a large percentage of cells positive for β globin and a low percentage of cells positive for ε globin (FIG. 5A-5B, 6). Over the erythrocyte differentiation process, the 01279.107.3902 cells had high levels of β globin expression as compared to the 01279 HPCs. On the other hand, the 01279.107.3902 cells had low expression of epsilon expression. In addition, Wright stain of the erythrocytes differentiated from the 01279.107.3902 cell line showed enucleation. Therefore, the 01279.107.3902 cell line differentiated to more mature red blood cells shown as possessing higher levels of β globin versus the WT 01279 HPC cell line. Thus, the MeCP2KO facilitates maturation of erythrocytes derived from iPSCs.

Example 4—Effect of MeCP2 Knockout on Lymphoid Differentiation

To determine the effect of MeCP2 knockout on lymphoid differentiation, the cell lines were subjected to culture conditions for T and NK cell differentiation. First, several variables were tested for T cell differentiation in a stroma dependent protocol. The day 12 HPCs produced from different cell lines were tested for T cell potential on stromal lines, including OP9 bone marrow stromal cells and MS5 murine bone marrow stromal cells. The cells were cultured in αMEM media with 20% FBS, 10 ng/mL SCF, 5 ng/mL Flt-3 and 5 ng/mL IL-7. The cells were refreshed by a half-medium change three times a week. Analysis of the cells for the presence of T cells showed that the cells had a tendency to generate myeloid cells and the presence of $CD3^+$ cells could not be detected. In addition, the stromal co-cultures performed poorly under hypoxic conditions.

Accordingly, a feeder free T cell differentiation protocol was developed. The HPCs were plated on non-treated tissue culture plates coated with Retronectin and Notch DLL4 at 0.5 μg/cm$^2$ at a cell density of about 5,000 to about 25,000 cells/cm$^2$. The HPCs were cultured in StemSpan Serum-Free Expansion Medium (SFEM; StemCell Technologies) media supplemented with 1% Glutamax, 1% Penicillin Streptomycin, 95 μM Ascorbic acid (WAKO labs), as well as 50 ng/mL of IL-7, SCF, Flt-3, and TPO (Peprotech). The media was replenished every 48 hours and at 2 weeks the cells were split non-enzymatically to new ligand coated plates. In addition, between 2 and 3 weeks the cells were analyzed for the presence of pre-T cells by the cell surface markers CD5 and CD7. At 4 weeks, the cells were analyzed for the presence of T cells by the cell surface markers CD3, CD4 and CD8. At 6-8 weeks, the cells were analyzed for the presence of T and NK cells using the cell surface markers CD4, CD8, CD3, CD94 and CD56.

One of the parameters tested for its effect on T cell differentiation was the choice of the matrix coating on the culture plates. A comparison was performed by analyzing the emergence of pre-T cells under serum free conditions using various matrix combinations with Notch DLL4 with cord blood cells at 3 weeks post-plating. The results showed that the combination of retronectin with DLL4 was more effective at differentiating the cord blood cells to pre-T cells than the combination with vitronectin or tenascin (Table 4).

TABLE 4

Choice of matrix for lymphoid differentiation. Cells plated on Retronectin-DLL4 revealed the presence of pre T cells ($CD5^+/CD7^+$) cells.

| Matrix for T cell Differentiation | % CD5 | % CD7 | % CD5/CD7 |
| --- | --- | --- | --- |
| Retronectin-DLL4 | 11% | 40% | 11% |
| Tenascin -DLL4 | 0.7% | 5.2% | 0.7% |
| Vitronectin -DLL4 | 0.6% | 6% | 0.6% |

Surprisingly, it was found that hypoxic conditions enhance feeder-free T cell differentiation. Specifically, it was observed that hypoxia resulted in an increase in the percentage of cells positive for CD8 and a decrease in the percentage of cells positive for CD4 as compared to the cell differentiated under normoxic conditions (Table 5).

TABLE 5

Hypoxia favors T cell differentiation. Cells differentiating under hypoxic conditions revealed the presence of T and NK cells.

| Matrix for T cell Differentiation | CD3 | CD4 | CD8 | CD3/CD4 | CD3/CD4 | CD4/CD8 | CD56+/CD3− (NK cells) |
|---|---|---|---|---|---|---|---|
| Hypoxia | 7% | 11.4% | 49% | 2.6% | 2% | 5.6% | 28% |
| Normoxia | 0.2 |  | 57% | 4.7% | 0 | 0 | 0 | 6% |

TABLE 6

Summary of iPSC cell lines tested for lymphoid differentiation.

| Cell line | Reprogramming Method | Source material for reprogramming | MeCP2 Status | |
|---|---|---|---|---|
| 01279 | Episomal | Progenitor cells Blood | Wild Type Exon 3/Exon 4 | Male |
| 01279.107.3904 | Episomal | Progenitor cell Blood | Wild Type Exon 3/Exon 4 | Male |
| 01279.107.3902 | Episomal | Progenitor cells Blood | MeCP2KO Exon 3 | Male |
| 01279.107.3905 | Episomal | Progenitor cells Blood | MeCP2KO Exon 3 | Male |
| 01279.107.3906 | Episomal | Progenitor cells Blood | MeCP2KO Exon 3 | Male |
| 01279.107.3907 | Episomal | Progenitor cells Blood | MeCP2KO Exon 3 | Male |
| 01279.107.3908 | Episomal | Progenitor cells Blood | MeCP2KO Exon 3 | Male |
| TiPS1E | Viral | T cells | Wild Type Exon 3/Exon 4 | Male |
| 1.025T | Viral | T cells | Wild Type Exon 3/Exon 4 | Female |
| 2.022B | Episomal | LCL | Wild Type Exon 3/Exon 4 | Male |
| 2.0224B | Episomal | LCL | Wild Type Exon 3/Exon 4 | Female |
| 01501.102 | Episomal | Progenitor cells Blood | Wild Type Exon 3/Exon 4 | Male |

Figure 7:
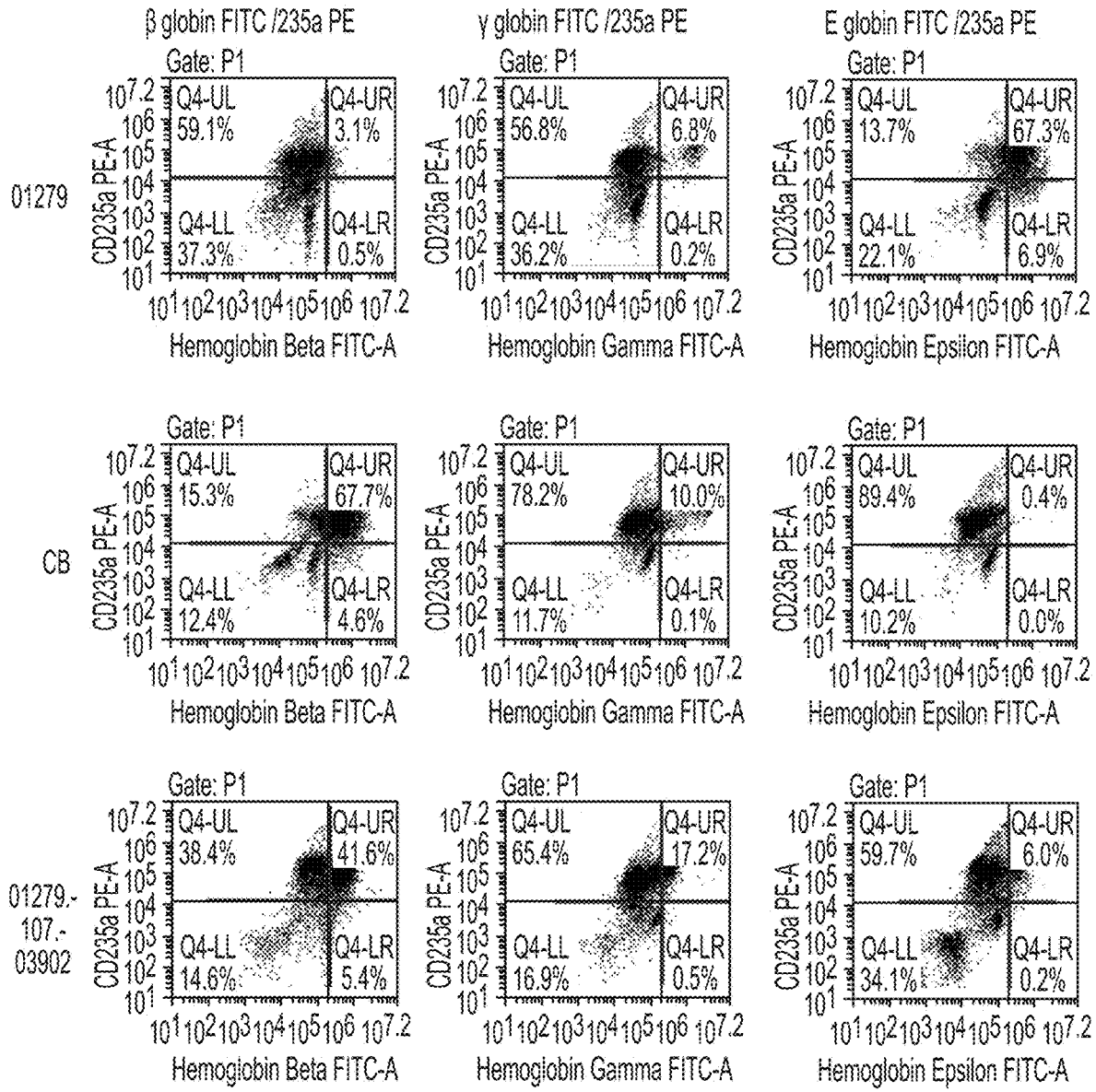
FIG. 7: FACS profile of surface staining of combined CD235 and intracellular globin co-staining at week 7 of erythrocyte differentiation derived from CB) iPSC 01279 (MeCP2WT) and iPSC 01279.107.3902 (MeCP2KO).
Figure 8:
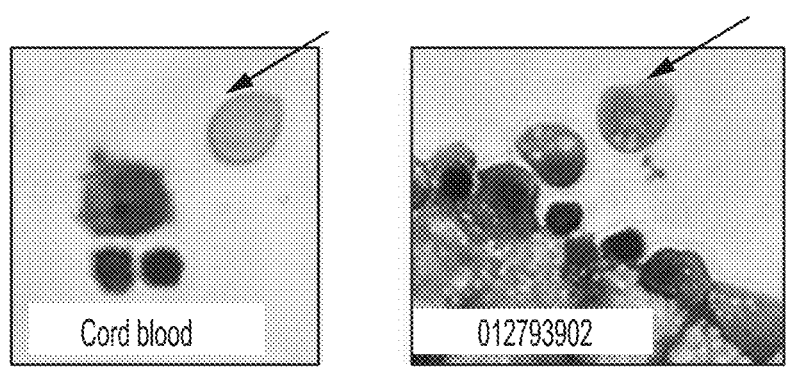
FIG. 8: Cytospins made from end stage erythrocytes derived from CB-derived HPCs and iPSC 01279.107.3902

The efficiency of the MeCP2 knockout clones at differentiating to lymphoid lineages was analyzed by harvesting the 01279.107.3902, 01279.107.3905, 01279.107.3906, 01279.107.3907, and 01279.107.3908 clones at day 5, day 7, day 9 and day 11 of the HPC differentiation described in Example 2. The HPC cells were thawed having been cryopreserved at the time point previously described and plated on Retronectin and DLL4 coated plates. The cells were fed with fresh media every 2 days and were analyzed for pre-T cell markers at 2 weeks (FIG. 13A, 13B), T and NK cell markers at 4 weeks after the HPC cells were thawed. In the analysis of the pre-T cell markers, all of the cells except for the wild-type 01279.107.3904 cells had the presence of pre-T cells identified as CD5$^+$CD7$^+$, CD7$^+$CD45$^+$ and CD5$^+$CD45$^+$. The gating strategy for identifying lymphoid cells generated in vitro is depicted in FIGS. 7 and 8 at day 18 of differentiation. Gating of live cells within the FSC-SSC scatter and lymphoid scatter was performed using propidium iodide followed by staining for CD7 and CD5 positive cells by flow cytometry as well as staining for CD3 APC, CD8 PE and CD56 FITC to identify T cells (CD3$^+$/CD8$^+$) and NK/T cells (CD3$^+$/CD56$^+$) in the population (FIG. 9). The cells were stained for the surface expression of CD45, CD7, and CD5 (FIG. 10) and CD56, CD8, and CD3 (FIG. 11), and the presence of T, NK and NK/T cells were quantified.

Since the input number of cells was known the absolute number of T (CD3$^+$/CD8$^+$), NK (CD3$^-$/CD56$^+$) and NK/T cells (CD3$^+$/CD56$^+$) was determined. The efficiency of the process is calculated by the ratio of absolute number of a cell type (T, NK, or NK/T)/input number of total cells (FIG. 12A) or by the ratio of absolute number of a cell type/input number of HPCs (FIG. 12B). The percentage of T cells (CD3$^+$/CD8$^+$) (FIG. 13) and the percentage of NK cells (CD3$^-$/CD56$^+$) (FIG. 14) were quantified by flow cytometry under FSC-SSC gate and the lymphoid scatter gate. The quantity of emerging NK/T (CD3$^+$/CD56$^+$) (FIG. 15), (CD3$^+$/CD8$^+$) (FIG. 16), NK/T (CD3$^+$/CD56$^+$) and NK (CD3$^-$/CD56$^+$) (FIG. 17) cells were also determined. Further analysis showed that the expression of CD235/CD7, CD144$^+$/DLL4$^+$, and Flk-1$^+$/CD34$^+$ declines at day 11 of differentiation (FIG. 18). Since there is an absence of lymphoid cells at day 11 of differentiation, this may imply that a certain threshold level of expression of these markers is essential to prime cells towards lymphoid differentiation in the presence of DLL4.

Recent studies (Oberlin, et al., 2010) demonstrated the existence of a VE-cadherin (CD144) expressing population, which constitutes less than 0.6% of total human liver cells. This population co-expressed CD34 and CD45 and it displayed greater self-renewal, proliferation, and differentiation capacities than the CD144−CD34$^+$CD45$^+$ counterpart, as assessed by in vitro hematopoietic assays and long-term transplantation experiments in non-obese diabetic/severe combined immunodeficiency (NOD/SCID) mice.

During iPSC-derived HPC generation CD144 expressing cells also expressed Notch-DLL4. Definitive HSCs are defined by their capacity for long-term, multilineage engraftment in adult recipients are detected thereafter in arterial vessels, such as the dorsal aorta, of the region known as the aorta-gonad-mesonephros (AGM) and subsequently home to the fetal liver, where HSCs undergo further maturation and significant proliferative expansion prior to seeding the marrow (Kieusseian et al., 2012) The Notch pathway is essential for definitive HSCs. Notch DLL4 is expressed during hematopoietic differentiation in a sub population of bipotent hematopoietic progenitors (Oberlin et al., 2010; Ayllon et al., 2015). Cells expressing high levels of DLL4 were shown to commit to an endothelial fate while cells expressing low levels of DLL4 had a bias towards hematopoietic fate, but resided very closely to the cells expressing high DLL4. Since the in vitro lymphoid differentiation was performed in the presence of Notch DLL4 the lymphoid progenitors could be VE-Cadherin positive cells expressing low levels of DLL4. Additionally, a minor lymphoid progenitor in human umbilical cord blood was identified to be CD34$^{hi}$CD45RA$^{hi}$ICD7$^+$ (Haddad et al., 2004). To phenotypically identify the lymphoid progenitor during iPSC-derived HPC differentiation, sorting experiments were performed using VE-cadherin (CD144), the pan-leukocyte antigen CD45, the hematoendothelial marker CD34, and minor lymphoid progenitor CD7.

To identify the phenotypic signature of lymphoid cells, a magnetic sorting strategy was performed using day 8 HPC progenitors from TiPSCs 1E and 3902 cells using the list of markers that declined with the loss of lymphoid potential. Day 8 HPC progenitors were harvested and individualized and then placed under 4 conditions for magnetic sorting as described in Table 5. The positive and negative fractions obtained post sorting were plated at a density of 25 k/cm$^2$ to induce T cell differentiation on Ret-DLL4 coated matrix 12 well plates as well as 24 well plates. T cell differentiation was performed as described earlier under hypoxic conditions.

Analysis of the T cell markers (FIG. 19) showed that the MeCP2 KO cell lines, but not the MeCP2 WT cell line, had the potential for lymphoid differentiation. The Day 9 HPC progenitors from the MeCP2 WT cells had essentially no $CD3^+CD8^+$ T cells while the other HPC progenitors tested differentiated to a population of $CD3^+CD8^+$ T cells. Thus, the knockout of the methyl binding domain of MeCP2 enhanced the potential of the HPC progenitors to produce T and NK cells.

Example 5—Differentiation to Beta Cells

The MeCP2WT and MeCP2KO iPS cells were also differentiated to DE cells and EPCs which are capable of generating mono-hormonal beta cells. A schematic representation of the process is provided in FIG. 21. The stages of the pancreatic differentiation process are provided in FIG. 23C. The entire differentiation is performed under hypoxic conditions.

EPCs generated in suspension culture were placed in differentiation medium for the generation of pancreatic cell types. For pancreatic differentiation of EP cells, a protocol described by Nostro et al., 2011 further modified by Cheng et al., 2012a was utilized. The entire process was continued as a 3D culture under hypoxic condtions.

EPC cultures were expanded for 15 days and cultured in SFD media containing Wnt3A (3 ng/ml), FGF-10 (50 ng/ml) and Dorsomorphin (0.75 µM) for three days to generate foregut/midgut endoderm cells. The cells were cultured in high glucose DMEM media containing GlutaMAX (1%), B27 without retinoic acid (1%), ascorbic acid (50 µg/ml), Pen/Strep (1%), KAAD-Cyclopamine (0.25 µM), trans-Retinoic acid (2 µM), Noggin (50 ng/ml), and FGF-10 (50 ng/ml) for three days to generate pancreatic endoderm cells. Following this step the cells were cultured in high glucose DMEM media containing GlutaMAX (1%), B27 without retinoic acid (1%), ascorbic acid (50 g/ml), Pen/Strep (1%), SB431542 (6 µM), and Noggin (50 ng/ml) for three days. Next, the cells were cultured in the previous high glucose DMEM medium supplemented with a Secretase inhibitor (DAPT at 2 µM) for one to two days. From this stage the cells were cultured in SFD media containing glucose (40 mM), nicotinamide (10 mM), SB431542 (6 µM), and Noggin (50 ng/ml) for one to two days. Finally, the cells were cultured in SFD medium containing SB431542 (5.4 µM), Noggin (50 ng/ml), insulin (800 pM), and nicotinamide (10 mM) that was alternated every day between such medium with additional glucose added (40 mM) and no additional glucose added for the next 10 days. The presence of mono hormonal beta cells was detected between days 10-15 of differentiation in a 2D format.

Beta cell cultures were harvested on day 21-25 of differentiation, fixed, and stained for quantitation of PDX1/NeuroD1/C-Peptide/Glucagon/Somatostatin by intracellular flow cytometry (FIGS. 24, 25, 26). The end-stage cultures revealed the presence of mono-hormonal cells. The end-stage cultures were positive for PDX1, NeuroD1 and some levels of NKX6.1. The end-stage aggregates revealed responsiveness to glucose (FIG. 27).

Example 6—Effect of MeCP2KO on HPC Differentiation iPSC clones containing MeCP2WT or MeCP2KO were adapted to hypoxia for 5-10 passages on E8/Matrigel and subjected to the 3D differentiation protocol for the production of HPCs. Aggregates were made from sub confluent iPSCs at a density of 0.25-0.5 million cells per ml in the presence SFD media supplemented with 5 uM blebbistatin. The process was performed in ULA plates or spinner flasks in SFD basal medium containing 75% IMDM, 25% Hams F12, N2-supplement, B27 supplement without retinoic acid 0.05% BSA, 50 ug/ml Ascorbic acid, GlutaMAX, Pen/Strep and $4.5 \times 10^{-4}$ M monothioglycerol. Once the EBs had formed, differentiation was initiated by supplementing the SFD basal media with 50 ng/ml of BMP-4, VEGF, and bFGF for the first 4 days. On the fifth day of differentiating the EBs, the cultures were placed in the presence of Flt-3 Ligand, IL3, IL6, SCF, heparin, and TPO each at 50 ng/ml. The aggregates were harvested on day 9 of HPC differentiation and the emergence of hematopoietic cells was quantified.

The expression of CD43 (FIG. 28), CD34 (FIG. 29), CD34/CD43 (FIG. 30), CD45 (FIG. 31), CD235 (FIG. 32A, FIG. 32B) and DLL-4 was quantified by flow cytometry. The efficiency of converting one iPSC to one HPC (34/43) cells was also quantified (FIG. 34). The entire HPC differentiation was performed under hypoxic conditions. It was observed that, in general, the MeCP2KO resulted in a higher percent of cells positive for CD43, CD34, CD43/CD34, CD45, CD235, and DLL4 on Day 9 of HPC differentiation. In addition, the knockout of MeCP2 resulted in an increase of efficiency in differentiating iPSCs to HPCs by about 2-7 fold.

Example 7—Effect of MeCP2KO on Generating Microglia iPSC clones containing MeCP2WT or MeCP2KO were adapted to hypoxia for 5-10 passages on E8/Matrigel and subjected to the 3D differentiation protocol for the production of HPCs. Aggregates were made from sub confluent iPSCs at a density of 0.25-0.5 million cells per ml in the presence SFD media supplemented with 5 uM blebbistatin. The process was performed in ULA plates or spinner flasks in SFD basal medium containing 75% IMDM, 25% Hams F12, N2-supplement, B27 supplement without retinoic acid 0.05% BSA, 50 ug/ml Ascorbic acid, GlutaMAX, Pen/Strep and $4.5 \times 10^{-4}$ M monothioglycerol.

Once the EBs had formed, differentiation was initiated by supplementing the SFD basal media with 50 ng/ml of BMP-4, VEGF, and bFGF for the first 4 days. On the fifth day of differentiating the EBs, the cultures were placed in the presence of Flt-3 Ligand, IL3, IL6, SCF, heparin, and TPO each at 50 ng/ml. The aggregates were harvested on day 9 of HPC of differentiation and plated on Matrigel coated plates at a cell density of 10-15 k/cm² to initiate microglia differentiation according to the method described by Abud et al., 2017. HPC differentiation was performed under hypoxic conditions while microglia differentiation was performed under normoxic conditions.

The cells were fed with microglia differentiation media containing 25 ng/ml MCSF, 50 ng/ml TGFβ, and 100 ug/ml IL-34 for the first 22 days of differentiation. The cells were placed in microglia maturation media containing 25 ng/ml MCSF, 50 ng/ml TGFβ, 100 ug/ml IL-34, CD200 and CXCL1. The cells were harvested on day 27 and stained for the presence of P2RY, TREM-2, IBA and CXC3CR1 by intracellular flow cytometry to confirm the emergence of microglia in end stage cultures. The purity of end stage microglia at the end of the differentiation process was quantified by flow cytometry (FIG. 36) and the efficiency of generating microglia from one HPC was quantified (FIG. 37). It was observed that the knockout of MeCP2 resulted in increased purity of the microglia cell population as determined by the percent of cells positive for IBA, P2RY, and TREM-2.

Example 8—Effect of MeCP2KO on Generating Lymphoid Cells iPSC clones containing MeCP2WT or MeCP2KO were adapted to hypoxia for 5-10 passages on E8/Matrigel and subjected to the 3D differentiation protocol for the production of HPCs Aggregates were made from sub confluent iPSCs at a density of 0.25-0.5 million cells per ml in the presence SFD media supplemented with 5 uM blebbistatin. The process was performed in ULA plates or spinner flasks in SFD basal medium containing 75% IMDM, 25% Hams F12, N2-supplement, B27 supplement without retinoic acid 0.05% BSA, 50 ug/mL Ascorbic acid, GlutaMAX, Pen/Strep and $4.5 \times 10^{-4}$ M monothioglycerol Once the EBs had formed, differentiation was initiated by supplementing the SFD basal media with 50 ng/ml of BMP-4, VEGF, and bFGF for the first 4 days. On the fifth day of differentiating the EBs, the cultures were placed in the presence of Flt-3 Ligand, IL3, IL6, SCF, heparin, and TPO each at 50 ng/ml. The aggregates were harvested on day 9 of HPC differentiation and plated on ret-DLL4 coated plates at cell density of 25 k/cm². The cells were fed with T cells differentiation media containing 50 ng/ml SCF, TPO, IL-7, and Flt-3 ligand for the first 14 days of differentiation under hypoxic conditions. The cells were harvested at the end of two weeks and the percentage of pre T progenitors (CD45/CD7) (FIG. 38B) and (CD7/CD5) (FIG. 38C) cells were quantified by flow cytometry. A snap shot of the FACS profile for pre T cells (CD5/CD7) is depicted in (FIG. 38A)

Figure 39A:
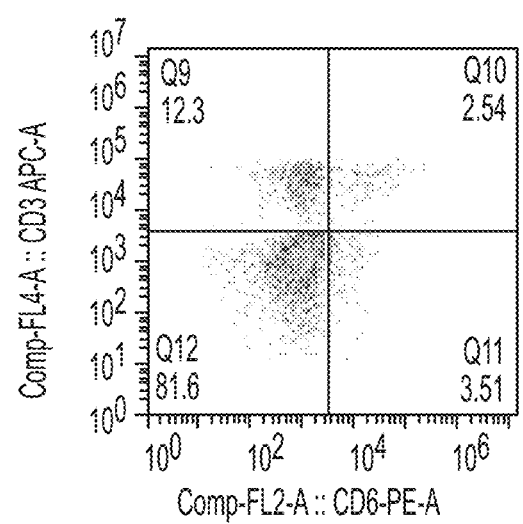
Figure 39B:
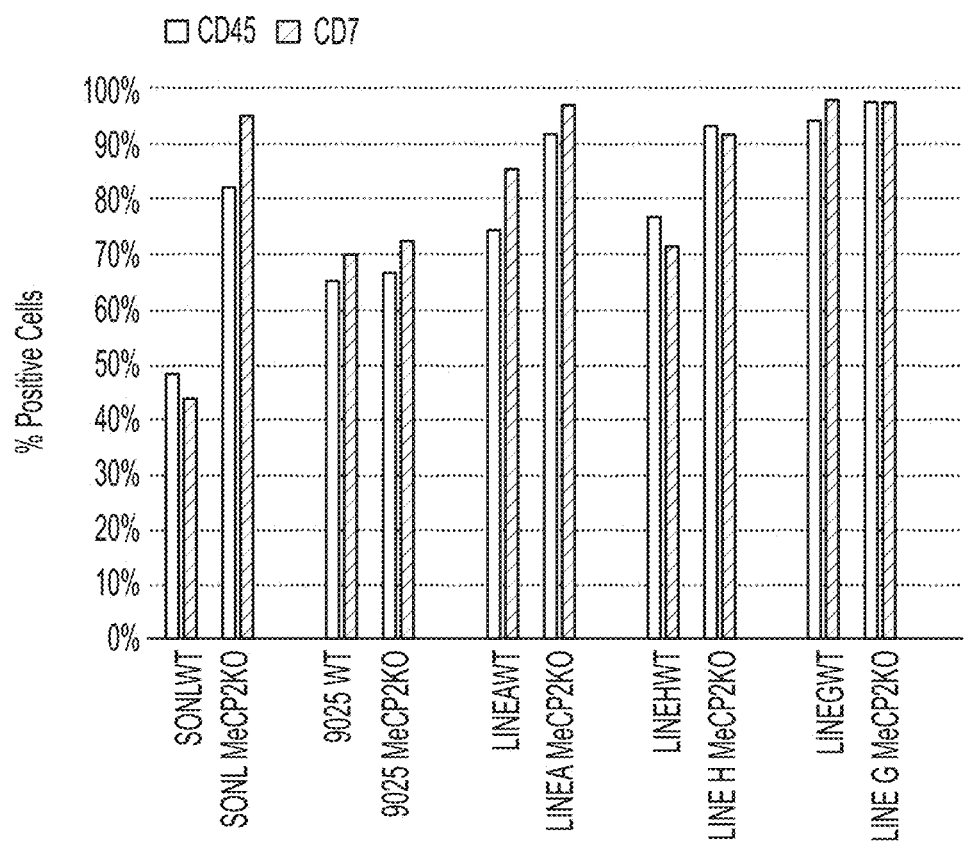
Figure 39C:
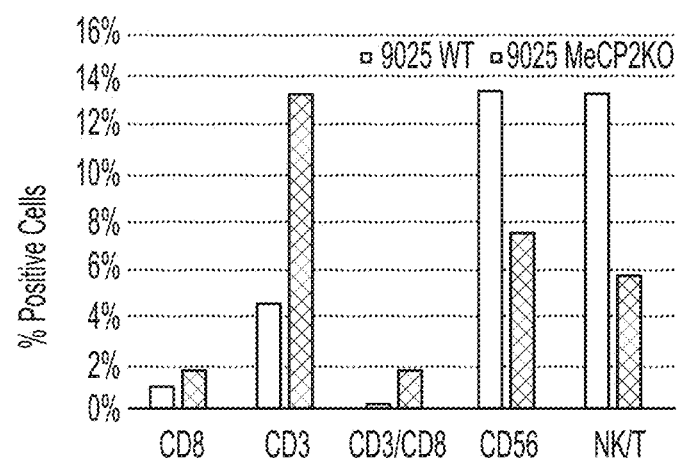
Figure 39D:
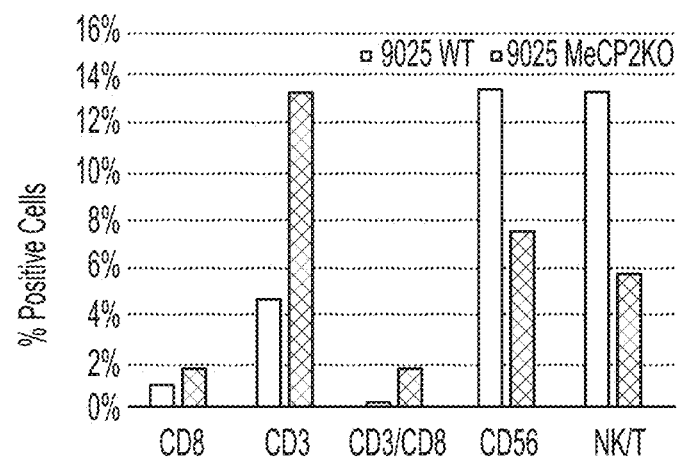
Figure 39E:
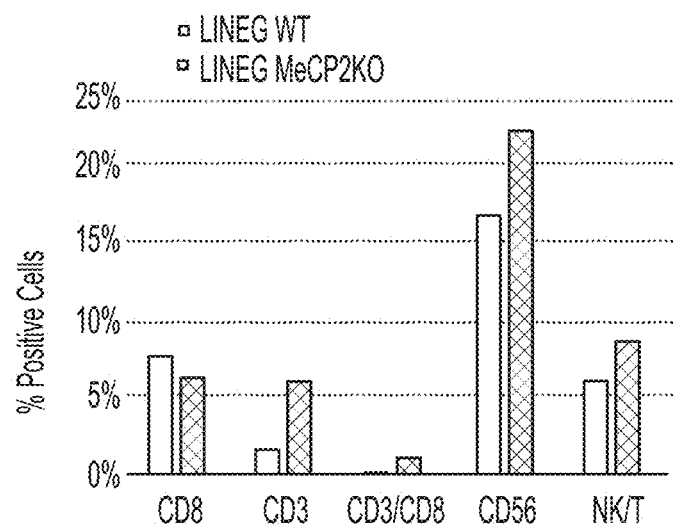
Figure 39F:
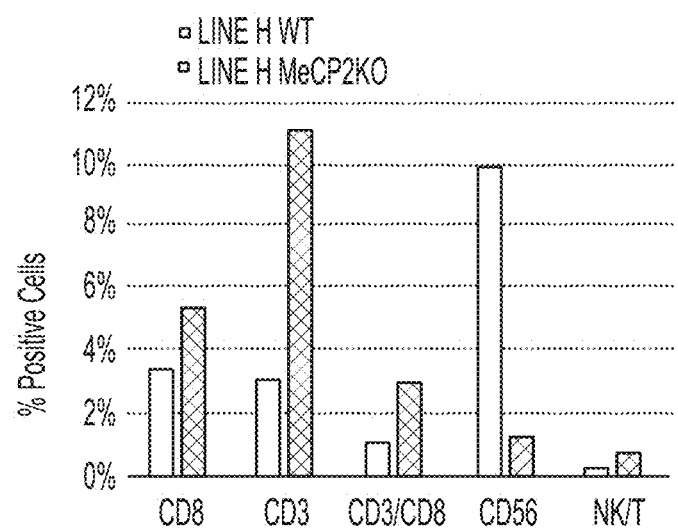

Emerging pre T cells were placed on fresh Ret-DLL4 coated plates and the differentiation was continued for additional 2 weeks in media containing 50 ng/ml SCF, TPO, IL-7, Flt-3 ligand and 10 U/ml of IL-2. A snap shot of the FACS profile for T cells (CD3/CD8) is depicted in (FIG. 39A). Quantification of total CD3, Cytotoxic T ($CD3^+$/$CD8^+$), NK ($CD3-$/$CD56$) and NK/T cells ($CD3^+$/$CD56^+$) was performed for various WT and MeCP2KO clones. SONL (FIG. 39B). iPSC 9025 (FIG. 39C), iPSC Line A (FIG. 39D), Line F (FIG. 39E), Line H (FIG. 39F). Thus, the MeCP2KO iPSCs can be used to efficiently generate T and NK/T cells from iPSCs.

Example 9—Effect of MeCP2KO on Hepatocyte Maturation

The MeCP2WT or MeCP2KO iPSC lines were differentiated to definitive endoderm cells as described in FIG. 21. The definitive endoderm cells were then further differentiated to hepatocyte following the protocol depicted in FIG. 40. The entire differentiation process was performed under hypoxic conditions until Day 25 of the differentiation process. Briefly, the DE cells were cultured in 2D for about 6 days in SFD media supplemented with BMP4 (50 ng/mL), bFGF (10 ng/mL), EGF (10 ng/mL), VEGF (10 ng/mL), HGF (100 ng/mL), Dex (0.1 μM), DMSO (1%), and FGF-10 (60 ng/mL). The cells were then replated on collagen for about 6 days in SFD medium supplemented with bFGF (10 ng/mL), EGF (20 ng/mL), VEGF (10 ng/mL), HGF (100 ng/mL), OSM (20 ng/mL), Dex (0.2 μM), DMSO (1%), DAPT (2 μM), and Vitamin K (6 μg/mL). For the $3^{rd}$ stage, the cells were plated in 2D in William's E medium supplemented with B27 (1×), EGF (20 ng/mL), OSM (20 ng/mL), Dex (0.1 μM), GlutaMAX (1%), and Pen/Strep (1%).

The end stage hepatocytes were harvested using Accumax and stained for the presence of alpha-1-antitrypsin (AAT) and albumin expression by performing intracellular flow cytometry. AAT and albumin are known to be markers of adult liver cells and it was observed that the hepatocytes differentiated from the MeCP2KO iPSCs had higher expression of albumin as compared to the hepatocytes differentiated from the MeCP2WT iPSCs. Thus, the MeCP2KO iPSCs can be used to efficiently generate more mature liver cells.

Example 10—Characterization of Erythroblast Production from MeCP2KO iPSCs iPSC clones containing MeCP2WT or MeCP2KO were adapted to hypoxia for 5-10 passages on E8/Matrigel and subjected to the 3D differentiation protocol for the production of HPCs Aggregates were made from sub confluent iPSCs at a density of 0.25-0.5 million cells per ml in the presence SFD media supplemented with 5 uM blebbistatin. The process was performed in ULA plates or spinner flasks in SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, GlutaMAX, Pen/Strep and 4.5×10-4 M monothioglycerol.

Once the EBs had formed, differentiation was initiated by supplementing the SFD basal media with 50 ng/ml of BMP-4, VEGF, and bFGF for the first 4 days. On the fifth day of differentiating the EBs, the cultures were placed in the presence of Flt-3 Ligand, IL3, IL6, SCF, heparin, and TPO each at 50 ng/ml. The aggregates were harvested on day 9 of HPC differentiation and the emergence of hematopoietic cells was quantified.

To generate human erythroblasts from HPCs derived from iPSCs, the cells were cultured at a density of $0.5-1 \times 10^6$ cells/mL in Primitive Erythroid Expansion Medium (pEEM) for 1-2 weeks. The pEEM media comprised SFEM medium supplemented with 0.3% Excyte (Serologicals), Holo-Transferrin (1 mg/ml, Sigma), Hydrocortisone (1 mM, Sigma), SCF (50 ng/ml, R&D Systems), EPO (2 U/ml, R&D Systems), IL-3 (5 ng/ml), IL-6 (10 ng/ml) and TPO (50 ng/ml). The cells were stained for the presence of Glycophorin (CD235) from weeks 2-7 of differentiation. The kinetics of CD235 expression for each clone undergoing erythrocyte differentiation is depicted in FIG. 42. It was observed that, in general, the erythrocytes differentiated from iPSCs with MeCP2KO had an earlier emergence of CD235 expression during erythroid differentiation and higher percentage of cells positive for CD235.

The cells were co-stained for CD235a and various globins, including β globin, γ globin and ε globin from week 2-7 of erythrocyte differentiation. iPSC SONL MeCP2KO (FIG. 43A), SONL MeCP2WT (FIG. 43B), iPSC TIPS MeCP2KO (FIG. 44A), TIPS MeCP2WT (FIG. 44B), iPSC 9025 MeCP2KO (FIG. 45A), 9025 MeCP2WT (FIG. 45B), iPSC LineA MeCP2KO (FIG. 46A), LineA MeCP2WT (FIG. 46B), iPSC LineH MeCP2KO (FIG. 47A), LineH MeCP2WT (FIG. 47B), iPSC LineG MeCP2KO (FIG. 48A), and LineG MeCP2WT (FIG. 48B). For all of the erythrocytes differentiated from MeCP2KO cell lines, the expression of β globin is accompanied by the decline in the levels of embryonic ε globin indicating the switch from embryonic to adult globins. This is accompanied by the decrease in the levels of fetal gamma globins. Thus, erythrocytes from MeCP2KO iPSCs are more mature than eyrthrocytes differentiated from MeCP2WT iPSCs.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abboud et al., *Blood*, 58:1148-1154, 1981.
Abdul et al., *Neuron*, 2017.
Akkina et al., *J. Virol.*, 70:2581-2585, 1996.
Alexander et al., *Proc. Nat. Acad. Sci. USA*, 85:5092-5096, 1988.
Anderson, *Science* 256:808-813, 1992.
Ausubel et al., *Current Protocols in Molecular Biology*, Greene Publ. Assoc. Inc. & John Wiley & Sons, Inc., MA, 1996.
Ayllon et al., *Leukemia* 29(8): 1741-1753, 2015.
Beerli et al. *Nature Biotechnol.* 20:135-141, 2002.
Bhatnagar, et al. *Proc. Natl. Acad. Sci. USA*, 2014.
Bird A. *Nature*. 1986; 321:209-13, 1986.
Bird, A. *Biochem. Soc. Trans.*, 36:575-583, 2008.
Biswas et al., *Annals NY Acad. Sci.*, 590:582-583, 1990.
Biswas et al., *J. Clin. Microbiol.*, 29:2228-2233, 1991.
Blomer et al., *J. Virol.*, 71(9):6641-6649, 1997.
Chen and Okayama, *Mol. Cell Biol.*, 7(8):2745-2752, 1987.
Cheng et al., *Cell Stem Cell* 10(4): 371-384, 2012.
Choo et al. *Curr. Opin. Struct. Biol.* 10:411-416, 2000.
Critchlow and Jackson, *Trends Biochem Sci.* 23(10):394-8, 1998.
Dillon. *TIBTECH* 11:167-175, 1993.
Doulatov et al., *Cell Stem Cell.* 10:120-36, 2012.
Ercolani et al., *J. Biol. Chem.*, 263:15335-15341, 1988.
Evans, et al., In: Cancer *Principles and Practice of Oncology*, Devita et al. (Eds.), Lippincot-Raven, NY, 1054-1087, 1997.
Fauser et al., *Stem Cells*, 1:73-80, 1981 Fechheimer et al., *Proc Natl. Acad. Sci. USA*, 84:8463-8467, 1987.
Fraley et al., *Proc. Natl. Acad. Sci. USA*, 76:3348-3352, 1979.
Frisan et al., Epstein-Barr Virus Protocols, Part III, 125-127, 2001
Furie and Furie, *Cell* 53: 505-518, 1988.
Gaj et al., *Trends in Biotechnology* 31(7), 397-405, 2013.
Golde et al., *Proc. Natl. Acad. Sci. USA*, 77:593-596, 1980.
Graham and Van Der Eb, *Virology*, 52:456-467, 1973.
Haddad et al., *Blood* 104(13): 3918-3926, 2004.
Haddada et al., in *Current Topics in Microbiology and Immunology*, 1995.
International Publication No. WO 94/09699
International Publication No. WO 95/06128
International Publication No. WO 96/39487
Isalan et al. *Nature Biotechnol.* 19:656-660, 2001.
Jaenisch, *Science* 240:1468-1474, 1988.
Jones P A and Takai D. *Science*. 293:1068-70, 2001.
Kaeppler et al., *Plant Cell Reports* 9: 415-418, 1990.
Karin et al. *Cell*, 36:371-379, 1989.
Kato et al, *J. Biol. Chem.*, 266:3361-3364, 1991.
Kaufman et al., *Proc. Natl. Acad. Sci. USA*, 98:19, 2001.
Kieusseian, A., P. Brunet de la Grange, O. Burlen-Defranoux, I. Godin and A. Cumano (2012). "Immature hematopoietic stem cells undergo maturation in the fetal liver." Development 139(19): 3521-3530.
Kim et al. *J. Biol. Chem.* 269:31,978-31,982, 1994b.
Kim et al. *Proc. Natl. Acad. Sci. USA* 91:883-887, 1994a.
Kim et al., *J. Virol.*, 66:3879-3882, 1992.
Kim et al., *Nature Biotechnology* 31, 251-258, 2013.
Knust et al, *EMBO J.* 761-766, 1987.
Kremer & Perricaudet, *British Medical Bulletin* 51(1):31-44, 1995.
Ladi et al., *Nature Immunology*, 7: 338-343, 2006.
Langle-Rouault et al., *J. Virol.*, 72(7):6181-6185, 1998.
Lappalainen et al. *Clin. Experim. Allergy*, 37:1404-1414, 2007.
Levitskaya et al., *Proc. Natl. Acad. Sci. USA*, 94(23):12616-12621, 1997.
Li et al. *Proc. Natl. Acad. Sci. USA* 89:4275-4279, 1992.
Lloyd et al., *Frontiers in Immunology*, 4(221):1-7, 2013.
Ludwig et al. *Nature Biotech.*, (2):185-187, 2006a.
Ludwig et al. *Nature Methods*, 3(8):637-646, 2006b.
Lusis, *Blood*, 57:13-21, 1981.
Macejak and Sarnow, *Nature*, 353:90-94, 1991.
Maniatis, et al., Molecular Cloning, A Laboratory Manual, Cold Spring Harbor Press, Cold Spring Harbor, N.Y., 1988.
Mann et al., *Cell*, 33:153-159, 1983.
Marshall et al., *Blood*, 96:1591-1593, 2000.
Miller, *Nature* 357:455-460, 1992.
Minskaia and Ryan, 2013
Mitani & Caskey, *TIBTECH* 11:162-166, 1993.
Nabel & Feigner, *TIBTECH* 11:211-217, 1993.
Nabel et al., *Science*, 244(4910):1342-1344, 1989.
Naldini et al., *Science*, 272(5259):263-267, 1996. Zufferey et al., *Nat. Biotechnol.*, 15(9):871-875, Ng, *Nuc. Acid Res.*, 17:601-615, 1989.
Nicola, et al., *Blood*, 54:614-627, 1979.
Nicolas and Rubenstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nostro et al., *Development* 138:861-871, 2011.
Notta et al., *Science*, 218-221, 2011.
Oberlin et al., *Blood* 116(22): 4444-4455, 2010.
Okabe, *J. Cell. Phys.*, 110:43-49, 1982.
Orkin et al., *Blood* 120(15): 2945-2953, 2012.
Pabo et al. *Ann. Rev. Biochem.* 70:313-340, 2001.
Paskind et al., *Virology*, 67:242-248, 1975.
Patent Publication No. EP1507865
PCT Publication No. WO 2006/050330
PCT Publication No. WO 2007/069666
Pelletier and Sonenberg, *Nature*, 334(6180):320-325, 1988.
Potrykus et al., *Mol. Gen. Genet.*, 199(2):169-177, 1985.
Potter et al., *Proc. Natl. Acad. Sci. USA*, 81:7161-7165, 1984.
Quitsche et al., *J. Biol. Chem.*, 264:9539-9545, 1989.

Richards et al., *Cell*, 37:263-272, 1984.
Rippe, et al., *Mol. Cell Biol.*, 10:689-695, 1990.
Sambrook and Russell, *Molecular Cloning: A Laboratory Manual*, 3rd Ed. Cold Spring Harbor
Schernthaner et al., *Blood*, 98:3784-3792, 2001.
Scicchitano et al., *Exp Hematol.* 31:760-9, 2003.
Segal et al. *Curr. Opin. Biotechnol.* 12:632-637, 2001.
Slukvin et al. In: *Directed Production of Specific Blood Lineages from Human Embryonic Stem Cells*, #33, ASCI/AAP Joint Meet. Posters, 2007.
Suzuki et al, EMBO J. 6:1891-1897, 1987.
Takahashi et al., *Cell*, 131(5):861-872, 2007.
Temin, *In: Gene Transfer*, Kucherlapati (Ed.), NY, Plenum Press, 149-188, 1986.
Tur-Kaspa et al., *Mol. Cell Biol.*, 6:716-718, 1986.
U.S. patent application Ser. No. 08/464,599
U.S. patent application Ser. No. 12/478,154
U.S. patent application Ser. No. 12/715,136
U.S. Patent Application No. 2007/0077654
U.S. Patent Application No. 2009/0246875
U.S. Patent Application No. 2010/0210014
U.S. Patent Application No. 2011/0059502
U.S. Patent Application No. 2011/0104125
U.S. Patent Application No. 2011/0301073
U.S. Patent Application No. 2012/0276636
U.S. Patent Application No. 2013/0315884
U.S. Patent Application No. 2014/0120622
U.S. Patent Application No. 2015/0191697
U.S. Patent Application No. 61/088,054
U.S. Pat. No. 4,683,202
U.S. Pat. No. 4,897,355
U.S. Pat. No. 4,946,787
U.S. Pat. No. 5,030,015
U.S. Pat. No. 5,049,386
U.S. Pat. No. 5,302,523
U.S. Pat. No. 5,322,783
U.S. Pat. No. 5,384,253
U.S. Pat. No. 5,464,765
U.S. Pat. No. 5,486,359
U.S. Pat. No. 5,538,877
U.S. Pat. No. 5,538,880
U.S. Pat. No. 5,550,318
U.S. Pat. No. 5,556,954
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,843,780
U.S. Pat. No. 5,928,906
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,103,470
U.S. Pat. No. 6,200,806
U.S. Pat. No. 6,416,998
U.S. Pat. No. 7,029,913
U.S. Pat. No. 7,442,548
U.S. Pat. No. 7,598,364
U.S. Pat. No. 7,989,425
U.S. Pat. No. 8,058,065
U.S. Pat. No. 8,071,369
U.S. Pat. No. 8,129,187
U.S. Pat. No. 8,183,038
U.S. Pat. No. 8,268,620
U.S. Pat. No. 8,372,642
U.S. Pat. No. 8,546,140
U.S. Pat. No. 8,691,574
U.S. Pat. No. 8,741,648
U.S. Pat. No. 8,900,871
U.S. Pat. No. 9,175,268
U.S. Patent Publication No. 20020055144
U.S. Patent Publication No. 20090148425
Van Brunt, *Biotechnology* 6(10):1149-1154, 1988.
Vigne, *Restorative Neurology and Neuroscience* 8:35-36, 1995.
Wilson et al., *Nature Reviews Immunology*, 9: 91-105, 2009.
Wilson et al., *Science*, 244:1344-1346, 1989.
Wong et al., *Gene*, 10:87-94, 1980. Kaneda et al., *Science*, 243:375-378, 1989.
Wynn, *Nature Immunology*, 6:1069-1070, 2005.
Xi et al. *Biomed Res Int*, 2013.
Yamanaka et al., *Cell*, 131(5):861-72, 2007.
Yu et al. *Gene Therapy* 1:13-26, 1994.
Yu et al. *Science*, 318(5858):1917-1920, 2007.

---

What is claimed is:

1. A method of differentiating hematopoietic precursor cells (HPCs) derived from pluripotent stem cells (PSCs) into erythroid, lymphoid or myeloid cells comprising culturing HPCs that comprise disrupted Methyl-CpG Binding Protein 2 (MeCP2), and differentiating the HPCs to produce erythroid, myeloid or lymphoid cells.

2. The method of claim 1, wherein the HPCs express a non-functional MeCP2 that has essentially no binding to methylated DNA.

3. The method of claim 1, wherein the HPCs do not express MeCP2 at levels that are sufficient to effect MeCP2 DNA binding activity.

4. The method of claim 2, wherein the MeCP2 is non-functional by virtue of a truncation, exon skipping, or mutation in the MeCP2 gene.

5. The method of claim 1, wherein the HPCs comprising disrupted MeCP2 are prepared by contacting PSCs with siRNA, shRNA, protein inhibitor, or a small molecule inhibitor of MeCP2 and differentiating the PSCs to produce HPCs having disrupted MeCP2.

6. The method of claim 1, wherein the HPCs comprising disrupted MeCP2 are prepared by engineering PSCs to disrupt the expression, activity, and/or function of MeCP2 and differentiating the PSCs to produce HPCs.

7. The method of claim 6, wherein engineering comprises genetic disruption of the MeCP2 gene.

8. The method of claim 7, wherein genetic disruption comprises insertion of a stop codon by introduction of a DNA-binding domain prior to the methyl CpG binding domain of MeCP2.

9. The method of claim 8, wherein the DNA-binding domain is a zinc finger, TALE or CRISPR DNA-binding domain.

10. The method of claim 6, wherein the PSCs are induced pluripotent stem cells (iPScs).

11. The method of claim 6, wherein differentiating the PSCs to produce HPCs comprises the sequential steps of:
   (a) culturing the PSCs in a first defined media comprising at least one growth factor;
   (b) culturing the cells in a second defined media comprising an amount of BMP4 and VEGF, and bFGF sufficient to promote differentiation in a plurality of the cells; and
   (c) culturing the cells in a third defined media comprising an amount of IL-3, Flt3 ligand, and IL-6 sufficient to promote differentiation in a plurality of the cells, thereby producing HPCs.

12. The method of claim 11, wherein the HPCs express at least two markers from the group consisting of CD43, CD34, CD31, CD41, CD235, DLL4 and CD45.

13. The method of claim 11, wherein HPCs that express CD34 and CD43 are cultured under hypoxic conditions for differentiating the HPCs to produce lymphoid cells.

14. The method of claim 11, wherein a plurality of the pluripotent cells form embryoid bodies (EBs).

15. The method of claim 1, wherein the erythroid cells are erythrocytes or erythroblasts.

16. The method of claim 15, wherein the erythrocytes have a higher expression of beta globin as compared to the expression of epsilon globin and/or gamma globin.

17. The method of claim 1, wherein differentiating the HPCs to erythroid cells comprises:
   (i) culturing the HPCs in a defined media to generate erythroblasts; and
   (ii) culturing the erythroblasts under expansion conditions to produce an enriched population of erythroid cells.

18. The method of claim 17, wherein the enriched population of erythroid cells comprises greater than 70% erythroid cells.

19. The method of claim 18, wherein the erythroid cells express CD71, CD235a and/or CD36.

20. A method of differentiating definitive endoderm (DE) cells derived from PSCs into endodermal cells comprising obtaining DE cells that comprise disrupted Methyl-CpG Binding Protein 2 (MeCP2) and differentiating the DEs to produce endodermal cells.

21. The method of claim 1, wherein the erythroid, myeloid or lymphoid cells are further cultured and expanded.

22. The method of claim 17, wherein the defined media comprises excyte and holo-transferrin.

* * * * *

UNITED STATES PATENT AND TRADEMARK OFFICE
CERTIFICATE OF CORRECTION

| | |
|---|---|
| PATENT NO. | : 10,961,505 B2 |
| APPLICATION NO. | : 15/725931 |
| DATED | : March 30, 2021 |
| INVENTOR(S) | : Rajesh et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 361 days.

Signed and Sealed this
Thirty-first Day of January, 2023

*Katherine Kelly Vidal*

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 489
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (50)..(52)
<223> OTHER INFORMATION: Xaa can be any naturally occurring amino acid

<400> SEQUENCE: 1

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30
```

```
Lys Asp Lys Lys Glu Glu Lys Glu Gly Lys His Glu Pro Val Gln Pro
            35                  40                  45

Ser Xaa Xaa Xaa Ala His His Ser Ala Glu Pro Ala Glu Ala Gly Lys
    50                  55                  60

Ala Glu Thr Ser Glu Gly Ser Gly Ser Ala Pro Ala Val Pro Glu Ala
65                  70                  75                  80

Ser Ala Ser Pro Lys Gln Arg Arg Ser Ile Ile Arg Asp Arg Gly Pro
                85                  90                  95

Met Tyr Asp Asp Pro Thr Leu Pro Glu Gly Trp Thr Arg Lys Leu Lys
            100                 105                 110

Gln Arg Lys Ser Gly Arg Ser Ala Gly Lys Tyr Asp Val Tyr Leu Ile
            115                 120                 125

Asn Pro Gln Gly Lys Ala Phe Arg Ser Lys Val Glu Leu Ile Ala Tyr
        130                 135                 140

Phe Glu Lys Val Gly Asp Thr Ser Leu Asp Pro Asn Asp Phe Asp Phe
145                 150                 155                 160

Thr Val Thr Gly Arg Gly Ser Pro Ser Arg Arg Glu Gln Lys Pro Pro
                165                 170                 175

Lys Lys Pro Lys Ser Pro Lys Ala Pro Gly Thr Gly Arg Gly Arg Gly
            180                 185                 190

Arg Pro Lys Gly Ser Gly Thr Thr Arg Pro Lys Ala Ala Thr Ser Glu
        195                 200                 205

Gly Val Gln Val Lys Arg Val Leu Glu Lys Ser Pro Gly Lys Leu Leu
210                 215                 220

Val Lys Met Pro Phe Gln Thr Ser Pro Gly Gly Lys Ala Glu Gly Gly
225                 230                 235                 240

Gly Ala Thr Thr Ser Thr Gln Val Met Val Ile Lys Arg Pro Gly Arg
                245                 250                 255

Lys Arg Lys Ala Glu Ala Asp Pro Gln Ala Ile Pro Lys Lys Arg Gly
            260                 265                 270

Arg Lys Pro Gly Ser Val Val Ala Ala Ala Ala Glu Ala Lys Lys
        275                 280                 285

Lys Ala Val Lys Glu Ser Ser Ile Arg Ser Val Gln Glu Thr Val Leu
290                 295                 300

Pro Ile Lys Lys Arg Lys Thr Arg Glu Thr Val Ser Ile Glu Val Lys
305                 310                 315                 320

Glu Val Val Lys Pro Leu Leu Val Ser Thr Leu Gly Glu Lys Ser Gly
                325                 330                 335

Lys Gly Leu Lys Thr Cys Lys Ser Pro Gly Arg Lys Ser Lys Glu Ser
            340                 345                 350

Ser Pro Lys Gly Arg Ser Ser Ala Ser Ser Pro Lys Lys Glu
        355                 360                 365

His His His His His His Ser Glu Ser Pro Lys Ala Pro Val Pro
        370                 375                 380

Leu Leu Pro Pro Leu Pro Pro Pro Glu Pro Glu Ser Ser Glu
385                 390                 395                 400

Asp Pro Thr Ser Pro Glu Pro Gln Asp Leu Ser Ser Val Cys
                405                 410                 415

Lys Glu Glu Lys Met Pro Arg Gly Gly Ser Leu Glu Ser Asp Gly Cys
            420                 425                 430

Pro Lys Glu Pro Ala Lys Thr Gln Pro Ala Val Ala Thr Ala Ala Thr
        435                 440                 445
```

-continued

```
Ala Ala Glu Lys Tyr Lys His Arg Gly Glu Gly Glu Arg Lys Asp Ile
    450             455                 460

Val Ser Ser Met Pro Arg Pro Asn Arg Glu Glu Pro Val Asp Ser
465             470                 475                 480

Arg Thr Pro Val Thr Glu Arg Val Ser
                485

<210> SEQ ID NO 2
<211> LENGTH: 501
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (62)..(64)
<223> OTHER INFORMATION: Xaa can be any naturally occurring amino acid

<400> SEQUENCE: 2

Met Ala Ala Ala Ala Ala Ala Pro Ser Gly Gly Gly Gly Gly
1               5                   10                  15

Glu Glu Glu Arg Leu Glu Glu Lys Ser Glu Asp Gln Asp Leu Gln Gly
                20                  25                  30

Leu Lys Asp Lys Pro Leu Lys Phe Lys Val Lys Lys Asp Lys Lys
            35                  40                  45

Glu Glu Lys Glu Gly Lys His Glu Pro Val Gln Pro Ser Xaa Xaa Xaa
50                  55                  60

Ala His His Ser Ala Glu Pro Ala Glu Ala Gly Lys Ala Glu Thr Ser
65                  70                  75                  80

Glu Gly Ser Gly Ser Ala Pro Ala Val Pro Glu Ala Ser Ala Ser Pro
                85                  90                  95

Lys Gln Arg Arg Ser Ile Ile Arg Asp Arg Gly Pro Met Tyr Asp Asp
            100                 105                 110

Pro Thr Leu Pro Glu Gly Trp Thr Arg Lys Leu Lys Gln Arg Lys Ser
        115                 120                 125

Gly Arg Ser Ala Gly Lys Tyr Asp Val Tyr Leu Ile Asn Pro Gln Gly
    130                 135                 140

Lys Ala Phe Arg Ser Lys Val Glu Leu Ile Ala Tyr Phe Glu Lys Val
145                 150                 155                 160

Gly Asp Thr Ser Leu Asp Pro Asn Asp Phe Asp Phe Thr Val Thr Gly
                165                 170                 175

Arg Gly Ser Pro Ser Arg Arg Glu Gln Lys Pro Pro Lys Lys Pro Lys
            180                 185                 190

Ser Pro Lys Ala Pro Gly Thr Gly Arg Gly Arg Gly Arg Pro Lys Gly
        195                 200                 205

Ser Gly Thr Thr Arg Pro Lys Ala Ala Thr Ser Glu Gly Val Gln Val
    210                 215                 220

Lys Arg Val Leu Glu Lys Ser Pro Gly Lys Leu Leu Val Lys Met Pro
225                 230                 235                 240

Phe Gln Thr Ser Pro Gly Gly Lys Ala Glu Gly Gly Ala Thr Thr
                245                 250                 255

Ser Thr Gln Val Met Val Ile Lys Arg Pro Gly Arg Lys Arg Lys Ala
            260                 265                 270

Glu Ala Asp Pro Gln Ala Ile Pro Lys Lys Arg Gly Arg Lys Pro Gly
        275                 280                 285

Ser Val Val Ala Ala Ala Ala Glu Ala Lys Lys Lys Ala Val Lys
    290                 295                 300
```

```
Glu Ser Ser Ile Arg Ser Val Gln Glu Thr Val Leu Pro Ile Lys Lys
305                 310                 315                 320

Arg Lys Thr Arg Glu Thr Val Ser Ile Glu Val Lys Glu Val Val Lys
            325                 330                 335

Pro Leu Leu Val Ser Thr Leu Gly Glu Lys Ser Gly Lys Gly Leu Lys
            340                 345                 350

Thr Cys Lys Ser Pro Gly Arg Lys Ser Lys Glu Ser Ser Pro Lys Gly
            355                 360                 365

Arg Ser Ser Ser Ala Ser Ser Pro Lys Lys Glu His His His His
            370                 375                 380

His His His Ser Glu Ser Pro Lys Ala Pro Val Pro Leu Leu Pro Pro
385                 390                 395                 400

Leu Pro Pro Pro Pro Glu Pro Glu Ser Ser Glu Asp Pro Thr Ser
            405                 410                 415

Pro Pro Glu Pro Gln Asp Leu Ser Ser Ser Val Cys Lys Glu Glu Lys
            420                 425                 430

Met Pro Arg Gly Gly Ser Leu Glu Ser Asp Gly Cys Pro Lys Glu Pro
            435                 440                 445

Ala Lys Thr Gln Pro Ala Val Ala Thr Ala Ala Thr Ala Ala Glu Lys
            450                 455                 460

Tyr Lys His Arg Gly Glu Gly Glu Arg Lys Asp Ile Val Ser Ser Ser
465                 470                 475                 480

Met Pro Arg Pro Asn Arg Glu Glu Pro Val Asp Ser Arg Thr Pro Val
                485                 490                 495

Thr Glu Arg Val Ser
            500

<210> SEQ ID NO 3
<211> LENGTH: 175
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (50)..(52)
<223> OTHER INFORMATION: Xaa can be any naturally occurring amino acid

<400> SEQUENCE: 3

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45

Ser Xaa Xaa Xaa Ala His His Ser Ala Glu Pro Ala Glu Ala Gly Lys
    50                  55                  60

Ala Glu Thr Ser Glu Gly Ser Gly Ser Ala Pro Ala Val Pro Glu Ala
65                  70                  75                  80

Ser Ala Ser Pro Lys Gln Arg Arg Ser Ile Ile Arg Asp Arg Gly Pro
                85                  90                  95

Met Tyr Asp Asp Pro Thr Leu Pro Glu Gly Trp Thr Arg Lys Leu Lys
            100                 105                 110

Gln Arg Lys Ser Gly Arg Ser Ala Gly Lys Tyr Asp Val Tyr Leu Ile
        115                 120                 125

Asn Pro Gln Gly Lys Ala Phe Arg Ser Lys Val Glu Leu Ile Ala Tyr
```

```
                130             135             140
Phe Glu Lys Leu Gln Glu Leu Ala Glu Ala Gly Asp Ala Pro Lys Gly
145                 150                 155                 160

Ala Ala Pro Arg Asp Pro Arg Arg Pro Arg Gln Arg Val Cys Arg
                165                 170                 175

<210> SEQ ID NO 4
<211> LENGTH: 53
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (50)..(52)
<223> OTHER INFORMATION: Xaa can be any naturally occurring amino acid

<400> SEQUENCE: 4

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
                20                  25                  30

Lys Asp Lys Lys Glu Glu Lys Glu Gly Lys His Glu Pro Val Gln Pro
            35                  40                  45

Ser Xaa Xaa Xaa Ala
    50
```